(12) United States Patent
Steiner et al.

(10) Patent No.: US 12,247,047 B2
(45) Date of Patent: Mar. 11, 2025

(54) ARNATAR COMPOUNDS AND METHODS FOR ENHANCED CELLULAR UPTAKE

(71) Applicant: Arnatar Therapeutics, Inc, San Diego, CA (US)

(72) Inventors: Derek Steiner, Del Mar, CA (US); Xuehai Liang, Del Mar, CA (US); Yangfeng Wang, Carlsbad, CA (US)

(73) Assignee: ARNATAR THERAPEUTICS, INC, San Diego, CA (US)

( * ) Notice: Subject to any disclaimer, the term of this patent is extended or adjusted under 35 U.S.C. 154(b) by 0 days.

(21) Appl. No.: 18/792,393

(22) Filed: Aug. 1, 2024

(65) Prior Publication Data

US 2024/0417422 A1    Dec. 19, 2024

Related U.S. Application Data

(63) Continuation of application No. PCT/US2023/084692, filed on Dec. 18, 2023.

(60) Provisional application No. 63/433,730, filed on Dec. 19, 2022, provisional application No. 63/533,273, filed on Aug. 17, 2023, provisional application No. 63/602,245, filed on Nov. 22, 2023.

(51) Int. Cl.
    *C07H 21/02*    (2006.01)
    *A61K 47/54*    (2017.01)
    *C07H 15/08*    (2006.01)

(52) U.S. Cl.
    CPC ........... *C07H 21/02* (2013.01); *A61K 47/549* (2017.08); *C07H 15/08* (2013.01)

(58) Field of Classification Search
    CPC ....... C07H 21/02; C07H 15/08; A61K 47/549
    See application file for complete search history.

(56) References Cited

U.S. PATENT DOCUMENTS

| 7,582,744 B2 | 9/2009 | Manoharan et al. |
| 7,772,203 B2 | 8/2010 | Zamore et al. |
| 8,106,022 B2 | 1/2012 | Manoharan et al. |
| 9,181,549 B2 | 11/2015 | Prakash et al. |
| 9,506,030 B2 | 11/2016 | Bhat |
| 9,796,756 B2 | 10/2017 | Hadwiger et al. |
| 10,087,208 B2 | 10/2018 | Guzaev et al. |
| 10,344,275 B2 | 7/2019 | Wan et al. |
| 10,570,169 B2 | 2/2020 | Seth et al. |
| 11,110,174 B2 | 9/2021 | Manoharan et al. |
| 11,692,001 B2 | 7/2023 | Poon et al. |

FOREIGN PATENT DOCUMENTS

| EP | 0313219 | 5/1996 |
| EP | 3357507 | 8/2018 |
| WO | WO2009002944 | 12/2008 |
| WO | WO2018/031933 | 2/2018 |
| WO | WO 2021257916 | 12/2021 |
| WO | WO 2021257917 | 12/2021 |
| WO | WO 2022136466 | 6/2022 |
| WO | WO 2022162154 | 8/2022 |
| WO | WO 2022162161 | 8/2022 |
| WO | WO2022261005 | 12/2022 |
| WO | WO2023/034719 | 3/2023 |
| WO | PCT/US2023/08692 | 12/2023 |
| WO | PCT/US2023084688 | 12/2023 |

OTHER PUBLICATIONS

Ditzel et al. (eds.), Design and Delivery of SiRNA Therapeutics, 2021, Methods in Molecular Biology, vol. 2282, Springer Science+Business Media, LLC, p. 77-100. (Year: 2021).*
U.S. Pat. No. 11,110,174 (Exhibit 1, not provided herein).
U.S. Pat. No. 9,796,756 (Exhibit 2, not provided herein).
U.S. Pat. No. 9,181,549 (Exhibit 3, not provided herein).
U.S. Pat. No. 10,344,275 (Exhibit 4, not provided herein).
U.S. Pat. No. 10,570,169 (Exhibit 5, not provided herein).
U.S. Pat. No. 9,506,030 (Exhibit 6, not provided herein).
U.S. Pat. No. 7,582,744 (Exhibit 7, not provided herein).
U.S. Pat. No. 8,106,022 (Exhibit 8, not provided herein).
U.S. Pat. No. 11,692,001 (Exhibit 9, not provided herein).
U.S. Pat. No. 10,087,208 (Exhibit 10, not provided herein).
U.S. Pat. No. 7,772,203 (Exhibit 11, not provided herein).
PCT/US2023/084692 (Exhibit 12).
PCTUS2023084688 (Exhibit 13).
WO 2022162161 (Exhibit 14).
WO 2022162154 (Exhibit 15).
WO 2022136466 (Exhibit 16).
WO 2021257917 (Exhibit 17).
WO 2021257916 (Exhibit 18).
WO2018031933 (Exhibit 19).
WO2023034719 (Exhibit 20).
WO2009002944 (Exhibit 21.
WO2022261005 (Exhibit 22).
EP3357507 (Exhibit 23).
EP0313219 (Exhibit 24).
Paunovska et al., Drug Delivery Systems for RNA Therapeutics, 2022, Nature Reviews Genetics, 23(5):265-280 (Exhibit 25).
Chen et al., 2022, Molecular Therapy, Nucleic Acids, 29:150-160). (Exhibit 26).
Sharma et al., 2018, Bioconjugate Chem, 29:2478-2488 (Exhibit 27).
Nair et al., 2014, J. Am. Chem. Soc. 136(49):16958-16961 (Exhibit 28).
Keam, 2022, Drugs, 82:1419-1425 (Exhibit 29).
Prakash et al., 2014, Nucleic Acids Res, 42(13):8796-807 (Exhibit 30).

(Continued)

*Primary Examiner* — Jonathan S Lau
(74) *Attorney, Agent, or Firm* — ADRIANO & ASSOCIATES

(57) ABSTRACT

This invention generally relates to the field of compounds and methods for enhanced cellular uptake. In particular, the invention relates to N-acetylgalactosamine compounds and their conjugates. Also provided are methods for the preparation of these molecules and possible uses thereof, in particular in medicine.

8 Claims, 4 Drawing Sheets
Specification includes a Sequence Listing.

(56) References Cited

OTHER PUBLICATIONS

Debacker et al., 2020, Molecular Therapy, 28(8):1759-1771 (Exhibit 31).
Huang et al., 2017, Bioconjugate Chem, 28:283-295 (Exhibit 32).
Nair et al., 2017, Nucleic Acids Res, 45(19):10969-10977 (Exhibit 33).
Moumné et al, Oligonucleotide Therapeutics: From Discovery and Development to Patentability, Pharmaceutics, 2022, 14(2):260; (Exhibit 34).
Friedrich and Aigner, Therapeutic siRNA: State-of-the-Art and Future Perspectives, 2022, BioDrugs, 36(5):549-571 (Exhibit 35).
Hu et al., Therapeutic siRNA: State of the Art, Signal Transduction and Targeted Therapy, 2020, 5:101) (Exhibit 36).
Wang et al., Therapeutic peptides: current applications and future directions. Sig Transduct Target Ther 7, 48 (2022) (Exhibit 37).
Qi et al., Therapeutic hexapeptide (PGPIPN) prevents and cures alcoholic fatty liver disease by affecting the expressions of genes related with lipid metabolism and oxidative stress. Oncotarget. Sep. 30, 2017;8(50):88079-88093(Exhibit 38).
Xun Ye et al., Peptide mediated therapy in fibrosis: Mechanisms, advances and prospects, Biomedicine & Pharmacotherapy, vol. 157, 2023, 113978.(Exhibit 39).
Muriel P, Rivera-Espinoza Y. Beneficial drugs for liver diseases. J Appl Toxicol. Mar. 2008;28(2):93-103. doi: 10.1002/jat.1310. PMID: 17966118.(Exhibit 40).
Schikora et al, Inorganica Chimica Acta 452:118-124 (Exhibit 41).
Paunovska et al., Drug Delivery Systems for RNA Therapeutics, 2022, Nature Reviews Genetics, 23(5):265-280.
Huang et al., 2017, Bioconjugate Chem, 28:283-295.
Current Protocols in Nucleic Acid Chemistry (2000) 3.1.1-3.1.28.
Chen et al., 2022, Molecular Therapy, Nucleic Acids, 29:150-160).
Sharma et al., 2018, Bioconjugate Chem, 29:2478-2488.
Nair et al., 2014, J. Am. Chem. Soc. 136(49):16958-16961.
Keam, 2022, Drugs, 82:1419-1425.
Prakash et al., 2014, Nucleic Acids Res, 42(13):8796-807.
Debacker et al., 2020, Molecular Therapy, 28(8):1759-1771.
Nair et al., 2017, Nucleic Acids Res, 45(19):10969-10977.
Moumné et al., Oligonucleotide Therapeutics: From Discovery and Development to Patentability, Pharmaceutics, 2022, 14(2):260.
Friedrich and Aigner, Therapeutic siRNA; State-of-the-Art and Future Perspectives, 2022, BioDrugs, 36(5):549-571.
Hu et al., Therapeutic siRNA: State of the Art, Signal Transduction and Targeted Therapy, 2020, 5:101).
Wang et al., Therapeutic peptides: current applications and future directions. Sig Transduct Target Ther 7, 48 (2022).
Qi et al., Therapeutic hexapeptide (PGPIPN) prevents and cures alcoholic fatty liver disease by affecting the expressions of genes related with lipid metabolism and oxidative stress, Oncotarget. Sep. 30, 2017;8(50):88079-88093.
Xun Ye et al., Peptide mediated therapy in fibrosis: Mechanisms, advances and prospects, Biomedicine & Pharmacotherapy, vol. 157, 2023, 113978.
Muriel P, Rivera-Espinoza Y. Beneficial drugs for liver diseases. J Appl Toxicol. Mar. 2008;28(2):93-103. doi: 10.1002/jat.1310. PMID: 17966118.
Schikora et al, Inorganica Chimica Acta 452:118-124.
International Search Report, revised version dated Aug. 15, 2024 issued in connection with parent priority application, PCT/US2023/084692, published as WO2024/137545.
Written Opinion of the International Searching Authority issued in connection with parent priority application parent, PCT application PCT/US2023/084692, published as WO2024/137545, publication date: Jul. 25, 2024.

* cited by examiner

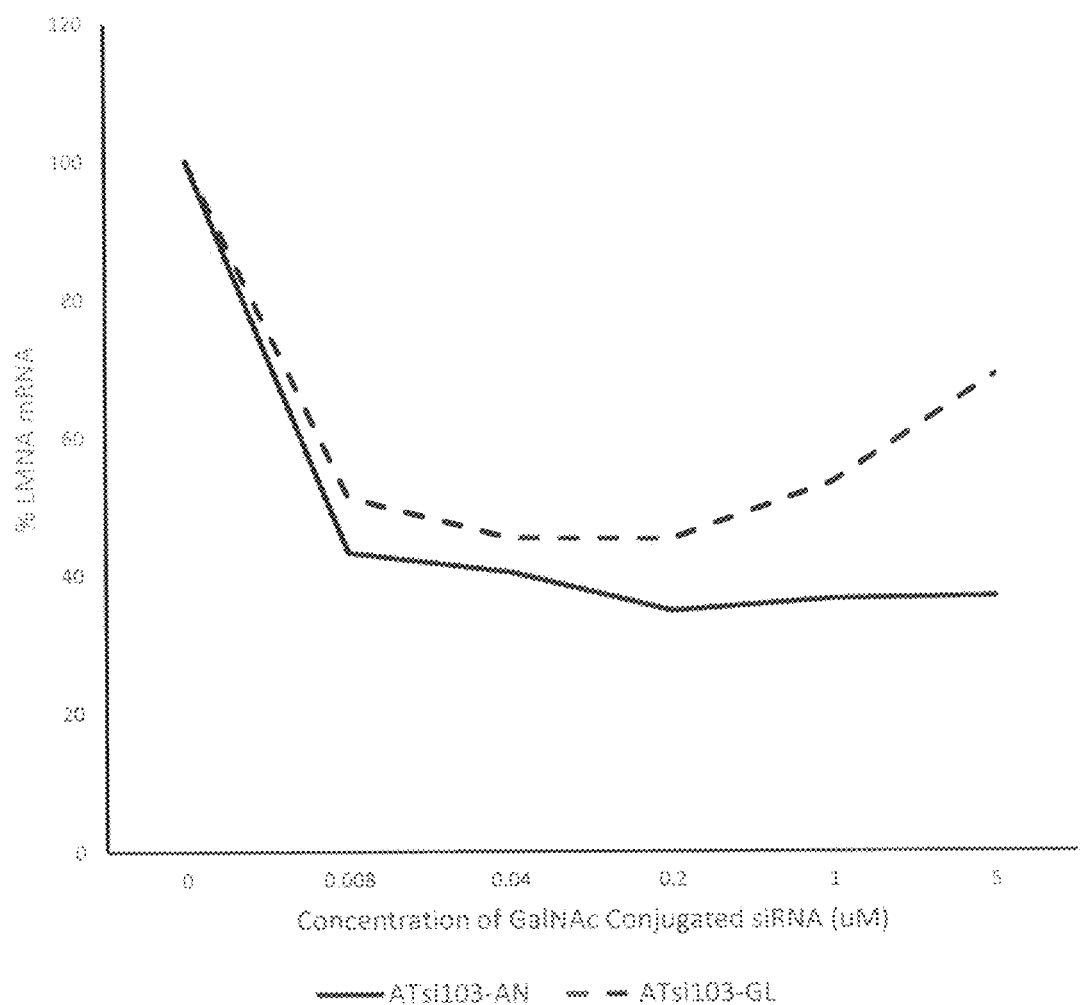
FIGURE 1: LMNA mRNA levels in Human Primary Hepatocytes (HPH) 51 hours after free uptake of GalNAc conjugated siRNAs at different doses (μM).

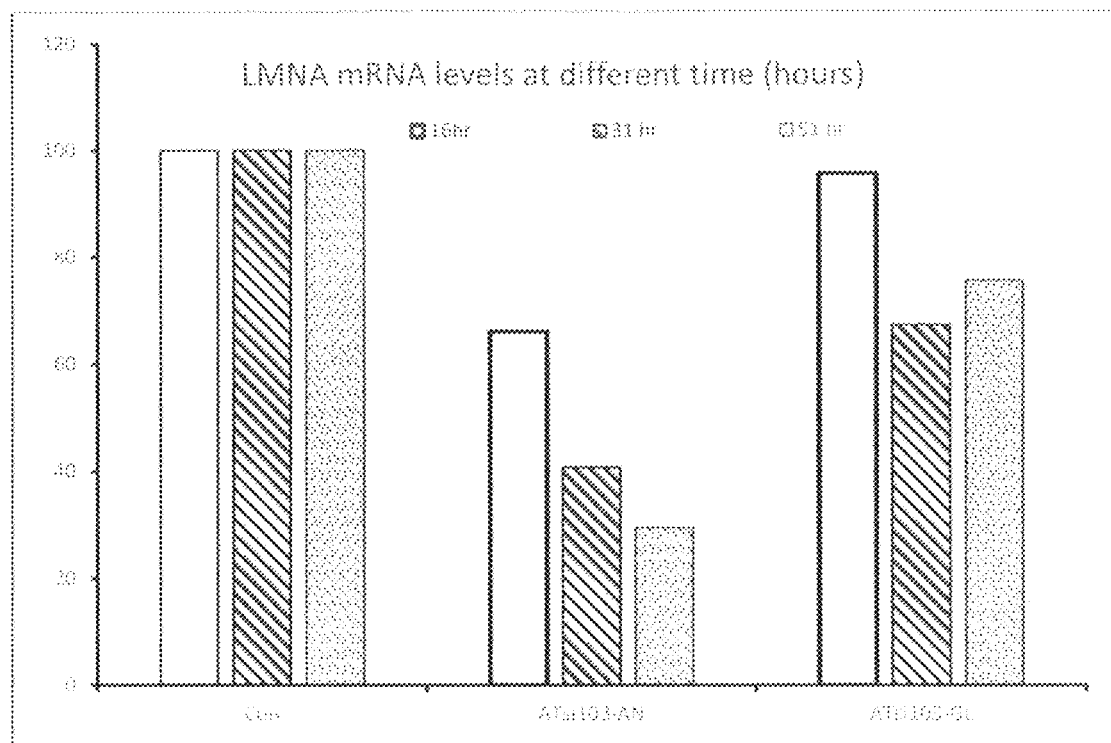
FIGURE 2: LMNA mRNA levels in Human Primary Hepatocytes (HPH) over time after free uptake of GalNAc conjugated siRNAs (5 μM).

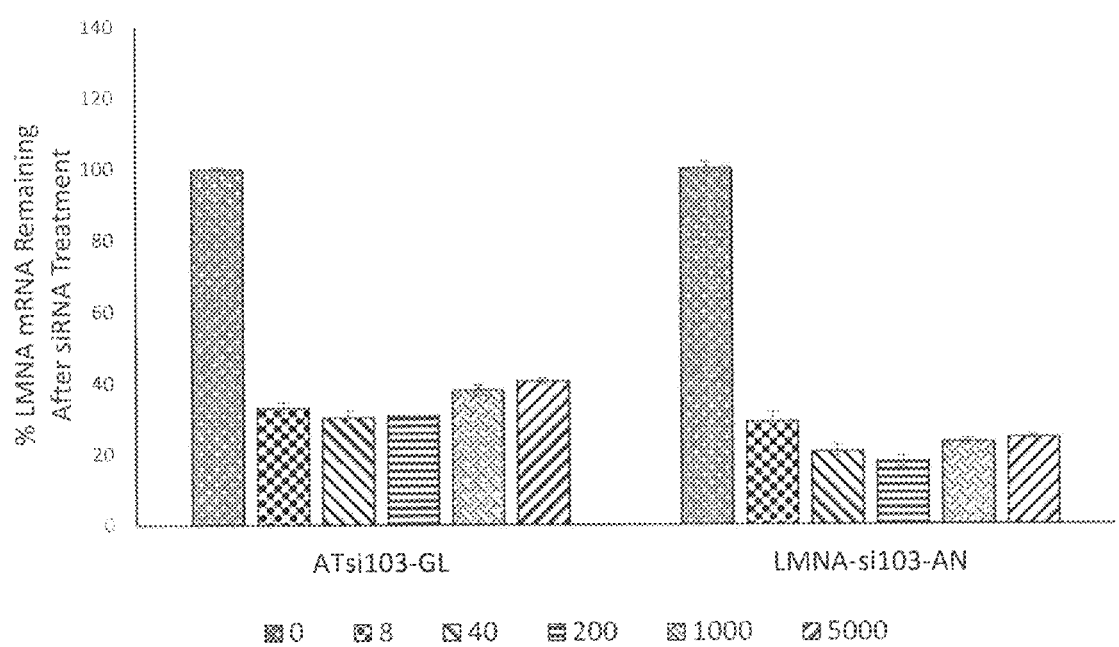
FIGURE 3: LMNA mRNA levels in Mouse Hepatocytes (mPH) 60 hours after free uptake of GalNAc conjugated siRNAs at different doses (μM).

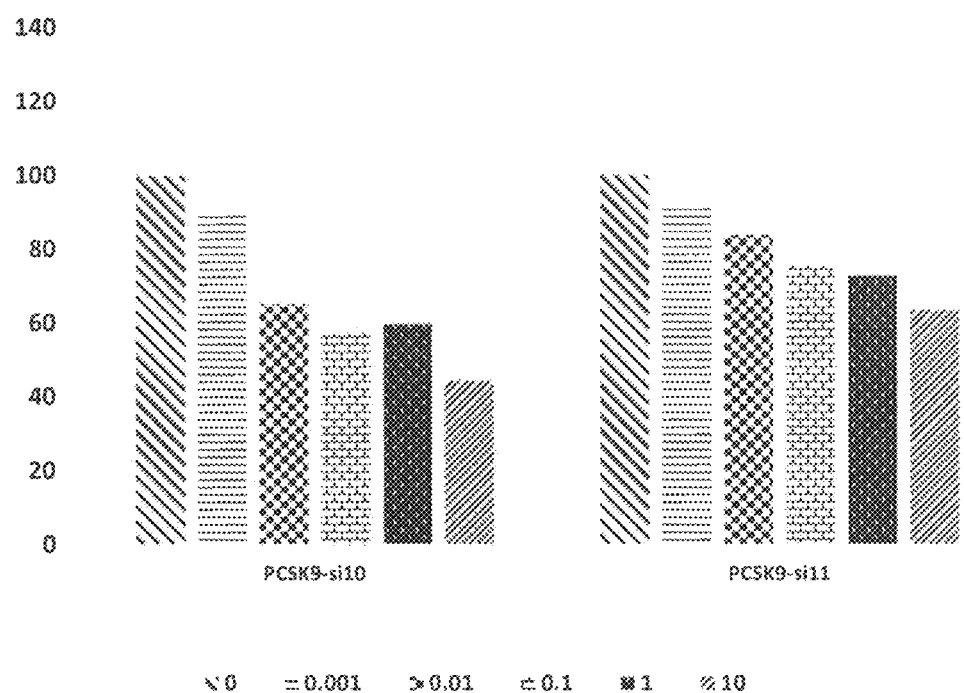
FIGURE 4: PCSK9 mRNA levels in Human Primary Hepatocytes (HPH) 4 days after free uptake of GalNAc conjugated siRNAs at different doses (μM).

ARNATAR COMPOUNDS AND METHODS FOR ENHANCED CELLULAR UPTAKE

CROSS-REFERENCE TO RELATED APPLICATIONS

This subject application is a continuation application under 35 U.S.C. § 111a of, and claims priority to, PCT Application No. PCT/US23/84692, filed Dec. 18, 2023, which claims the benefit of priority to U.S. Provisional Application Nos. 63/433,730, filed on Dec. 19, 2022, 63/533,273, filed on Aug. 17, 2023, and 63/602,245 filed on Nov. 22, 2023, the entire contents of each of said applications are incorporated by reference herein in their entireties.

INCORPORATION BY REFERENCE OF MATERIAL SUBMITTED ELECTRONICALLY

This application contains a Sequence Listing that has been filed electronically in the form of a XML filed computer-readable nucleotide/amino acid sequence listing submitted concurrently herewith and identified as follows: 73,668 bytes ASCII the text file named "GalNac_sequence_ listing.xml", which was created on Dec. 18, 2023, the entirety of which is hereby incorporated by reference.

Throughout this application various publications are referenced. All publications, gene transcript identifiers, patents, and patent applications mentioned in this specification are herein incorporated by reference to the same extent as if each individual publication, gene transcript identifiers, patent, or patent application was specifically and individually indicated to be incorporated by reference.

FIELD

This invention generally relates to the field of compounds and methods for enhanced cellular uptake. In particular, the present invention relates to N-acetylgalactosamine compounds and their conjugates. Also provided are methods for the preparation of these molecules and uses thereof, in particular in medicine.

BACKGROUND

Pharmaceutical agents such as oligomeric compounds (e.g., oligonucleotides) require entry into target cells to become active. A variety of modalities have been used to traffic oligomeric compounds into target cells including viral delivery vectors, lipid-based delivery, polymer-based delivery, and conjugate-based delivery (Paunovska et al., Drug Delivery Systems for RNA Therapeutics, 2022, Nature Reviews Genetics, 23(5):265-280; Chen et al., 2022, Molecular Therapy, Nucleic Acids, 29:150-160).

Conjugation of N-acetylgalactosamine (GalNAc) compounds to oligomeric compounds has become a major delivery strategy to deliver oligomeric compounds into cells such as hepatocytes. Various GalNAc compound conjugates have been previously described in the literature, including the following, all of which are incorporated-by-reference herein: Sharma et al., 2018, Bioconjugate Chem, 29:2478-2488; Nair et al., 2014, J. Am. Chem. Soc. 136(49):16958-16961; Keam, 2022, Drugs, 82:1419-1425; U.S. Pat. No. 10,087,208; Prakash et al., 2014, Nucleic Acids Res, 42(13): 8796-807; Debacker et al., 2020, Molecular Therapy, 28(8): 1759-1771; Huang et al., 2017, Bioconjugate Chem, 28:283-295; Nair et al., 2017, Nucleic Acids Res, 45(19):10969-10977; U.S. Pat. Nos. 11,110,174; 9,796,756; 9,181,549; 10,344,275; 10,570,169; 9,506,030; 7,582,744; 8,106,022; 11,692,001; WO 2022162161; WO 2022162154; WO 2022136466; WO 2021257917; and WO 2021257916.

Several oligomeric compounds with various types of GalNAc compound conjugates have received U.S. Food and Drug Administration (FDA) approval (Moumné et al, Oligonucleotide Therapeutics: From Discovery and Development to Patentability, Pharmaceutics, 2022, 14(2):260; Friedrich and Aigner, Therapeutic siRNA: State-of-the-Art and Future Perspectives, 2022, BioDrugs, 36(5):549-571; Hu et al., Therapeutic siRNA: State of the Art, Signal Transduction and Targeted Therapy, 2020, 5:101). However, improved GalNAc compounds for conjugation to pharmaceutical agents are still being sought.

SUMMARY

The present invention generally relates to novel GalNAc compounds for conjugation to pharmaceutical agents, to the GalNAc compound conjugates as well as to their production processes and applications.

In one aspect, the present invention relates to a compound having the structure of formula (0):

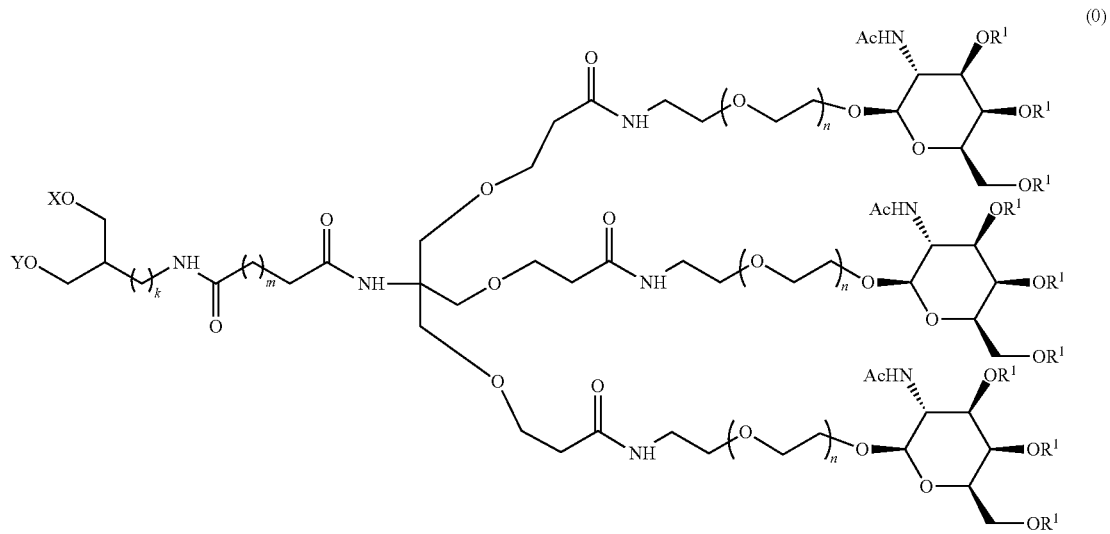

wherein
  k is an integer from 1 to 5,
  m is an integer from 0 to 11,
  n is an integer from 0 to 5,
  X is a hydroxy-protecting group or an H atom,
  Y is a hydroxy-protecting group, an H atom, a payload, or a solid support, wherein the payload or the solid support are optionally connected via a spacer, and
  $R^1$ is independently selected from hydroxy-protecting groups and H atom.

In one aspect, the present invention relates to a process for the preparation of a compound having the structure of formula (0):

wherein
  k is an integer from 1 to 5, preferably 3,
  $R^2$ represents an amino-protecting group or an H atom,
  $R^3$ represents a solid support, optionally connected via a spacer, a hydroxy-protecting group, or an H atom, and
  $R^6$ represents a hydroxy-protecting group, preferably dimethoxytrityl (DMT) or monomethoxytrityl (MMT), more preferably MMT.

In another aspect, the present invention relates to a compound having the structure of formula (III):

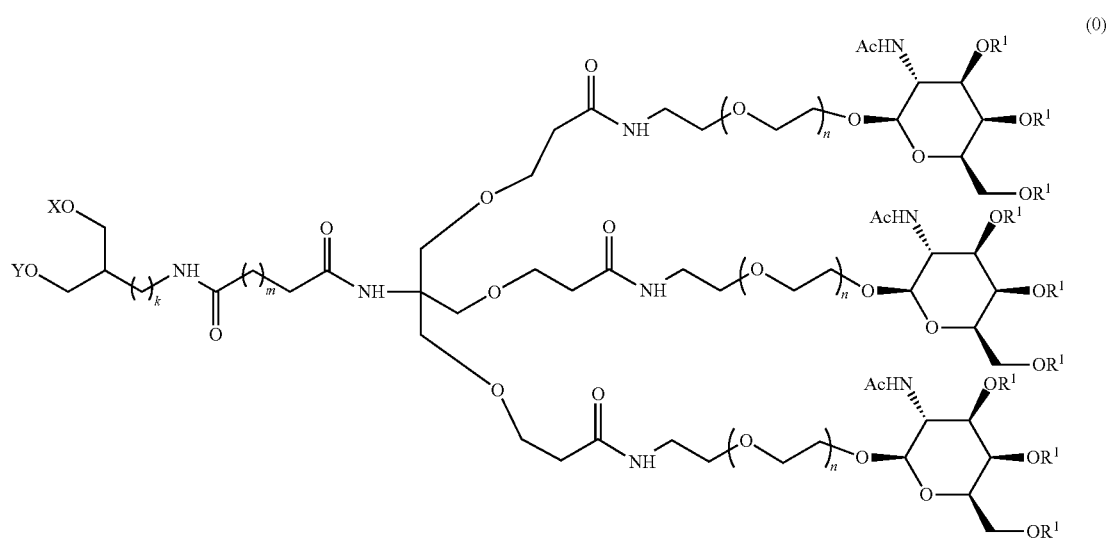

(0)

wherein
  k is an integer from 1 to 5,
  m is an integer from 0 to 11,
  n is an integer from 0 to 5,
  X is a hydroxy-protecting group or an H atom,
  Y is a hydroxy-protecting group, an H atom, a payload, or a solid support, wherein the payload or the solid support are optionally connected via a spacer, and
  $R^1$ is independently selected from hydroxy-protecting groups and H atom,
comprising the step of reacting the compound having the structure of formula (III):

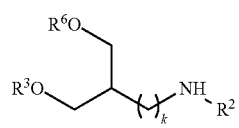

(III)

wherein
  k is an integer from 1 to 5,
  $R^2$ represents an amino-protecting group or an H atom,
  $R^3$ represents a solid support, optionally connected via a spacer, or a hydroxy-protecting group, or an H atom, and
  $R^6$ represents a hydroxy-protecting group, preferably DMT or MMT, more preferably MMT.

This compound is used in some embodiments of the present invention in the preparation of the compound of formula (0).

In one further aspect, the present invention relates to a compound having the structure of formula (0):

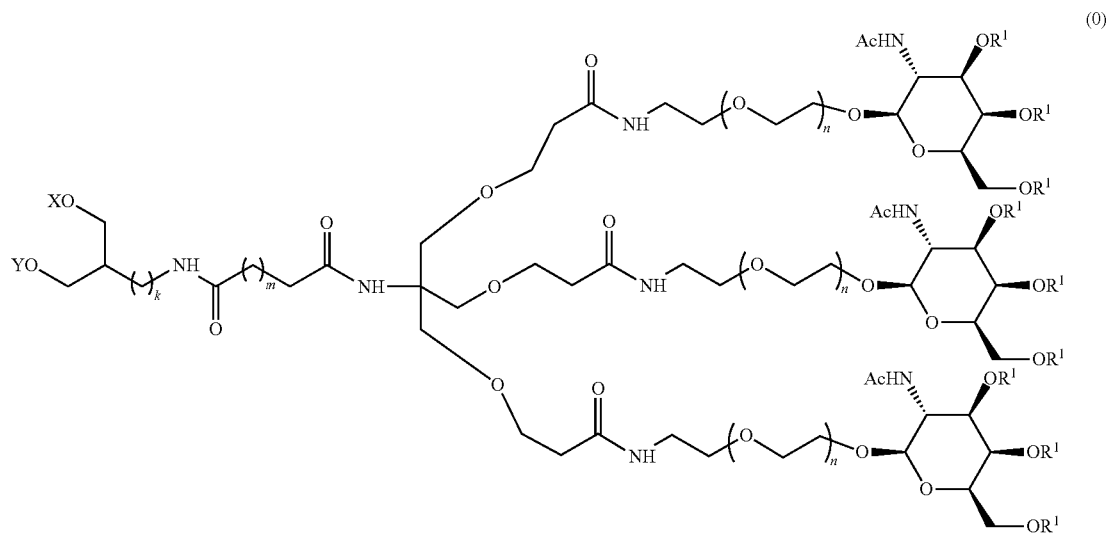

(0)

wherein
  k is an integer from 1 to 5,
  m is an integer from 0 to 11,
  n is an integer from 0 to 5,
  X is an H atom,
  Y is a payload optionally connected via a spacer, and
  $R^1$ is an H atom,
for use in medicine. In one related aspect, the present invention relates to this compound for use in a method of treating a subject with the payload, the subject comprising cells expressing asialoglycoprotein receptor (ASGPR).

In one aspect, the present invention relates to a method for transporting a payload into a cell expressing asialoglycoprotein receptor (ASGPR) comprising the step of administering a compound having the structure of formula (0):

wherein
  k is an integer from 1 to 5,
  m is an integer from 0 to 11,
  n is an integer from 0 to 5,
  X is an H atom,
  Y is a payload optionally connected via a spacer, and
  $R^1$ is an H atom,
wherein the payload is transported into the cell expressing asialoglycoprotein receptor (ASGPR) in the subject in an amount sufficient to treat the subject with the payload.

In another aspect, the present invention relates to a pharmaceutical composition comprising a compound having the structure of formula (0):

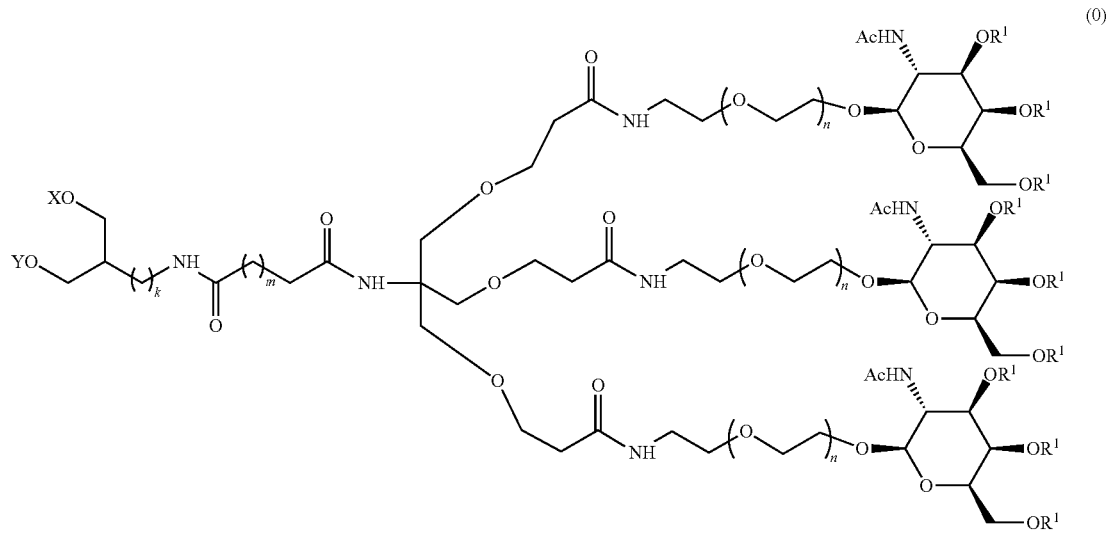

(0)

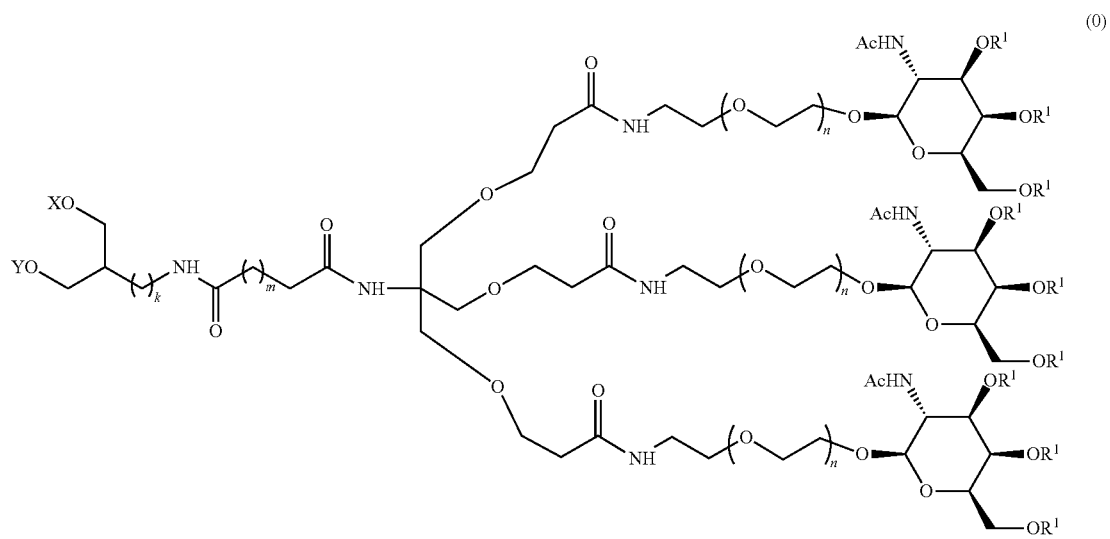

wherein
k is an integer from 1 to 5,
m is an integer from 0 to 11,
n is an integer from 0 to 5, preferably 3,
X is an H atom,
Y is a payload optionally connected via a spacer, and
$R^1$ is an H atom,
and a pharmaceutically acceptable carrier, excipient, and/or diluent.

Kits and pharmaceutical compositions comprising the compounds of the invention, including methods for making and using, are moreover contemplated.

BRIEF DESCRIPTION OF THE DRAWINGS

FIG. 1: shows LMNA mRNA levels in Human Primary Hepatocytes (hPH) 51 hours after free uptake of GalNAc conjugated siRNAs at different doses (μM).

FIG. 2: shows LMNA mRNA levels in Human Primary Hepatocytes (hPH) over time after free uptake of GalNAc conjugated siRNAs (5 μM).

FIG. 3: shows LMNA mRNA levels in Mouse Hepatocytes (mPH) 60 hours after free uptake of GalNAc conjugated siRNAs at different doses (μM).

FIG. 4: shows PCSK9 mRNA levels in Human Primary Hepatocytes (HPH) 4 days after free uptake of GalNAc conjugated siRNAs at different doses (μM).

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well-known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated-by-reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxyethyl modification at the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety. "2'-MOE nucleotide" (also 2'-O-methoxyethyl nucleotide) means a nucleotide comprising a 2'-MOE modified sugar moiety.

"2'-O-methyl" (also 2'-OCH$_3$ and 2'-OMe) refers to an O-methyl modification at the 2' position of a furanose ring. A 2'-O-methyl modified sugar is a modified sugar.

"2'-OMe nucleoside" (also 2'-OMe nucleoside) means a nucleoside comprising a 2'-OMe modified sugar moiety. "2'-OMe nucleotide" (also 2'-O-methyl nucleotide) means a nucleotide comprising a 2'-OMe modified sugar moiety.

"2'-substituted nucleoside" means a nucleoside comprising a substituent at the 2'-position of the furanosyl ring other than H or OH. In certain embodiments, 2' substituted nucleosides include nucleosides with a fluoro (2'-F), O-methyl (2'-OMe), O-methoxyethyl (2'-MOE) or bicyclic sugar modifications.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of mRNA", it is implied that the mRNA levels are inhibited within a range of 63% and 77%.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any antigen-binding fragment or region thereof. Examples of such antigen-binding fragment or region include the heavy chain, the light chain, $F_{ab}$ region, and $F_c$ region of an antibody.

"Antisense oligonucleotide" or "ASO" means a single-stranded oligonucleotide having a nucleobase sequence that permits hybridization to a corresponding region or segment of a target nucleic acid. In certain embodiments, the antisense oligonucleotide comprises one or more ribonucleosides (RNA nucleosides) and/or deoxyribonucleosides (DNA nucleosides). Antisense oligonucleotides can be modified; examples of such modifications include 5-methylcytosine and 2'-MOE.

"Base complementarity" refers to the capacity for the base pairing of nucleobases of an oligonucleotide with corresponding nucleobases in a target nucleic acid (i.e., hybridization), and is mediated by Watson-Crick, Hoogsteen or reversed Hoogsteen hydrogen binding between corresponding nucleobases. Base complementarity also refers to canonical (e.g., A:U, A:T, or C:G) or non-canonical base pairings (e.g., A:G, A:U, G:U, I:U, I:A, or I:C).

"Bicyclic sugar" means a furanose ring modified by the bridging of two non-geminal carbon, atoms. A bicyclic sugar is a modified sugar.

"Cap structure" or "terminal cap moiety" means chemical modifications, which have been incorporated at either terminus of an oligomeric compound.

"Chemical modification" means modification of molecular structure or element from naturally occurred molecules. For example, siRNA compounds are composed of linked ribonucleosides (also sometimes referred to herein as RNA), therefore, substitution of a deoxyribonucleoside (also sometimes referred to herein as DNA) for a ribonucleoside is considered a chemical modification of the siRNA compound.

"Chemically distinct region" refers to a region of an oligomeric compound that is in some way chemically different than another region of the same oligomeric compound. For example, a region having 2'-OMe nucleotides is chemically distinct from a region having nucleotides without 2'-OMe modifications.

"Chimeric oligomeric compounds" means oligomeric compounds that have at least 2 chemically distinct regions, each position having a plurality of subunits. For example, as disclosed herein, siRNA can comprise a peripheral region and a central region. The peripheral region comprise motifs with various modified or unmodified nucleobases so as to confer increased stability, specificity, safety and potency, while the central region comprises various modified or unmodified nucleobases to serve as substrate for RISC mediated degradation.

"Complementarity" means the capacity for pairing between nucleobases of a first nucleic acid and a second nucleic acid.

"Comply" means the adherence with a recommended therapy by an individual.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxyribonucleoside" means a nucleoside having a hydrogen at the 2' position of the sugar portion of the nucleoside. A deoxyribonucleoside is sometimes referred to as DNA nucleoside, "D" or "d" herein. Deoxyribonucleosides may be modified with any of a variety of substituents and may be connected by covalent linkages other than naturally occurring phosphodiester such as phosphorothioate.

"Deoxyribonucleotide" means a nucleotide having a hydrogen at the 2' position of the sugar portion of the nucleotide. A deoxyribonucleotide is sometimes referred to as DNA nucleotide, "D" or "d" herein. Deoxyribonucleotides may be modified with any of a variety of substituents and may be connected by covalent linkages other than naturally occurring phosphodiester such as phosphorothioate.

"Designing" or "Design" refer to the process of designing an oligomeric compound that specifically hybridizes with a target nucleic acid molecule.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an oligomeric compound and a target nucleic acid is a second nucleic acid.

"Fully modified motif" refers to an oligomeric compound comprising a contiguous sequence of nucleosides wherein essentially each nucleoside has a chemical modification.

"GalNAc" means "N-acetylgalactosamine". Accordingly, "GalNAc compound" means a compound comprising one or more N-acetylgalactosamine units.

"Hybridization" means the annealing of complementary nucleic acid molecules. In certain embodiments, complementary nucleic acid molecules include, but are not limited to, an oligomeric compound and a nucleic acid target. In certain embodiments, complementary nucleic acid molecules include, but are not limited to, a siRNA and a nucleic acid target.

"Immediately adjacent" means there are no intervening elements between the immediately adjacent elements.

"Individual" means a human or non-human animal selected for treatment or therapy.

"Induce", "inhibit", "potentiate", "elevate", "increase", "decrease" or the like, generally denote quantitative differences between two states.

"Inhibiting the expression or activity" refers to a reduction, blockade of the expression or activity and does not necessarily indicate a total elimination of expression or activity.

"Internucleoside linkage" refers to the chemical bond between nucleosides.

"Linked nucleosides" means adjacent nucleosides (e.g., A, G, C, T, or U) linked together by an internucleoside linkage. Examples of linked nucleosides include deoxyribonucleosides (sometimes referred to as DNA nucleosides herein) or ribonucleosides (sometimes referred to as RNA nucleosides herein).

"Mismatch" or "non-complementary nucleobase" refers to the case when a nucleobase of a first nucleic acid is not capable of pairing with the corresponding nucleobase of a second or target nucleic acid through Watson-Crick base-pairing (e.g., A:T, A:U, or C:G).

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase. As used herein, where the oligomeric compound is RNA based, a substitution of a deoxyribonucleoside (sometimes referred to as DNA nucleoside herein) for a ribonucleoside is considered a modification of the oligomeric compound. Also, where the oligomeric compound is DNA based, a substitution of a ribonucleoside (sometimes referred to as RNA nucleoside herein) for a deoxyribonucleoside is considered a modification of the oligomeric compound.

"Modified nucleotide" means a nucleotide having, independently, a modified sugar moiety, modified internucleoside linkage, a deoxyribonucleoside (sometimes referred to as DNA nucleoside herein) for a ribonucleoside (sometimes referred to as RNA nucleoside herein) substitution, a ribonucleoside (sometimes referred to as RNA nucleoside herein) for a deoxyribonucleoside (sometimes referred to as DNA nucleoside herein) substitution, and/or a modified nucleobase.

"Modified oligonucleotide" means an oligonucleotide comprising at least one modified internucleoside linkage, a modified sugar, a deoxyribonucleoside (sometimes referred to as DNA nucleoside herein) for a ribonucleoside (sometimes referred to as RNA nucleoside herein) substitution, a ribonucleoside (sometimes referred to as RNA nucleoside herein) for a deoxyribonucleoside (sometimes referred to as DNA nucleoside herein) substitution, and/or a modified nucleobase.

"Modified sugar" means substitution and/or any change from a natural sugar moiety.

"Moiety" means one of the portions into which something is divided i.e., a part or component of something. For example, a sugar moiety of a nucleotide is the sugar component of the nucleotide.

"Monomer" refers to a single unit of an oligomer. Monomers include, but are not limited to, nucleosides and nucleotides, whether naturally occurring or modified.

"Motif" means the pattern of modification in an oligomeric compound. For example, as disclosed herein, ARNA-TAR designed oligomeric compounds comprising motifs with various modified nucleobases and internucleoside linkages in order to improve delivery, stability, specificity, safety and potency of the compounds.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), messenger RNA (mRNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing (also known as being complementary) with another nucleobase. If a nucleobase at a certain position of an oligomeric compound is capable of hydrogen bonding with a nucleobase at a certain position of a target nucleic acid, then the position of hydrogen bonding between the oligomeric compound and the target nucleic acid is considered to be complementary at that nucleobase pair. For example, in DNA, adenine (A) is complementary to thymine (T); in RNA, adenine (A) is complementary to uracil (U); and, Guanine (G) is complementary to cytosine (C) in both DNA and RNA. Base pairs, or complementary nucleobases, are usually canonical Watson-Crick base pairs (C:G, A:U, or A:T), but, non-canonical base pairs such as Hoogsteen base pairs (e.g., A:G, or A:U), Wobble base pairs (e.g., G:U, I:U, I:A, or I:C, wherein I is hypoxanthine) and the like are also included. Nucleobase complementarity facilitates hybridization of the oligomeric compounds described herein to their target nucleic acids.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a linkage group (e.g., a phosphate (p) or phosphorothioate (PS) group) covalently linked to the sugar portion of the nucleoside. Nucleotides include ribonucleotides and deoxyribonucleotides. Ribonucleotides are the linked nucleotide units forming RNA. Deoxyribonucleotides are the linked nucleotide units forming DNA.

"Off-target effect" refers to an unwanted or deleterious biological effect associated with modulation of RNA or protein expression of a gene other than the intended target nucleic acid.

"Oligomeric activity" means any detectable or measurable activity attributable to the hybridization of an oligomeric compound to its target nucleic acid. In certain embodiments, oligomeric activity is a decrease in the amount or expression of a target nucleic acid or protein encoded by such target nucleic acid. Oligomeric activity can be modulated by an oligomeric compound such as a siRNA.

"Oligomeric compound" means a sequence of linked monomeric subunits that is capable of undergoing hybridization to at least a region of a target nucleic acid through hydrogen bonding. The monomeric subunits can be modified or unmodified nucleotides or nucleosides. The oligomeric compound acts as a template for RISC to recognize complementary messenger RNA (mRNA) transcripts to target a specific mRNA transcript for cleavage. Cleavage of the target mRNA blocks translation of the target mRNA and silences the target gene. Examples of oligomeric compounds include single-stranded and double-stranded compounds, such as, antisense oligonucleotides, ssRNAs, siRNAs, shRNAs and miRNAs.

"Oligomeric inhibition" means reduction of target nucleic acid levels in the presence of an oligomeric compound complementary to a target nucleic acid compared to target nucleic acid levels in the absence of the oligomeric compound.

"Oligomeric mechanisms" include RISC or RNase H related mechanisms involving hybridization of an oligomeric compound with target nucleic acid, wherein the outcome or effect of the hybridization is target degradation and inhibition of gene expression.

"Oligonucleotide" as used herein means a sequence of linked nucleosides each of which can be modified or unmodified, independent one from another. Oligonucleotides can have a linking group other than a phosphate group (e.g., a phosphorothioate=thiophosphate group) used as a linking moiety between nucleosides. In certain embodiments, an oligonucleotide comprises one or more ribonucleosides (RNA nucleosides) and/or deoxyribonucleosides (DNA nucleosides).

"Payload" as used herein means any substance to be transported via a vehicle into the cell, presently the vehicle being the GalNAc compound. In the sense of the presence invention, the "payload" comprises a pharmaceutical agent, i.e., an agent providing for a biological effect in the cell, e.g., leading to therapeutic treatment of a disease or disorder or diagnosis of a disease or disorder. Preferred representatives of payloads are described further below.

"Peptide" as used herein is a compound comprising at least two amino acids linked in a chain, typically by peptide bonds. The peptide may comprise modified amino acids.

"Pharmaceutical agent" as used herein is any compound with pharmaceutical activity, i.e., a compound that is used for therapeutic and/or diagnostic methods.

"Phosphorothioate linkage" or "PS" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Region" is defined as a portion of the target nucleic acid having at least one identifiable structure, function, or characteristic.

"RNA" or "ribonucleic acid" consists of ribose nucleotides or ribonucleotides (nitrogenous bases attached to a ribose sugar) linked by phosphodiester bonds, forming strands of varying lengths. The nitrogenous bases in RNA are adenine, guanine, cytosine, and uracil.

"Ribonucleotide" means a nucleotide having a hydroxy at the 2' position of the sugar portion of the nucleotide. Ribonucleotides can be modified with any of a variety of substituents and may be connected by covalent linkages other than naturally occurring phosphodiester such as phosphorothioate. A ribonucleotide is sometimes referred to as RNA herein.

"Segments" are defined as smaller or sub-portions of regions within a target nucleic acid.

"Sites," as used herein, are defined as unique nucleobase positions within a target nucleic acid.

"Specifically hybridizable" refers to an oligomeric compound having a sufficient degree of complementarity between an oligomeric compound (e.g., siRNA) and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment, diagnosis or therapy.

"Target" refers to a protein or nucleic acid sequence (e.g., mRNA), the modulation of which is desired.

"Target gene" refers to a gene encoding a target.

"Targeting" means the process of design and selection of an oligomeric compound that will specifically hybridize to a target nucleic acid and induce a desired effect.

"Target nucleic acid," "target RNA," "target RNA transcript" and "nucleic acid target" all mean a nucleic acid capable of being targeted by oligomeric compounds.

"Target region" means a portion of a target nucleic acid to which one or more oligomeric compounds is targeted.

"Target segment" means the sequence of nucleotides of a target nucleic acid to which an oligomeric compound is targeted. "5' target site" refers to the 5'-most nucleotide of a target segment. "3' target site" refers to the 3'-most nucleotide of a target segment. In an embodiment, a target segment is at least a 12-nucleobase portion (i.e., at least 12 consecutive nucleobases) of a target region to which an oligomeric compound is targeted.

"Therapeutic efficacy" refers to the effectiveness of a therapeutic compound such as an oligomeric compound. Therapeutic efficacy can be increased by improvements in delivery, stability, specificity, safety and potency of the therapeutic compound.

"Unmodified" RNA nucleobases mean the purine bases adenine (A) and guanine (G), and the pyrimidine bases cytosine (C) and uracil (U). "Unmodified" DNA nucleobases mean the purine bases adenine (A) and guanine (G), and the pyrimidine bases thymine (T) and cytosine (C). In certain embodiments, an unmodified RNA nucleobase is considered modified when a DNA nucleobase is substituted for the RNA nucleobase. In certain embodiments, an unmodified DNA nucleobase is considered modified when a RNA nucleobase is substituted for the DNA nucleobase.

"Unmodified nucleotide" means a nucleotide composed of naturally occurring nucleobases, sugar moieties, and internucleoside linkages. In certain embodiments, an unmodified nucleotide is an RNA nucleotide or a DNA nucleotide.

Subject-Matter of the Present Invention

The present invention provides novel N-acetylgalactosamine-containing compounds (i.e., GalNAc compounds) for an enhanced cellular uptake. Interestingly and fully unexpected, it has been found that—when conjugated to a payload such as an oligonucleotide—the novel GalNAc compounds provide enhanced activity in a cell compared to prior art GalNAc compounds of very close structure.

This invention also provides novel methods for the preparation of the novel GalNAc compounds as well as intermediate compounds that are very suitable in the novel methods.

Moreover, the present invention also provides possible uses and methods of the novel GalNAc compounds, in particular in medicine.

GalNAc Compounds

In one aspect, the present invention relates to a compound having the structure of formula (0):

wherein
- k is an integer from 1 to 5, preferably 2 or 3, more preferably 3,
- m is an integer from 0 to 11, preferably 7 to 9, more preferably 7, and
- n is an integer from 0 to 5, preferably 2 or 3, more preferably 3,
- X is a hydroxy-protecting group or an H atom,
- Y is a hydroxy-protecting group, an H atom, a payload or a solid support, wherein the payload or the solid support are optionally connected via a spacer, and
- $R^1$ is independently selected from hydroxy-protecting groups and H atom.

The compound (0) comprises a trimeric unit comprising N-acetylgalactosamine (GalNAc) units. In the compounds of the present invention, the cyclic sugar moiety is based on D-Galactose, i.e. (2R,3S,4S,5R)-2,3,4,5,6-pentahydroxyhexanal. Depending on the selection of the residues X, Y and $R^1$, compound (0) may either be the GalNAc compound conjugate with a payload (such as compound (I)) or an intermediate GalNAc compound (such as compound (II)) for the synthesis of a GalNAc compound conjugate. The wording "GalNAc compound" as used herein encompasses both the GalNAc compound conjugate with a payload and an intermediate GalNAc compound.

The GalNAc units are connected via a linker that comprises three variable parts, which may comprise a different number of repetitions of —$CH_2$— groups or —$OCH_2$— groups, indicated as integers k, m or n, respectively. Hereby, k is an integer from 1 to 5, preferably 2 or 3, more preferably 3; m is an integer from 0 to 11, preferably 7 to 9, more preferably 7; and n is an integer from 0 to 5, preferably 2 or 3, more preferably 3. In one embodiment, the sum of k and m is an integer from 8 to 12, preferably 10. A linker of such a length has been found to be particularly useful in the GalNAc compound. In one preferred embodiment, k is 3, m is 7 and n is 3, and the compound has the structure of formula (0a):

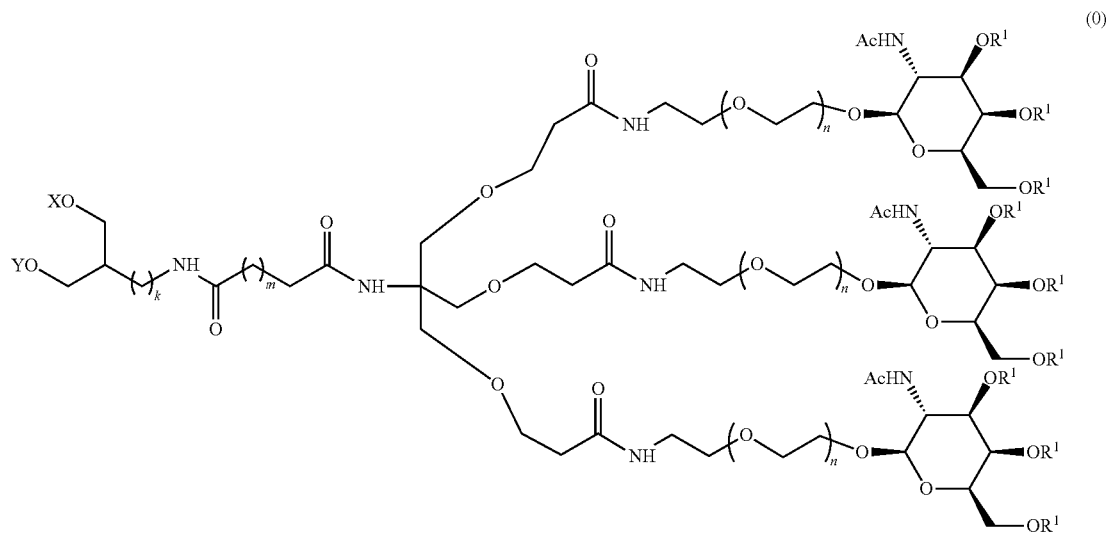

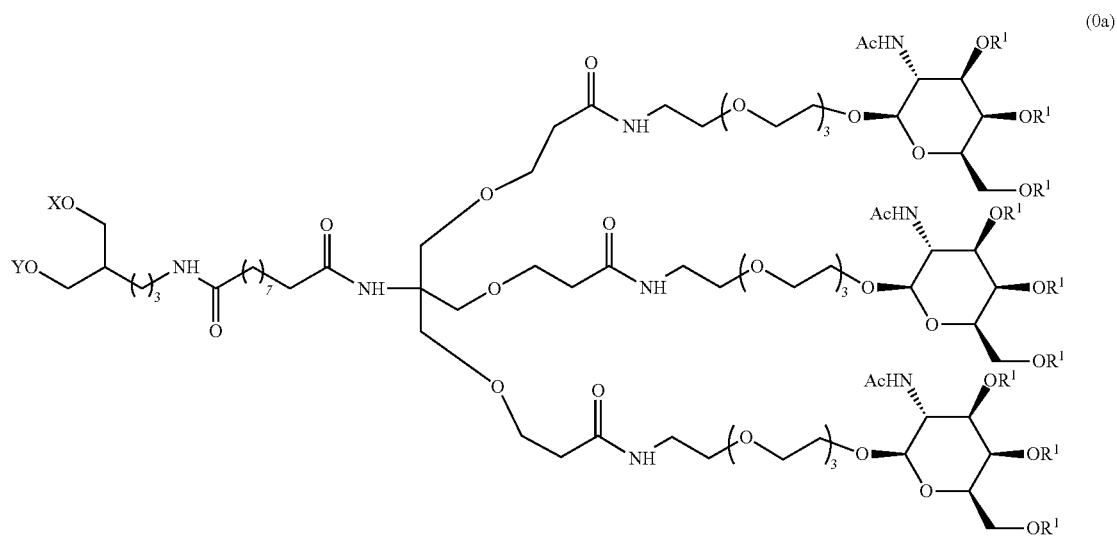

(0a)

In the compound (0) and/or (0a), the residues X, Y and $R^1$ may represent hydroxy-protecting groups or an H (hydrogen) atom. The residues may be selected independently from all possible hydroxy-protecting groups and the H atom. Preferred hydroxy-protecting groups comprise acetyl, benzoyl, phenoxy-acetyl, pivaloyl, monomethoxytrityl (MMT), dimethoxytrityl (DMT), isobutyryl, t-butyldimethylsilyl, t-butyldiphenylsilyl, triisopropylsilyl and isopropyldimethylsilyl. Preferred hydroxy-protecting groups are acetyl for residue $R^1$ and/or monomethoxytrityl (MMT) or dimethoxytrityl (DMT) for residue X. These groups have been found particularly useful in the synthesis of the GalNAc compound of the present invention and coupling of the payload to the intermediate GalNAc compound. In particular, MMT will be useful for the oligonucleotide synthesis. Due to the symmetry of the —$CH_2OX$ and —$CH_2OY$ groups, the formulas include these groups regardless of their preparation process. However, it is to be understood that if a solid support is present as Y residue, the oligonucleotide will be attached to the other residue, i.e., the X residue.

Each of residues X and $R^1$ may represent an H atom. In one embodiment of the GalNAc compound conjugate with a payload, it is preferred that the X and $R^1$ residues each are H atoms.

The residue Y may also be a payload or a solid support, optionally connected via a spacer.

In one embodiment, the residue Y is a payload. In this embodiment, the GalNAc compound may be the final conjugate for introduction into a cell or therapeutic use. As defined above, a payload is any substance to be transported via a vehicle into the cell, presently the vehicle being the GalNAc compound. In the sense of the present invention, the payload comprises a pharmaceutical agent, i.e., an agent providing for a biological effect in the cell e.g., leading to therapeutic treatment of a disease or disorder, or diagnosis of a disease or disorder. Preferred payloads in the present invention comprise an oligomeric compound including any oligonucleotide (i.e., modified or unmodified), a peptide, an antibody, an antibody fragment, or a chemical compound having pharmaceutical activity. It is to be understood that each of these compounds may be conjugated to the (intermediate) GalNAc compound either directly or via a spacer suitable for conjugation of the respective compound. Thus, a payload within the meaning of the present invention may include a spacer, even if not explicitly indicated.

In some embodiments, the payload comprises an oligomeric compound, preferably an oligonucleotide. Oligomeric compounds include, but are not limited to, single stranded oligomeric compounds such as microRNAs (miRNAs), single stranded RNAs (ssRNA) and antisense oligonucleotides (ASOs); and double stranded oligomeric compounds such as short hairpin RNAs (shRNAs) and small interfering RNAs (siRNAs). An oligomeric compound may be "antisense" or comprise an "antisense strand" to a target nucleic acid, meaning that is capable of undergoing hybridization to a target nucleic acid through hydrogen bonding.

In certain embodiments, an oligomeric compound has a nucleobase sequence that, when written in the 5' to 3' direction, comprises the reverse complement of the target segment of a target nucleic acid to which it is targeted. For example, in certain such embodiments, a siRNA comprises an antisense strand which has a nucleobase sequence that, when written in the 5' to 3' direction, comprises the reverse complement of the target segment of a target nucleic acid to which it is targeted.

In certain embodiments, an oligomeric compound is 12-30 subunits (e.g., nucleotides or nucleosides) in length. In certain embodiments, an oligomeric compound is 18 to 30 subunits in length. In certain embodiments, an oligomeric compound is 12 to 22 subunits in length. In some embodiments the oligomeric compound is a siRNA.

It is possible to increase or decrease the length of an oligomeric compound, such as an siRNA, and/or introduce base mismatch(es) without eliminating activity (U.S. Pat. No. 7,772,203, incorporated-by-reference herein). For example, it is possible to introduce non-canonical base pairings (e.g., A:G, A:C, G:U, 1:U, 1:A, or 1:C) into an oligomeric compound without eliminating activity. In certain embodiments, designing oligomeric compounds with one or more non-canonical base pairings, i.e., mismatch(es), enhances the activity of the oligomeric compound.

The oligomeric compound can comprise a mismatch(es) with the target, between the oligomeric strands within the duplex, or combinations thereof. The mismatch may occur throughout the siRNA such as in the overhang region or the duplex region.

In several embodiments, the oligomeric compound is single-stranded (e.g., a single stranded oligonucleotide, a single stranded RNA (ssRNA)) or double-stranded (e.g., shRNA and siRNA), and is modified. The single-stranded oligomeric compound comprises a sense strand or an antisense strand. The double-stranded oligomeric compound comprises a sense strand and an antisense strand. The antisense strands can be fully or partially complementary to a target nucleic acid.

The oligomeric compound, preferably oligonucleotide, may generally be a modified and/or unmodified compound. A nucleoside is a base-sugar combination. The nucleobase (also known as base) portion of the nucleoside is normally a heterocyclic base moiety. Nucleotides are nucleosides that further include a covalent linkage (e.g., phosphate group or a chemically modified linkage as described infra) to the sugar portion of the nucleoside. Oligonucleotides are formed through the covalent linkage of adjacent nucleotides to one another, to form a linear polymeric oligonucleotide. Within the oligonucleotide structure, the linkage groups are commonly referred to as forming the internucleoside linkages of the oligonucleotide. Oligomeric compounds are made up of one (e.g., ssRNAs, antisense oligonucleotides or miRNAs) or more oligonucleotides (e.g., siRNAs or shRNAs)

Modifications to oligomeric compounds encompass substitutions or changes to nucleobases, internucleoside linkages or sugar moieties. Modified oligomeric compounds are often preferred over native or unmodified forms because of desirable properties such as, for example, enhanced delivery (e.g., increased cellular uptake), enhanced specificity or affinity for a nucleic acid target, increased stability in the presence of nucleases, enhanced safety (e.g., fewer side effects after administration of the compound to a subject) or increased potency (e.g., inhibitory activity).

A modified oligomeric compound, preferable modified oligonucleotide, preferably comprises modified nucleobases or internucleoside linkages. In some embodiments, the oligomeric compound, preferably oligonucleotide, is modified to resist degradation, reduce toxicity and/or enhance activity.

In certain embodiments, oligomeric compounds disclosed herein have chemically modified subunits arranged into motifs to confer on to the oligomeric compounds beneficial properties including, but not limited to: enhanced inhibitory activity to increase potency; increased binding affinity to increase specificity for a target nucleic acid, thereby limiting off-target effects and increasing safety; or enhanced resistance to degradation by in vivo nucleases thereby increasing stability and durability. In certain embodiments, the oligomeric compounds are chimeras where the peripheral nucleobases of the oligomeric compounds comprise motifs with various modified or unmodified nucleobases so as to confer increased stability, specificity, safety and potency, while the central region of the compound comprises various modified or unmodified nucleobases to serve as substrates for RISC mediated degradation. Each distinct region can comprise uniform sugar moieties, modified, or alternating sugar moieties. Each region can comprise a varied pattern of phosphate and phosphorothioate linkages.

In certain embodiments, the sense strand comprises one or more phosphorothioate internucleotide (PS) linkage between 2 nucleosides. In a further embodiment, the sense strand comprises a phosphorothioate internucleotide (PS) linkage adjacent to a deoxyribonucleoside (D) or ribonucleoside (R). The PS linkage can be adjacent to the deoxyribonucleoside (D) or ribonucleoside (R) on the 5' side, the 3' side or both sides. The PS linkage can also be adjacent to 2 nucleosides at the 5' end of the strand and/or 2 nucleosides at the 3' end of the strand. In one embodiment, the oligomeric compound is an ssRNA or siRNA.

The oligomeric compound, preferably oligonucleotide, may be attached via the 3' or 5' end of the strand to the GalNAc compound. In some embodiments, the oligomeric compound, preferably oligonucleotide, is attached via the 3' end of the sense strand to the GalNAc compound. In some embodiments, the oligomeric compound, preferably oligonucleotide, is attached via the 5' end of the sense strand to the GalNAc compound.

In several embodiments, the oligomeric compound is a modified and/or unmodified oligonucleotide. In some embodiments, the oligonucleotide is a modified oligonucleotide that is modified to resist degradation, reduce toxicity and/or enhance activity. Preferably, the modified and/or unmodified oligonucleotide binds to a target nucleotide sequence and modifies expression of a gene encoded by the target nucleotide sequence. In some embodiments, the modified and/or unmodified oligonucleotide inhibits expression of the gene encoded by the target nucleotide sequence, preferably by inhibiting transcription or translation of the target nucleotide sequence. In some embodiments, the target nucleotide sequence of the modified and/or unmodified oligonucleotide is connected with a liver disorder, preferably a metabolic liver disorder, e.g., the target nucleotide sequence of the modified and/or unmodified oligonucleotide encodes a gene associated with a disease which is expressed in the liver, or a gene associated with a liver disorder, preferably a metabolic liver disorder.

In certain embodiments, the oligomeric compound, preferably oligonucleotide, described herein inhibits the expression of a target nucleic acid by at least about 70%, 75%, 80%, 85%, 90%, 95%, 98% or 99%.

Several embodiments are directed to modulating gene expression by oligomeric compound inhibition. In several embodiments, the target nucleotide sequence is a messenger RNA (mRNA).

In certain embodiments, inhibiting laminin (LMNA) gene expression in a cell is intended and comprises administering to the cell an oligomeric compound targeted to an mRNA transcript of LMNA.

In certain embodiments, inhibiting apolipoprotein C3 (ApoC3) gene expression in a cell is intended and comprises administering to the cell an oligomeric compound targeted to an mRNA transcript of ApoC3.

In certain embodiments, inhibiting nucleolin (NCL) gene expression in a cell is intended and comprises administering to the cell an oligomeric compound targeted to an mRNA transcript of NCL.

In some embodiments, hybridization occurs between an oligomeric compound and an mRNA. The most common mechanism of hybridization involves hydrogen bonding (e.g., Watson-Crick, Hoogsteen or reversed Hoogsteen hydrogen bonding) between complementary nucleobases of the nucleic acid molecules.

The GalNAc-payload conjugates according to the present invention may be specifically designed for binding to the asialoglycoprotein receptor (ASGPR). Thus, according to some embodiments, the GalNAc-payload conjugate according to the present invention has a strong affinity for the ASGPR. In relation to the present invention, "strong affinity" means an affinity characterized by an $IC_{50}$ value below 50 nM, preferably 25 nM or less, more preferably 10 nM or less, more preferably 5 nM or less. The $IC_{50}$ is the concentration GalNAc-payload conjugate that inhibits labelled ligand binding to the ASGPR by 50%. The $IC_{50}$ can be determined by the method described in Rensen et al. 2001 Journal of Biological Chemistry Vol 276 pp 37577. In brief, hepatocytes (primary or in culture) are incubated with the ligand $^{125}$I-labelled asialylated orosomucoid (ASOR) at one concentration (e.g., 5 nM) for 2 h at 4° C. in the presence of increasing amounts of the GalNAc-payload conjugates to be investigated. The concentrations could be from 0.2 to 200 nM, at increasing concentrations. The binding of the labelled ASOR is followed in the presence of the GalNAc-payload conjugates to be investigated. Nonspecific binding can be determined in the presence of 100 mM GalNAc. Displacement binding data can be analyzed using a single site binding model and the $IC_{50}$ is calculated.

Asialoglycoprotein receptor (ASGPR) is generally expressed on liver cells. Thus, the GalNAc-payload conjugates according to the present invention are specifically suitable for transportation to liver cells. Thus, the GalNAc-payload conjugates may be particularly designed by the selection of the respective payload for use in the prevention, treatment or diagnosis of a disease or disorder of the liver or by liver-triggered metabolism. In particular, the payload may be designed for the treatment of diseases such as hepatitis (including viral hepatitis, such as HBV or HCV), hepatic steatosis (including metabolic malfunctions), atherosclerosis, hyperlipidemia, hypercholesterolemia, familiar hypercholesterolemia e.g., gain of function mutations in Apolipoprotein B, HDL/LDL cholesterol imbalance, dyslipidemias, e.g., familial hyperlipidemia (e.g., familial combined hyperlipidemia (FCH), familial hypercholesterolemia (FH)), acquired hyperlipidemia, statin-resistant hypercholesterolemia, coronary artery disease (CAD), and coronary heart disease (CHD), acute coronary syndrome (ACS), liver-fibrosis (or disease associated with liver-fibrosis), cirrhosis and cancer. Thus, in some embodiment, the GalNAc-payload conjugates are designed for and/or for use in the treatment of a liver disorder, preferably a metabolic liver disorder.

Asialoglycoprotein receptor (ASGPR) is also expressed on testis cells. Thus, in some embodiments, the GalNAc-payload conjugates are designed for and/or for use in the treatment of a testis disorder.

Asialoglycoprotein receptor (ASGPR) is also expressed on cells other than liver and testis. In some embodiments, the GalNAc-payload conjugates are designed to deliver the GalNAc-payload conjugates into cells expressing ASGPR.

In a preferred embodiment of a GalNAc compound conjugate with a payload, the GalNAc compound has the structure of formula (I):

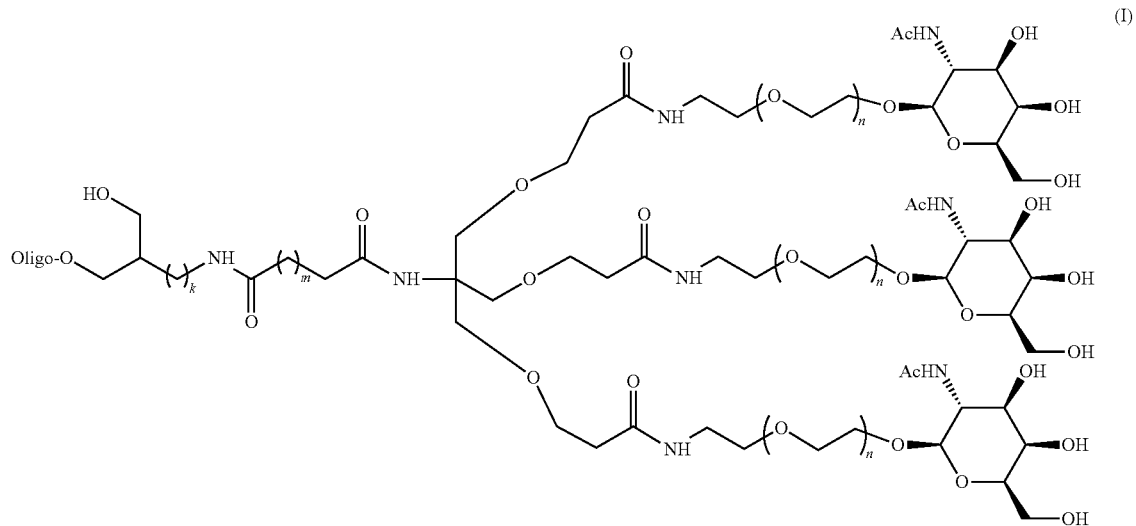

wherein Oligo represents a modified and/or unmodified oligonucleotide, as described above.

In an even more preferred embodiment of a GalNAc compound conjugate with a payload, the GalNAc compound has the structure of formula (Ia):

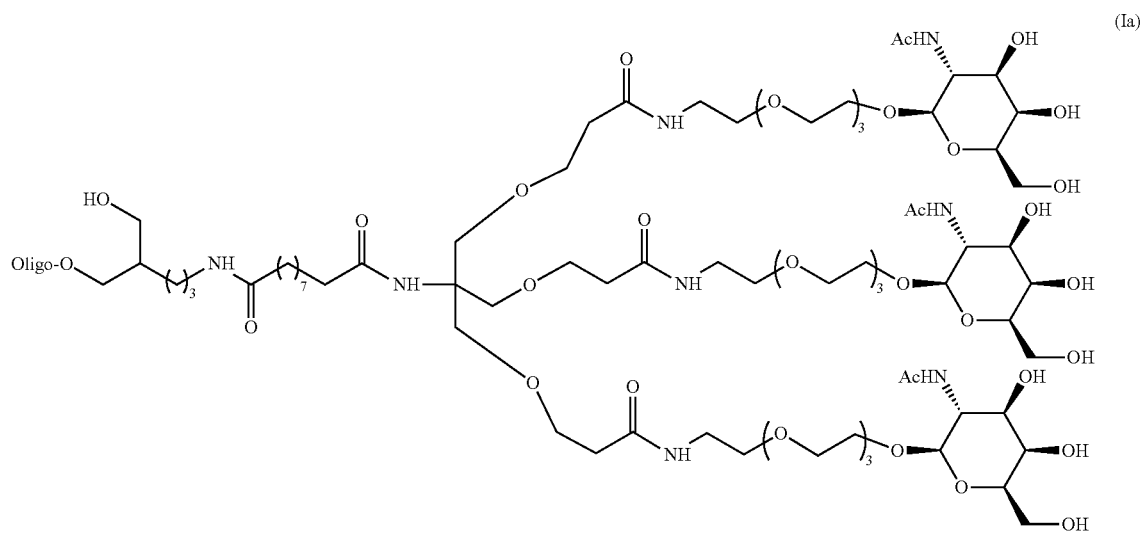

The embodiments of a GalNAc compound conjugate with a payload having the structure of formula (I) or (Ia), may be prepared with any of the features and in any of the embodiments described above.

Besides oligomeric compounds, the payload may comprise a peptide, an antibody, an antibody fragment, or a chemical compound having pharmaceutical activity. Any of the molecules will have—due to the general definition of the payload herein—a pharmaceutical activity. Several drugs based on peptides, antibodies or antibody fragments, or other chemical compounds are known in the art. Generally, it is possible to use the GalNAc compound of the present invention for conjugation to these molecules for transporting into a cell, where these molecules may show their pharmaceutical activity.

In one embodiment, the payload comprises a peptide. Preferably, a peptide comprises a sequence of at least 2 amino acids, such as at least 3 or at least 4 amino acids and more. The amino acids may be natural amino acids and modified amino acids. Modified amino acids are known in the art. In a preferred embodiment, the peptide is an amino acid sequence of a particular protein. A peptide as used herein may encompass a part of a particular protein or the entire amino acid sequence of a particular protein, wherein the amino acids may be modified and/or unmodified. Therapeutic peptides are known in the art and are, e.g., described in Wang et al., Therapeutic peptides: current applications and future directions. Sig Transduct Target Ther 7, 48 (2022), incorporated herein by reference. Examples of therapeutic peptides for the treatment of liver diseases are PGPIPN and FFW as disclosed in Qi et al., Therapeutic hexapeptide (PGPIPN) prevents and cures alcoholic fatty liver disease by affecting the expressions of genes related with lipid metabolism and oxidative stress. Oncotarget. 2017 Sep. 30; 8(50):88079-88093; or National University of Singapore. "Scientists develop novel drug that could potentially treat liver cancer more effectively: Peptide drug FFW shows promise in reducing tumour growth and slowing down spread of cancer cells." ScienceDaily, 2 Aug. 2018. www.sciencedaily.com/releases/2018/08/180802102347.htm. Peptide compounds having potential for use in the treatment of liver fibrosis disclosed Xun et al., Peptide mediated therapy in fibrosis: Mechanisms, advances and prospects, Biomedicine & Pharmacotherapy, Volume 157, 2023, 113978.

In one embodiment, the payload comprises an antibody or an antibody fragment. Antibody fragments are preferably $F_{(ab')2}$, $F_{ab}$, $F_{ab'}$, and $F_v$ fragment that can be generated from variable regions of an antibody (e.g., IgG and/or IgM) and are antigen-binding fragments.

In one embodiment, the payload comprises a chemical compound having pharmaceutical activity. Preferably, the chemical compound is different from the other molecules described as payloads, in that it is a non-peptide compound, a non-oligonucleotide compound and does not contain any antibody or antibody fragment. Typically, the chemical compound is an organic molecule having biological activity, such as so-called "small molecules" used as pharmaceuticals. Suitable compounds for the treatment of liver diseases are, e.g., described in Muriel P, Rivera-Espinoza Y. Beneficial drugs for liver diseases. J Appl Toxicol. 2008 March; 28(2):93-103. doi: 10.1002/jat.1310. PMID: 17966118. Suitable examples are colchicine, corticosteroids, curcumin, glycyrrhizin, interferons, resveratrol, sulfoadenosylmethionine, and thalidomide.

In one embodiment of the compound of formula (0), the residue Y is a solid support, optionally comprising a spacer. In this embodiment, the respective GalNAc compound may be used in the synthesis of the GalNAc compound conjugate. In principle, any solid support known in the art for the attachment of compounds, in particular attachment and solid-phase synthesis of nucleotide sequences, may be used. In certain embodiments, the solid support is a CPG solid support, such as an LCAA (log chain alkyl amine) spacer CPG support. In certain embodiments, the solid support is a polymeric support for solid phase synthesis as known in the art, e.g., polystyrene solid support, such as an aminomethyl polystyrene support. Synthesis on solid-phase support is well known in the art and is described, e.g., in Current Protocols in Nucleic Acid Chemistry (2000) 3.1.1-3.1.28.

In one preferred embodiment, the GalNAc compound is connected to the solid support via a spacer. The spacer may comprise a spacer (2) and/or a spacer (1). The spacer (2) is generally a specific spacer for the particular solid support used. Often, the solid support is already purchased with the spacer (2) attached. It may be e.g., an LCAA (log chain alkyl amine) spacer (as used for CPG support) or a spacer specific for an aminomethyl polystyrene support (often an amine-containing spacer). The spacer (1) may comprise or be a dicarboxylic acid-derived moiety. The dicarboxylic acid-derived moiety may comprise two carboxyl groups or one or both of the carboxyl groups may be modified to amide groups. In particular embodiments, the spacer (1) comprises at least one carboxyl group, and the carboxyl group is reacted with an amine-containing group of the spacer (2) to an amide group. Preferably, the dicarboxylic acid-derived moiety has from 3 to 10 carbon atoms, i.e., it may have from 1 to 8 carbon atoms between the carboxyl and/or amide groups. The 1 to 8 carbon atoms may be linear or branched alkylene having from 1 to 8 carbon atoms (optionally wherein one or more carbon atoms are substituted by an O, S, NH and/or N—($C_1$-$C_3$ alkyl) (i.e., N-methyl, N-ethyl and/or N-propyl)) and/or a cycloalkylene having from 5 to 8 carbon atoms. Preferably, the 1 to 8 carbon atoms are ethylene, 1,1 dimethyl ethylene, propylene, n-butylene or 1,2 cyclohexylene. Preferably, the dicarboxylic acid-derived moiety is derived from succinic acid, 2,2 dimethyl succinic acid, glutaric acid, adipic acid, 1,2 cyclohexane dicarboxylic acid, dimethylene oxide, dimethylene sulfide and/or dimethylene methyl amine. The spacer (1) may be prepared by using the anhydrides of the respective dicarboxylic acids.

Generally, the spacer of the residue Y may be any moiety suitable for its intended function to provide space between two or more units. Preferably, the spacer comprises alkylene moieties, e.g., a $C_{2-10}$ alkylene group, optionally substituted by heteroatoms for facilitated removal of the spacer after reaction of the GalNAc compound with a payload.

The residue Y may also be an H atom or a hydroxy-protecting group, such as any of those defined above. In one embodiment, the residue Y is an H atom. In another embodiment, the residue Y is a hydroxy-protecting group, preferably selected from any of the hydroxy-protecting groups defined above.

In a preferred embodiment, the GalNAc compound used for the synthesis of the GalNAc compound conjugate has the structure of formula (II):

wherein k, m and n are as defined above, $R^1$ is independently selected from hydroxy-protecting groups, as defined above, and H atom, preferably is an acetyl group, $R^1$ represents a hydroxy-protecting group, preferably DMT or MMT, more preferably MMT, and $R^1$ represents a moiety of formula (VI):

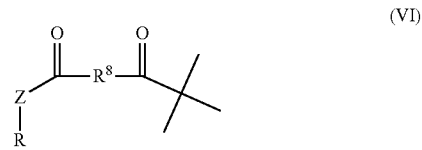

(VI)

wherein

R represents a solid support, optionally connected via a spacer, an amino-protecting group, a hydroxy-protecting group, or an H atom, Z represents NH or O, and $R^8$ represents a linear or branched alkylene having from 1 to 8 carbon atoms, optionally wherein one or more carbon atoms are substituted by any of an O, S, NH and/or N—($C_1$-$C_3$ alkyl) (e.g., N-methyl, N-ethyl and/or N-propyl); and/or a cycloalkylene having from 5 to 8 carbon atoms, preferably being ethylene, 1,1 dimethyl ethylene, propylene, n-butylene, 1,2 cyclohexylene, dimethylene oxide, dimethylene sulfide and/or dimethylene methyl amine.

In some preferred embodiments, $R^7$ represents a moiety of any one of formulas (VIa1) to (VIa8):

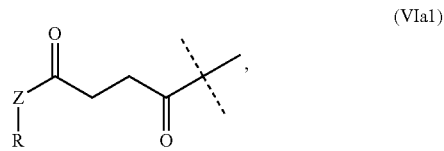

(VIa1)

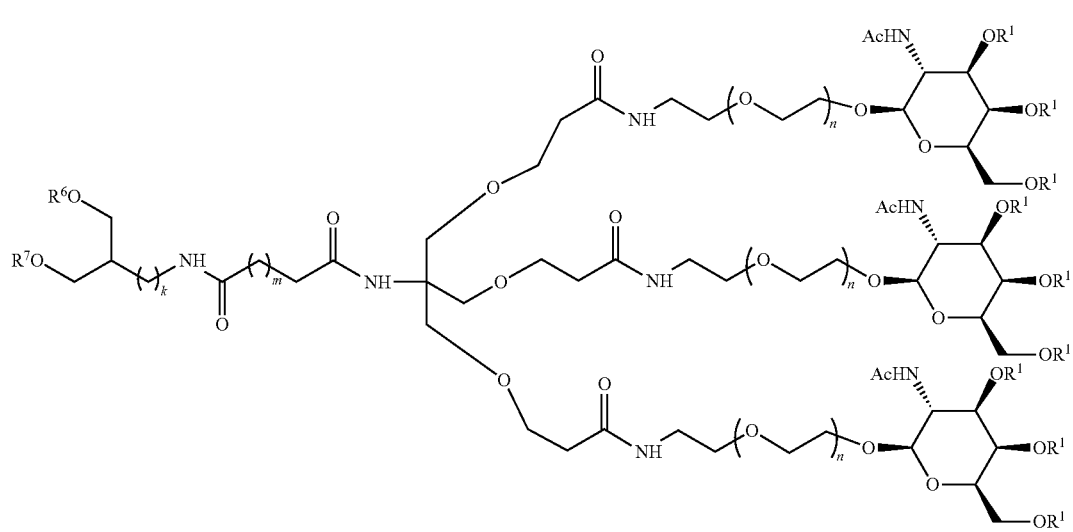

(II)

(VIa2)

(VIa3)

(VIa4)

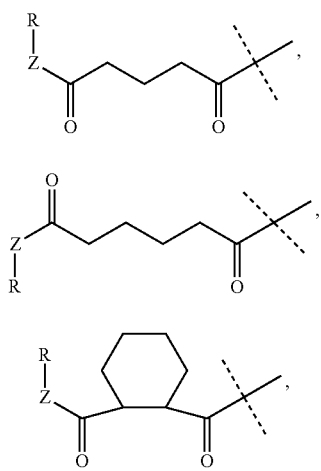

(VIa5)

(VIa6)

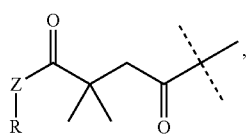

(VIa7)

(VIa8)

In some preferred embodiments, $R^7$ represents a moiety of any one of formulas (VIa3) or (VIa4).

In a further preferred embodiment, the GalNAc compound used for the synthesis of the GalNAc compound conjugate has the structure of formula (IIa):

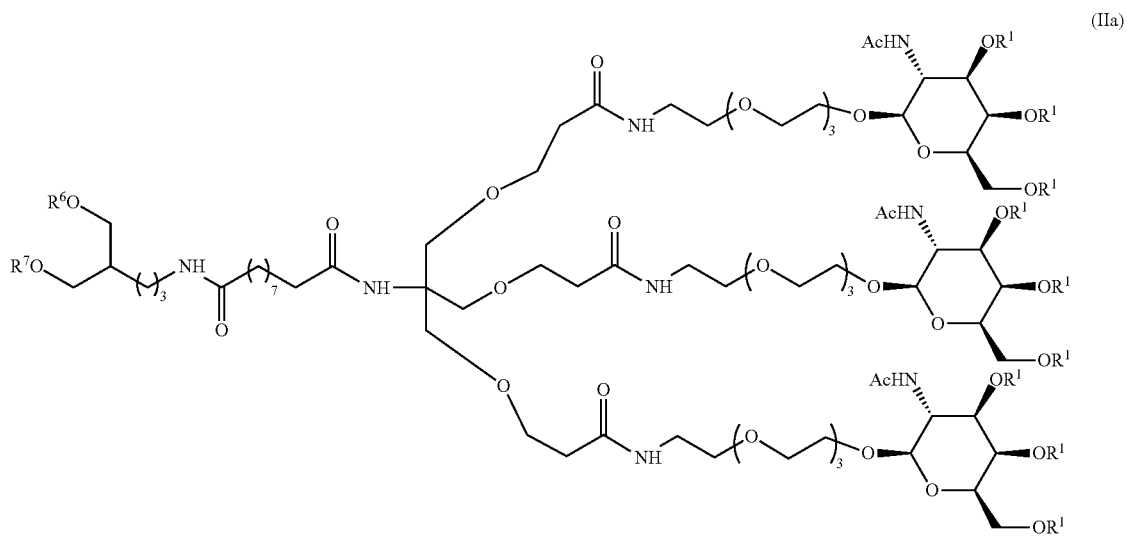

(IIa)

wherein $R^1$, $R^6$ and $R^7$ are as defined above.

In some embodiments of the compound of formula (II) or (IIa), where Z in the moiety $R^7$ represents an NH group, the residue R represents an amino-protecting group, and the amino-protecting group preferably comprises 9-fluorenylmethyl carbamate (Fmoc), t-butyl carbamate (Boc), benzyl carbamate, acetamide, trifluoroacetamide, benzylamine, triphenylmethylamine (tritylamine), p-toluenesulfonamide and/or tosylamide. Although the above wording is used, the skilled person will understand that the residue R together with the N-unit builds the groups as cited above. Use of an amino-protecting group which leads to the formation of phthalimide and benzylideneamine by elimination of the H atom from the N atom is also possible.

In some embodiments of the compound of formula (II) or (IIa), where Z in the moiety $R^7$ represents an O atom, the residue R represents a hydroxy-protecting group, and the hydroxy-protecting group is preferably selected from acetyl, benzoyl, phenoxy-acetyl, pivaloyl, dimethoxytrityl (DMT), monomethoxytrityl (MMT), isobutyryl, t-butyldimethylsilyl, t-butyldiphenylsilyl, triisopropylsilyl and isopropyldimethylsilyl.

In particular embodiments, the residue R in the moiety $R^7$ in the structure of formula (II) and (IIa) is a solid support, optionally connected via a spacer, in particular, a solid support as defined above. The respective (intermediate) GalNAc compounds are particularly suitable for the attachment of nucleotides and, thus, for the preparation of a GalNAc compound conjugate with an oligonucleotide, such as those depicted in the structures of formula (I) and (Ia), respectively.

Compounds for the Preparation of the GalNAc Compounds

In one aspect, the present invention relates to a compound used in the preparation of the GalNAc compounds of the present invention, i.e., to intermediate compounds. In one embodiment, the intermediate compound is a compound having the structure of formula (III):

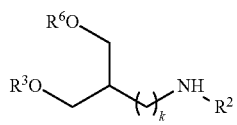
(III)

wherein
- k is an integer as defined above, preferably 3,
- $R^2$ represents an amino-protecting group or an H atom,
- $R^3$ represents a solid support, optionally connected via a spacer, a hydroxy-protecting group, or an H atom, and
- $R^6$ represents a hydroxy-protecting group, preferably DMT or MMT, more preferably MMT.

In some embodiments of the compound of formula (III), the residue $R^2$ represents an amino-protecting group, and the amino-protecting group preferably comprises 9-fluorenylmethyl carbamate (Fmoc), t-butyl carbamate (Boc), benzyl carbamate, acetamide, trifluoroacetamide, benzylamine, triphenylmethylamine (tritylamine), p-toluenesulfonamide and/or tosylamide. Although the above wording is used, the skilled person will understand that the residue $R^2$ together with the N-unit builds the groups as cited above. Use of an amino-protecting group which leads to the formation of phthalimide and benzylideneamine by elimination of the H atom from the N atom is also possible.

In some embodiments of the compound of formula (III), the residue $R^3$ represents a solid support, optionally connected via a spacer, or a hydroxy-protecting group.

In some embodiments of the compound of formula (III), the residue $R^3$ represents a hydroxy-protecting group, which is preferably a hydroxy-protecting group as defined for the X, Y and $R^1$ residues above.

In some particular embodiments of the compound of formula (III), the residue $R^2$ represents an amino-protecting group, preferably 9-fluorenylmethyl carbamate (Fmoc), and/or the residue $R^3$ represents an H atom. In one particular embodiment, the compound of formula (III) has the structure of formula (IIIa):

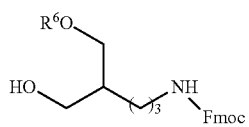
(IIIa)

In some particular embodiments of the compound of formula (III), the residue $R^2$ represents an H atom, and/or the residue $R^3$ represents a solid support, optionally connected via a spacer. In some further particular embodiments, the compound of formula (III) has the structure of any one of formulas (IIIb1) to (IIIb5):

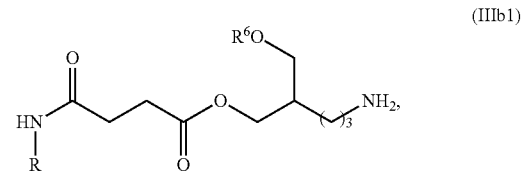
(IIIb1)

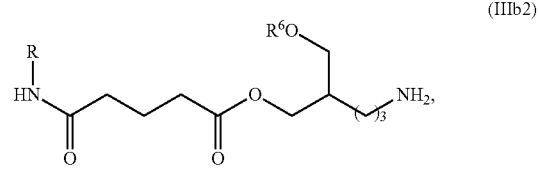
(IIIb2)

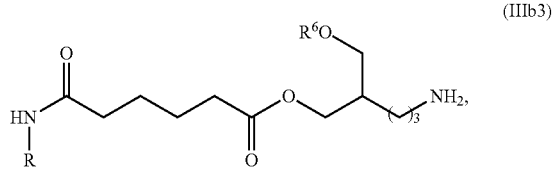
(IIIb3)

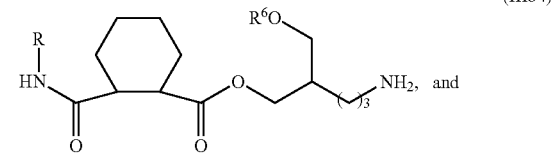
(IIIb4)

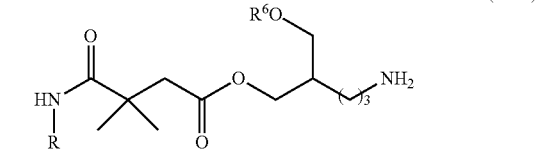
(IIIb5)

wherein
- R represents a solid support, optionally connected via a spacer, an amino-protecting group, or an H atom, and
- $R^6$ represents a hydroxy-protecting group, preferably DMT or MMT, more preferably MMT.

In some particular embodiments, the compound of formula (III) has the structure of any one of formulas (IIIb3) or (IIIb4) as defined above.

In particular embodiments of the compounds of formulas (IIIb1) to (IIIb5), the R residue is a solid support, optionally connected via a spacer, as defined above for the solid support (e.g., as defined for the Y residue).

Processes for the Preparation of GalNAc Compounds

In one aspect, the present invention relates to a process for the preparation of a compound having the structure of formula (0), in any of the above-described embodiments, such as the compound (0a). In some embodiments, the process is a process for the preparation of the compound having the structure of formula (I) and/or (II), in any of the above-described embodiments, such as the compounds (Ia) and/or (IIa).

The process comprises the step of reacting the compound having the structure of formula (III), as defined above. This compound is very suitable as an intermediate compound for the preparation of the GalNAc compound of the present invention.

In some embodiments of the process, the process comprises the step of reacting the compound having the structure of formula (IV):

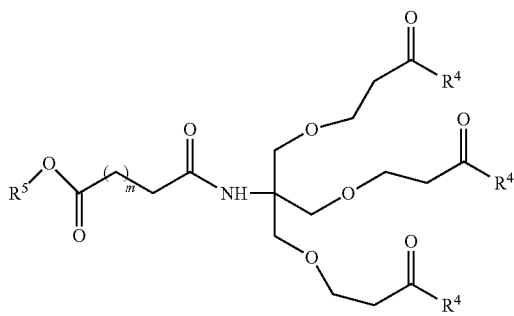
(IV)

wherein
m is an integer as defined above,
$R^4$ represents

F
F F
-O F
F and
$R^5$ represents a hydroxy-protecting group, preferably a benzyl group.

The compound of formula (IV) has been found to be very suitable as further intermediate compound for the preparation of the GalNAc compound of the present invention, and providing high yields of the GalNAc compound.

In some embodiments, the process comprises the steps of:
a) providing a compound having the structure of formula (III):

(III)

wherein
k is an integer as defined above,
$R^2$ represents an H atom,
$R^3$ represents a solid support, optionally connected via a spacer, a hydroxyl-protecting group or an H atom, and
$R^6$ represents a hydroxy-protecting group, preferably DMT or MMT, more preferably MMT;
b) providing a compound having the structure of formula (V):

(V)

wherein
m and n are integers as defined above, and
$R^1$ is independently selected from hydroxy-protecting groups, e.g., as defined above, preferably being acetyl groups; and
c) reacting the compound of formula (III) provided in step a) and the compound of formula (V) provided in step b) to obtain the compound of formula (0), wherein Y is an H atom, a hydroxy-protecting group, or a solid support, optionally connected via a spacer, and X is a hydroxy-protecting group, preferably DMT or MMT, more preferably MMT, or to obtain the compound of formula (II) in any of the embodiments as defined above.

In some embodiments, the process further comprises the step d) of reacting the compound obtained in step c) to obtain the compound of formula (0), wherein Y is a payload and X and $R^1$ each are an H atom, or to obtain the compound of formula (I) in any of the embodiments as defined above. This step may comprise direct addition of a payload or payload precursor, and/or further reaction of the compound obtained in step c) for the addition of an optional linker and a solid support. A payload precursor may be any compound that leads to the attachment of the payload to the (intermediate) GalNAc compound. Due to the symmetry of the —CH$_2$OX and —CH$_2$OY groups, the formulas include these groups regardless of their preparation process. However, it is to be understood that if a solid support is present as Y residue, the payload will be attached to the other residue, i.e., the X residue.

In these embodiments, the residue R$^3$ is preferably as defined above, including the definitions of the solid support and the hydroxy-protecting group for the Y residue above. Preferably, the residue R$^3$ in the compound of formula (0) is identical to the residue R$^3$ of the intermediate compound (III) or is an H atom. More preferably, R$^3$ is identical to R$^1$ and represents a moiety of any one of formulas (VIa1) to (VIa5):

Preferably, the compound (V) is prepared by the use of compound (IV), and is further reacted with the compound of formula (III) provided in step a) of the process.

In particular embodiments, the compound of formula (II) or (IIa) is prepared in step c), and it may be further reacted to a payload-comprising compound such as a compound of formula (I) or (Ia).

In some embodiments of the process, the compound of formula (III) comprises a solid support, i.e., the residue R$^3$ in this compound represents a solid support, optionally connected via a spacer. Thus, the compound (V) is directly reacted to the solid support-comprising compound (III), and the payload may be attached in step d) which is directly subsequent to the reaction of step c). In particular, for the preparation of GalNAc compound conjugates with oligonucleotides, such as those of formula (I) or (Ia), this embodiment of the process is very suitable.

In preferred embodiments, in step d) of the process the compound of formula (I) is formed by addition of modified and/or unmodified nucleotides using standard phosphoramidite chemistry and cleaving the GalNAc compound conjugate from the solid support (as described in the examples section herein). In this way, GalNAc compound conjugates with oligonucleotides are easily provided.

In some embodiments, in step d) of the process the compound of formula (0), wherein Y is a hydroxy-protecting group, an H atom, or a solid support, optionally connected via a spacer, is reacted with a payload or a payload precursor to obtain the compound of formula (0), wherein Y is a payload and X is an H atom.

Applications of the GalNAc Compound Conjugates

In one aspect, the present invention relates to a compound having the structure of formula (0), as defined above, wherein all of the residues X and R$^1$ each are an H atom and the residue Y is a payload, for use in a method of treating a subject or diagnosing a subject with a disease or disorder, the subject comprising cells expressing asialoglycoprotein receptor (ASGPR). The payload may be any payload of the embodiments above.

In some embodiments, the compound for use has the structure of formula (I). In some preferred embodiments, the compound for use has the structure of formula (Ia). In one embodiment, the modified and/or unmodified oligonucleotide in formula (I) or (Ia) binds to a target nucleotide sequence in a hepatocytic cell and modifies expression of a gene encoded by the target nucleotide sequence. Modification of expression is to be understood herein to alter expression by increasing or decreasing the expression rate. In some preferred embodiments, the modified and/or unmodified oligonucleotide inhibits expression of the gene encoded by the target nucleotide sequence.

In one aspect, the present invention relates to a method for transporting a payload into a cell expressing asialoglycoprotein receptor (ASGPR) comprising the step of administering a compound having the structure of formula (0), as defined above, wherein all of the residues X and R$^1$ are H atoms and the residue Y is a payload, wherein the payload is transported into the cell expressing asialoglycoprotein receptor (ASGPR) in the subject in an amount sufficient to treat the subject with the payload. The payload may be any payload of the embodiments above.

In some embodiments of the method, the compound has the structure of formula (I). In some preferred embodiments of the method, the compound has the structure of formula (Ia). In some embodiments of the method, the modified and/or unmodified oligonucleotide in formula (I) or (Ia) binds to a target nucleotide sequence in a hepatocytic cell and modifies expression of a gene encoded by the target nucleotide sequence. Modification of expression is to be understood herein to alter expression by increasing or decreasing the expression rate. In some preferred embodiments of the method, the modified and/or unmodified oligonucleotide inhibits expression of the gene encoded by the target nucleotide sequence. The compound may be administered in any form suitable for administration to subjects. In some preferred embodiments of the method, the compound is administered subcutaneously or intravenously to the subject.

In one aspect, the present invention relates to a pharmaceutical composition comprising a compound having the structure of formula (0), as defined above, wherein all of the residues X and R$^1$ are H atoms and the residue Y is a payload, and a pharmaceutically acceptable carrier, excipient, and/or diluent. The payload may be any payload of the embodiments above.

In some embodiments of the pharmaceutical composition, the compound has the structure of formula (I). In some preferred embodiments of the pharmaceutical composition, the compound has the structure of formula (Ia). In some embodiments of the pharmaceutical composition the modified and/or unmodified oligonucleotide in formula (I) or (Ia) binds to a target nucleotide sequence in a hepatocytic cell and modifies expression of a gene encoded by the target nucleotide sequence. Modification of expression is to be understood herein to alter expression by increasing or decreasing the expression rate. In some preferred embodiments of the pharmaceutical composition, the modified and/or unmodified oligonucleotide inhibits expression of the gene encoded by the target nucleotide sequence. The pharmaceutical composition may be administered in any form suitable for administration to subjects. In some preferred embodiments of the pharmaceutical composition, the pharmaceutical composition is suitable for subcutaneous or intravenous administration to the subject.

Kits

In some embodiments, the compounds and pharmaceutical compositions of the present disclosure are provided in a kit. In various aspects, the kit comprises the compounds as a unit dose. For purposes herein "unit dose" refers to a discrete amount dispersed in a suitable carrier. In various aspects, the unit dose is the amount sufficient to provide a subject with a desired effect, e.g., reduction of target gene expression. Accordingly, provided herein are kits comprising the compounds of the present disclosure optionally provided in unit doses. In various aspects, the kit comprises several unit doses, e.g., a week or month supply of unit doses, optionally, each of which is individually packaged or otherwise separated from other unit doses. In some embodiments, the components of the kit/unit dose are packaged with instructions for administration to a patient. In some embodiments, the kit comprises one or more devices for administration to a patient, e.g., a needle and/or syringe, and the like. In some aspects, the compounds of the present disclosure, a pharmaceutically acceptable salt thereof, is pre-packaged in a ready to use form, e.g., a syringe and/or an intravenous bag, etc. In some aspects, the kit further comprises other therapeutic or diagnostic agents or pharmaceutically acceptable carriers (e.g., solvents, buffers, and/or diluents, etc.), including any of those described herein. In particular aspects, the kit comprises the compounds of the present disclosure, along with an agent, e.g., a therapeutic agent.

SPECIFIC EMBODIMENTS

Embodiment 1 of the invention comprises a compound having the structure of formula (0):

wherein k is an integer from 1 to 5, m is an integer from 0 to 11, n is an integer from 0 to 5, X is a hydroxy-protecting group or an H atom, Y is a hydroxy-protecting group, an H atom, a payload, or a solid support, wherein the payload or the solid support are optionally connected via a spacer, and $R^1$ is independently selected from hydroxy-protecting groups and H atom.

Embodiment 2 of the invention comprises a compound according to embodiment 1, wherein Y is a payload, wherein the payload comprises an oligomeric compound such as an oligonucleotide, a peptide, an antibody, an antibody fragment, or a chemical compound having pharmaceutical activity.

Embodiment 3 of the invention comprises a compound according to embodiment 1 or 2, wherein X and $R^1$ each represent an H atom.

Embodiment 4 of the invention comprises a compound according to any one of the preceding embodiments having the structure of formula (I):

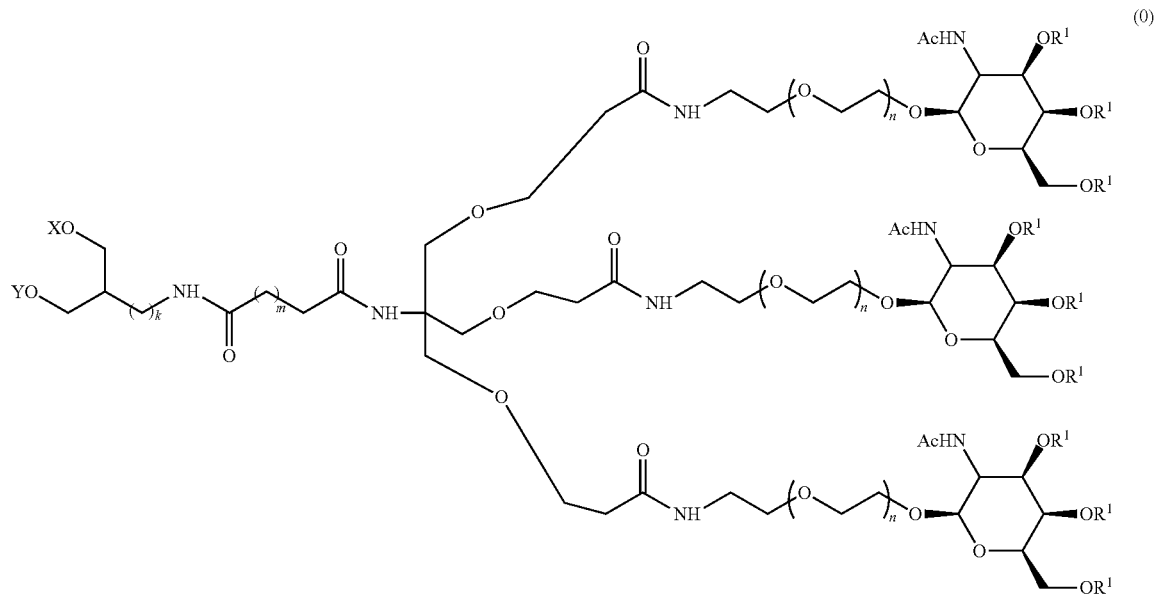

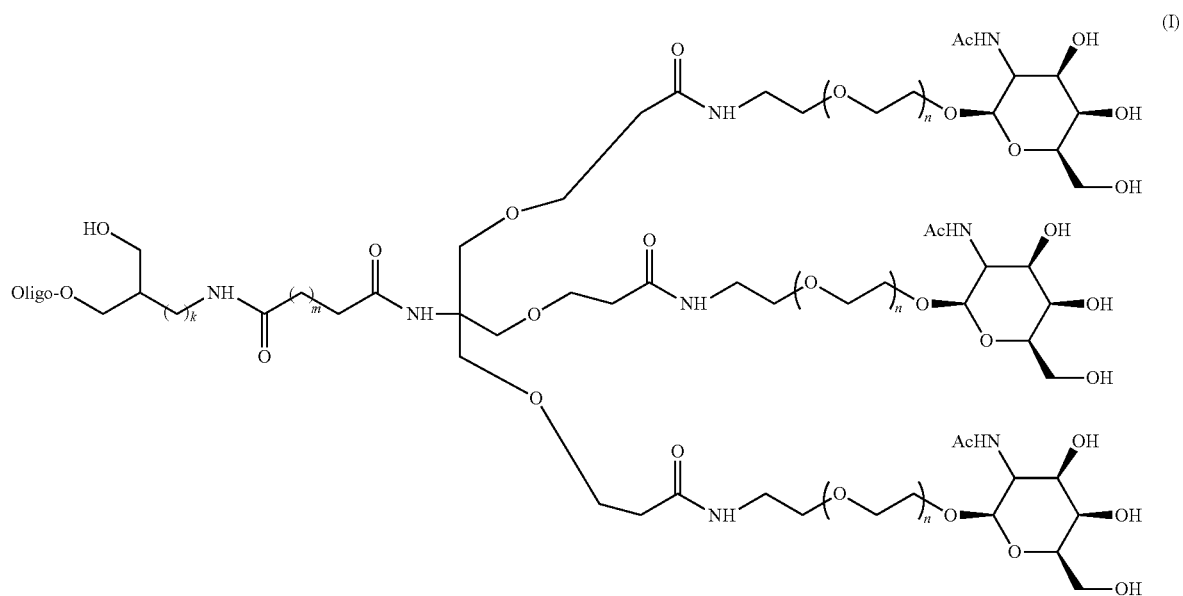

wherein
  k is an integer from 1 to 5,
  m is an integer from 0 to 11,
  n is an integer from 0 to 5, and
  Oligo represents a modified and/or unmodified oligonucleotide.

Embodiment 5 of the invention comprises a compound according to embodiment 4, wherein the modified and/or unmodified oligonucleotide is a single-stranded or double-stranded modified and/or unmodified oligonucleotide.

Embodiment 6 of the invention comprises a compound according to embodiment 4, wherein the modified and/or unmodified oligonucleotide is a single stranded oligonucleotide, microRNA (miRNA), or a single stranded RNA (ssRNA).

Embodiment 7 of the invention comprises a compound according to embodiment 4, wherein the modified and/or unmodified oligonucleotide is a double-stranded oligonucleotide and is a short hairpin RNA (shRNA) or small interfering RNA (siRNA).

Embodiment 8 of the invention comprises a compound according to any one of embodiments 4 to 7, wherein the modified and/or unmodified oligonucleotide is attached via the 3' end of the sense strand.

Embodiment 9 of the invention comprises a compound according to any one of embodiments 4 to 8, wherein the modified and/or unmodified oligonucleotide binds to a target nucleotide sequence and modifies expression of a gene encoded by the target nucleotide sequence.

Embodiment 10 of the invention comprises a compound according to embodiment 9, wherein the modified and/or unmodified oligonucleotide inhibits expression of the gene encoded by the target nucleotide sequence, preferably by inhibiting transcription or translation of the target nucleotide sequence.

Embodiment 11 of the invention comprises a compound according to embodiment 10, wherein the modified and/or unmodified oligonucleotide inhibits expression of the gene by at least about 70%, 75%, 80%, 85%, 90% h, 95%, 98% or 99%.

Embodiment 12 of the invention comprises a compound according to any one of embodiments 4 to 11, wherein the target nucleotide sequence of the modified and/or unmodified oligonucleotide is a messenger RNA (mRNA).

Embodiment 13 of the invention comprises a compound according to any one of embodiments 4 to 12, wherein the target nucleotide sequence of the modified and/or unmodified oligonucleotide encodes a gene associated with a disease which is expressed in the liver, or a gene associated with a liver disorder, preferably a metabolic liver disorder.

Embodiment 14 of the invention comprises a compound according to any one of embodiments 4 to 13, wherein the oligonucleotide is a modified oligonucleotide that is modified to resist degradation, reduce toxicity and/or enhance activity.

Embodiment 15 of the invention comprises a compound according to embodiment 1 having the structure of formula (II):

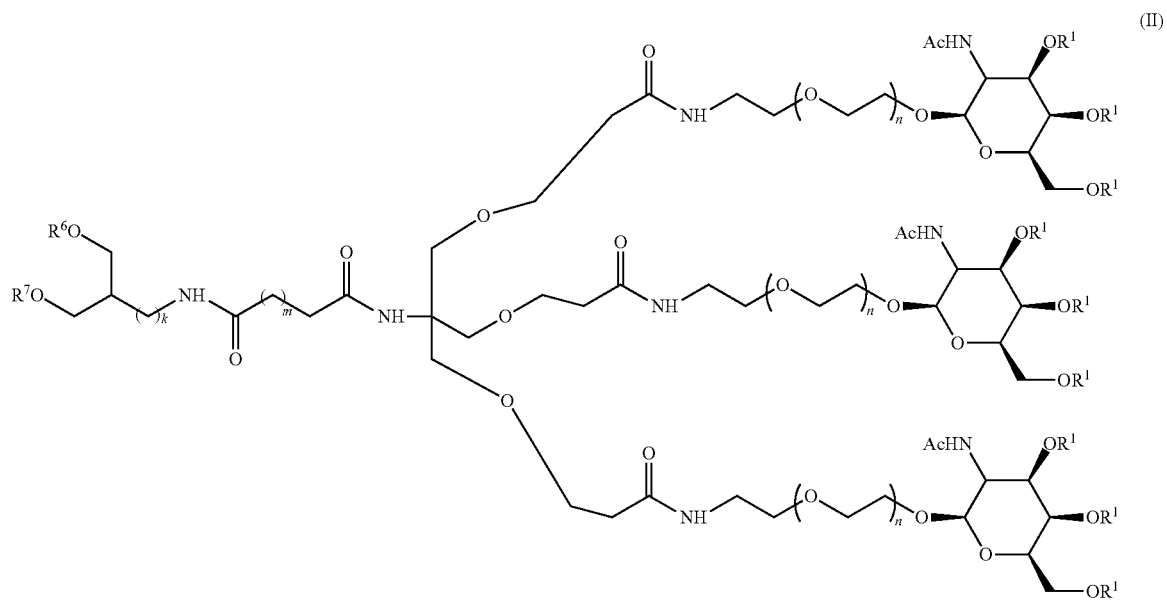

wherein k is an integer from 1 to 5, m is an integer from 0 to 11, n is an integer from 0 to 5, and $R^1$ is independently selected from hydroxy-protecting groups and H atom, preferably is an acetyl group, $R^6$ represents a hydroxy-protecting group, preferably DMT or MMT, more preferably MMT, and $R^7$ represents a moiety of formula (VI):

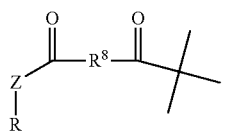

(VI)

wherein

R represents a solid support, optionally connected via a spacer, an amino-protecting group, a hydroxy-protecting group, or an H atom, Z represents NH or O, and $R^8$ represents a linear or branched alkylene having from 1 to 8 carbon atoms, optionally wherein one or more carbon atoms are substituted by an O, S, NH and/or N—($C_1$-$C_3$ alkyl); and/or a cycloalkylene having from 5 to 8 carbon atoms, preferably being ethylene, 1,1 dimethyl ethylene, propylene, n-butylene or 1,2 cyclohexylene.

Embodiment 16 of the invention comprises a compound according to any one of the preceding embodiments, wherein k is 2 or 3, m is 7, 8 or 9, and n is 2 or 3.

Embodiment 17 of the invention comprises a compound according to any one of the preceding embodiments, wherein the sum of k and m is an integer from 8 to 12, and preferably is 10.

Embodiment 18 of the invention comprises a compound according to any one of the preceding embodiments, wherein the compound has the structure of formula (0a), (Ia) or (Ia):

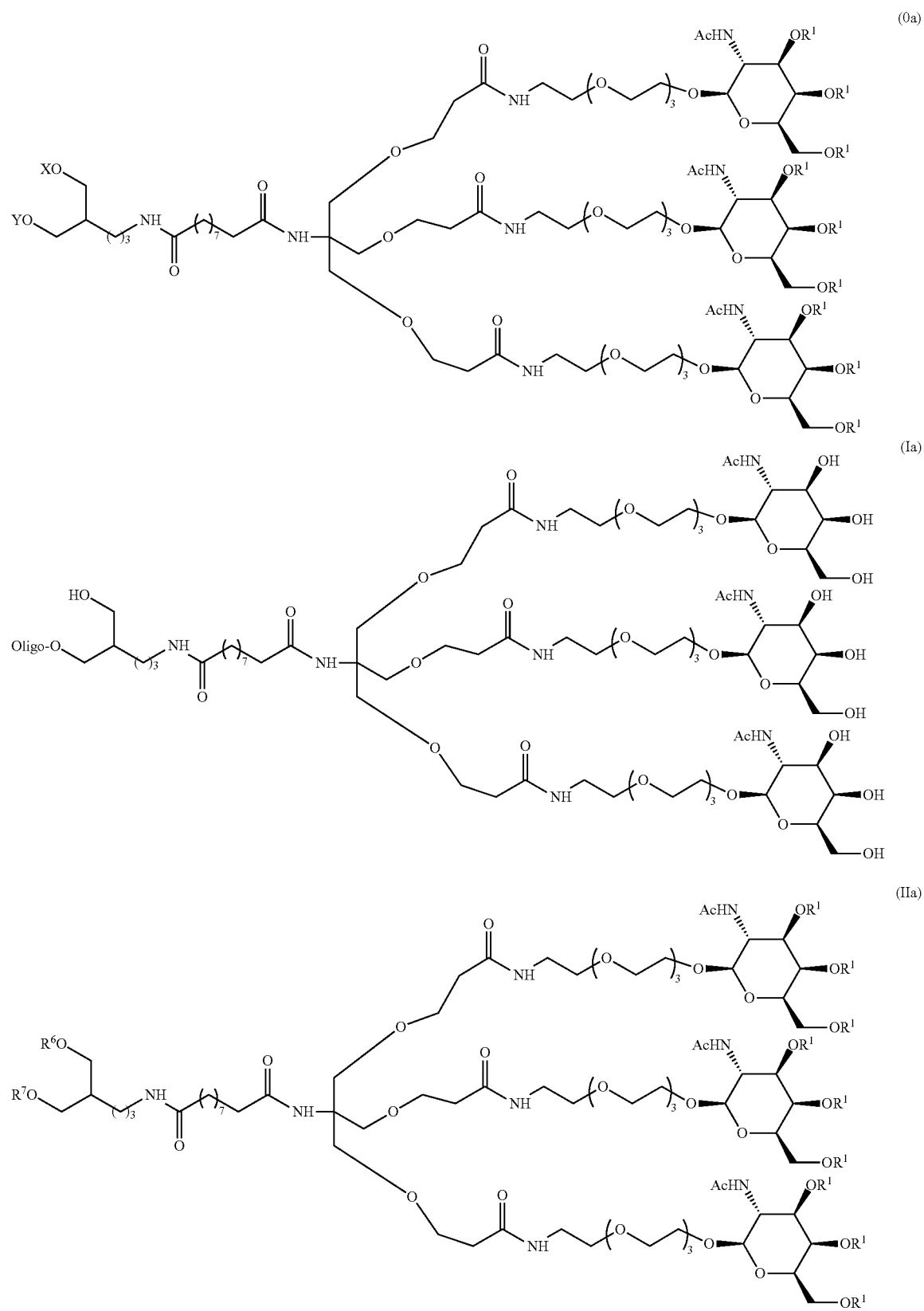
wherein X, Y, Oligo, $R^1$, $R^6$ and $R^7$ are as defined in the preceding embodiments.

Embodiment 19 of the invention comprises a compound having the structure of formula (III):

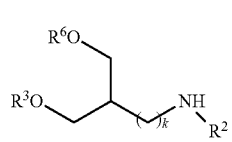
(III)

wherein k is an integer from 1 to 5, $R^2$ represents an amino-protecting group or an H atom, $R^3$ represents a solid support, optionally connected via a spacer, a hydroxy-protecting group, or an H atom, and $R^1$ represents a hydroxy-protecting group, preferably DMT or MMT, more preferably MMT.

Embodiment 20 of the invention comprises a compound according to embodiment 19, wherein k is 2 or 3, preferably 3.

Embodiment 21 of the invention comprises a compound according to embodiment 19 or 20, wherein $R^2$ represents an amino-protecting group, preferably a fluorenylmethoxycarbonyl group (Fmoc), and/or $R^3$ represents an H atom.

Embodiment 22 of the invention comprises a compound according to any one of embodiments 19 to 21, wherein the compound has the structure of formula (IIIa):

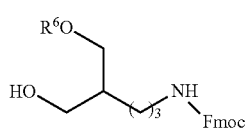
(IIIa)

wherein $R^6$ represents a hydroxy-protecting group, preferably DMT or MMT, more preferably MMT.

Embodiment 23 of the invention comprises a compound according to embodiment 19 or 20, wherein $R^2$ represents an H atom, and/or $R^3$ represents a solid support, optionally connected via a spacer.

Embodiment 24 of the invention comprises a compound according to any one of embodiments 19, 20 and 23, wherein the compound has the structure of any one of formulas (IIIb1) to (IIIb5):

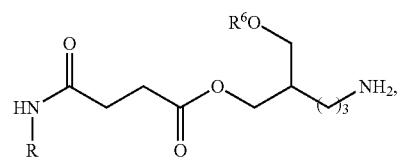
(IIIb1)

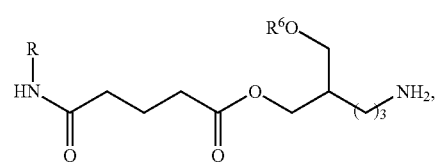
(IIIb2)

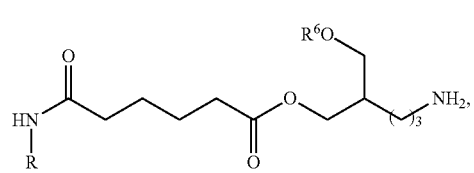
(IIIb3)

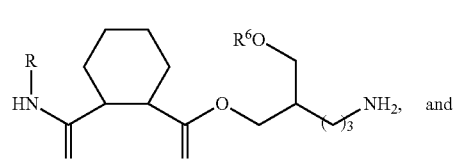
(IIIb4)

and

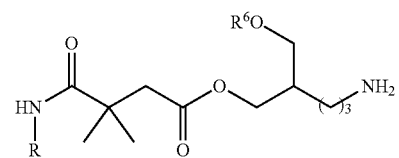
(IIIb5)

wherein

R represents a solid support, optionally connected via a spacer, an amino-protecting group, or an H atom, and $R^6$ represents a hydroxy-protecting group, preferably DMT or MMT, more preferably MMT.

Embodiment 25 of the invention comprises a process for the preparation of a compound having the structure of formula (0):

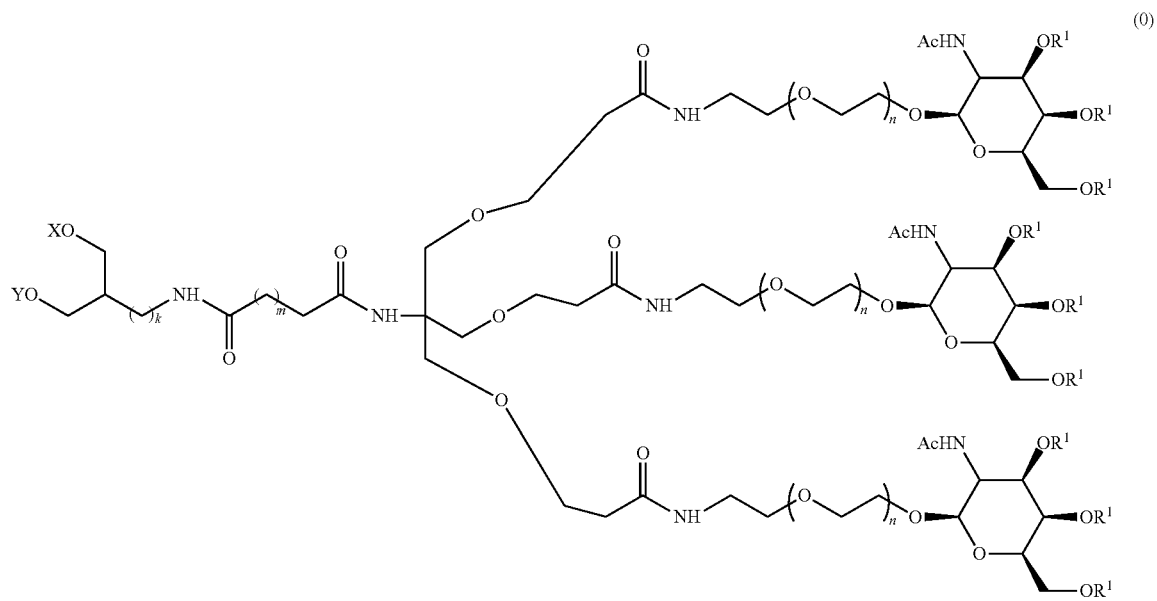

wherein k is an integer from 1 to 5, m is an integer from 0 to 11, n is an integer from 0 to 5, X is a hydroxy-protecting group or an H atom, Y is a hydroxy-protecting group, an H atom, a payload or a solid support, wherein the payload or the solid support are optionally connected via a spacer, and $R^1$ is independently selected from hydroxy-protecting groups and H atom, comprising the step of reacting the compound having the structure of formula (III) with compound (V) e.g., by standard amide coupling:

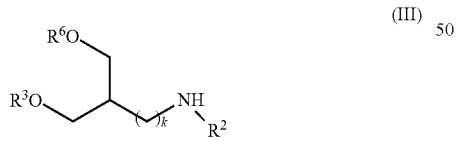

wherein k is an integer from 1 to 5, $R^2$ represents an amino-protecting group or an H atom, and $R^3$ represents a solid support, optionally connected via a spacer, a hydroxy-protecting group, or an H atom, and $R^6$ represents a hydroxy-protecting group, preferably DMT or MMT, more preferably MMT.

Embodiment 26 of the invention comprises a process according to embodiment 25, wherein the compound of formula (0) has the structure of formula (I):

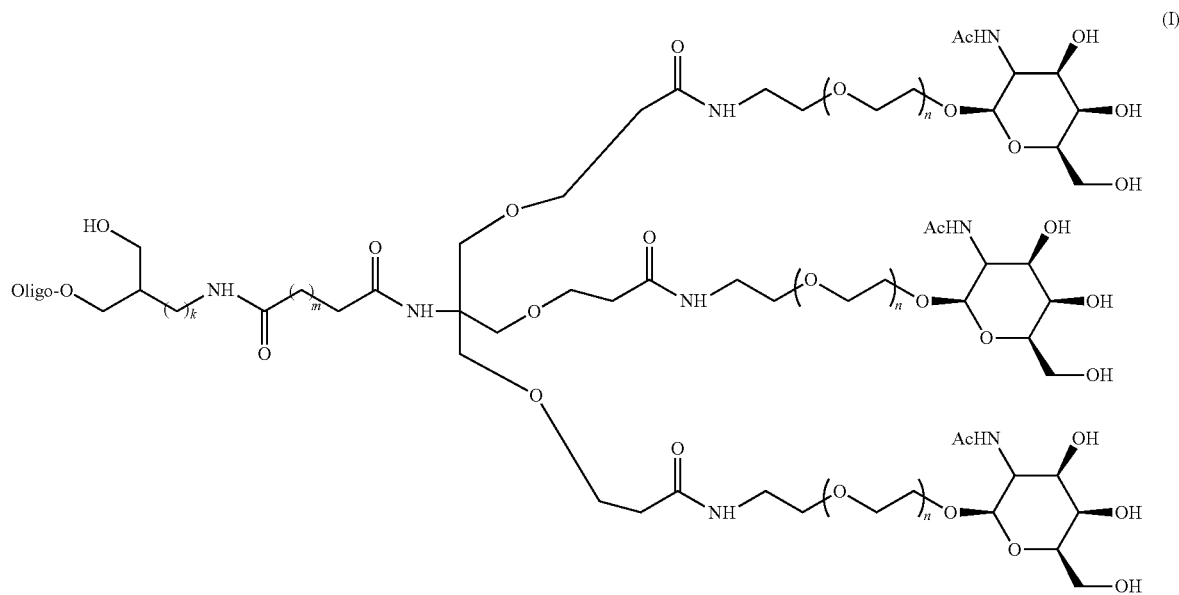

wherein
k is an integer from 1 to 5,
m is an integer from 0 to 11,
n is an integer from 0 to 5, and
Oligo represents a modified and/or unmodified oligonucleotide.

Embodiment 27 of the invention comprises a process according to embodiment 25, wherein the compound of formula (0) has the structure of formula (II):

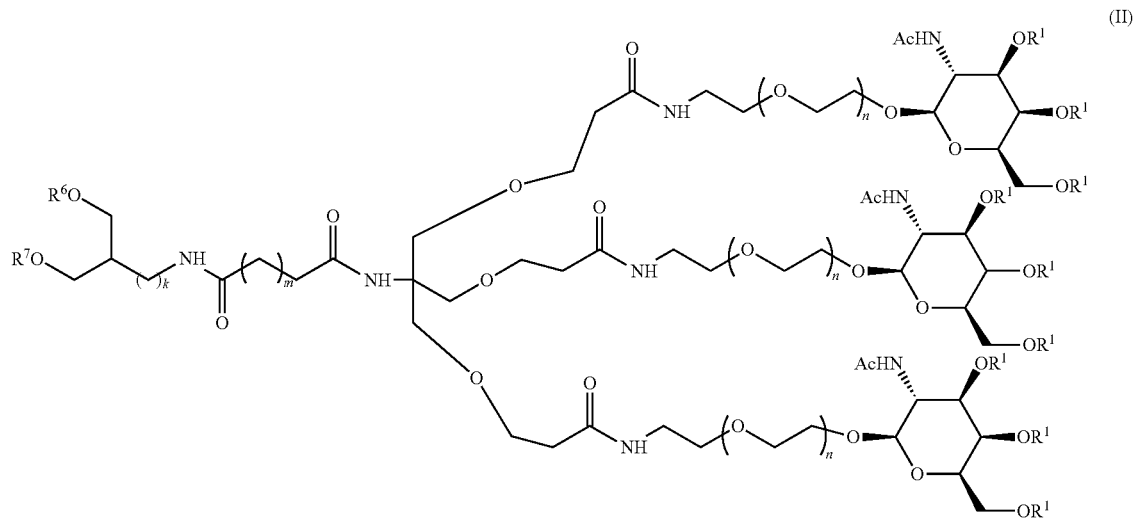

wherein k is an integer from 1 to 5, m is an integer from 0 to 11, n is an integer from 0 to 5, and $R^1$ is independently selected from hydroxy-protecting groups and H atom, preferably is an acetyl group, $R^7$ represents a hydroxy-protecting group, preferably MMT, and $R^7$ represents a moiety of formula (VI):

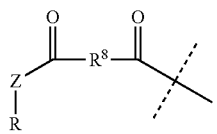
(VI)

wherein

R represents a solid support, optionally connected via a spacer, an amino-protecting group, a hydroxy-protecting group, or an H atom, Z represents NH or O, and $R^8$ represents a linear or branched alkylene having from 1 to 8 carbon atoms, optionally wherein one or more carbon atoms are substituted by an O, S, NH and/or N—($C_1$-$C_3$ alkyl); and/or a cycloalkylene having from 5 to 8 carbon atoms, preferably being ethylene, 1,1 dimethyl ethylene, propylene, n-butylene or 1,2 cyclohexylene.

Embodiment 28 of the invention comprises a process according to any one of embodiments 25 to 27, comprising the step of reacting the compound having the structure of formula (IV):

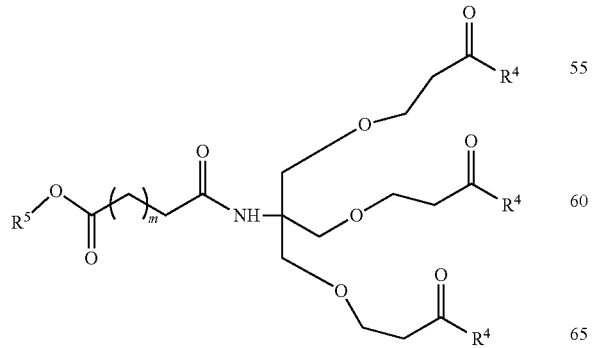
(IV)

wherein m is an integer from 0 to 11, preferably 7, $R_4$ represents

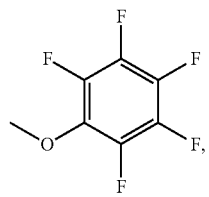

and $R^5$ represents a hydroxy-protecting group, preferably a benzyl group.

Embodiment 29 of the invention comprises a process according to any one of embodiments 25 to 28, comprising the steps of:

a) providing a compound having the structure of formula (III):

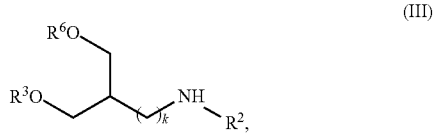
(III)

wherein k is an integer from 1 to 5, preferably 3, $R^2$ represents an H atom, $R^3$ represents a solid support, optionally connected via a spacer, a hydroxyl-protecting group, or an H atom, and $R^6$ represents a hydroxy-protecting group, preferably DMT or MMT, more preferably MMT;

b) providing a compound having the structure of formula (V):

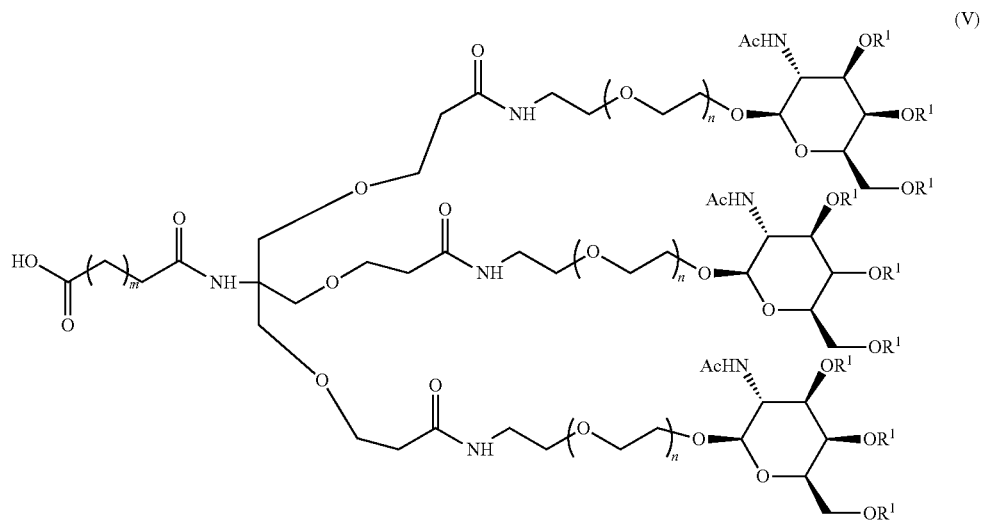

(V)

wherein
   m is an integer from 0 to 11, preferably 7,
   n is an integer from 0 to 5, preferably 3,
   $R^1$ is independently selected from hydroxy-protecting groups, preferably being acetyl groups; and
c) reacting the compound of formula (III) provided in step a) and the compound of formula (V) provided in step b) to obtain the compound of formula (0), wherein Y is an H atom, a hydroxy-protecting group, or a solid support, optionally connected via a spacer, and X is a hydroxy-protecting group, preferably DMT or MMT, more preferably MMT, or to obtain the compound of formula (II).

Embodiment 30 of the invention comprises a process according to embodiment 29, further comprising the step:
d) reacting the compound obtained in step c) to obtain the compound of formula (0), wherein Y is a payload optionally connected via a spacer, and X and $R^1$ each are an H atom, or to obtain the compound of formula (I).

Embodiment 31 of the invention comprises a process according to any one of embodiments 25 to 30, wherein in step d) of the process, the compound of formula (II) is reacted with at least two modified and/or unmodified nucleotides and/or nucleosides to obtain a compound of formula (I).

Embodiment 32 of the invention comprises a process according to any one of embodiments 25 to 30, wherein in step d) of the process, the compound of formula (0), wherein Y is a hydroxy-protecting group, an H atom, or a solid support, optionally connected via a spacer, is further reacted with a payload or a payload-precursor to obtain the compound of formula (0), wherein Y is a payload optionally connected via a spacer.

Embodiment 33 of the invention comprises a process according to embodiment 32, wherein the payload comprises an oligomeric compound such as an oligonucleotide, a peptide, an antibody, an antibody fragment, or a chemical compound having pharmaceutical activity.

Embodiment 34 of the invention comprises a process according to any one of embodiments 25 to 33, wherein step b) of the process comprises the step of reacting the compound having the structure of formula (IV):

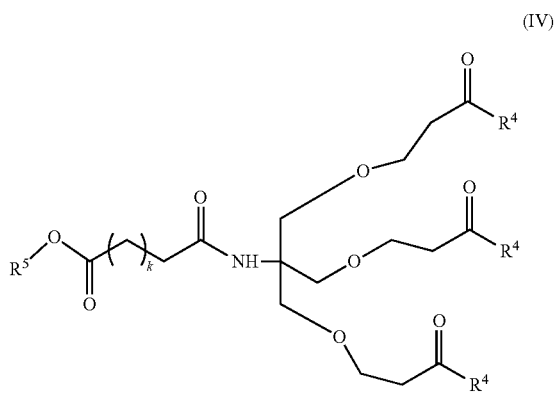

(IV)

wherein
   m is an integer from 0 to 11, preferably 7,
   $R^4$ represents

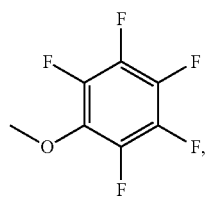

and
   $R^5$ represents a hydroxy-protecting group, preferably a benzyl group.

Embodiment 35 of the invention comprises a method for preparing a compound having the structure of formula (0):

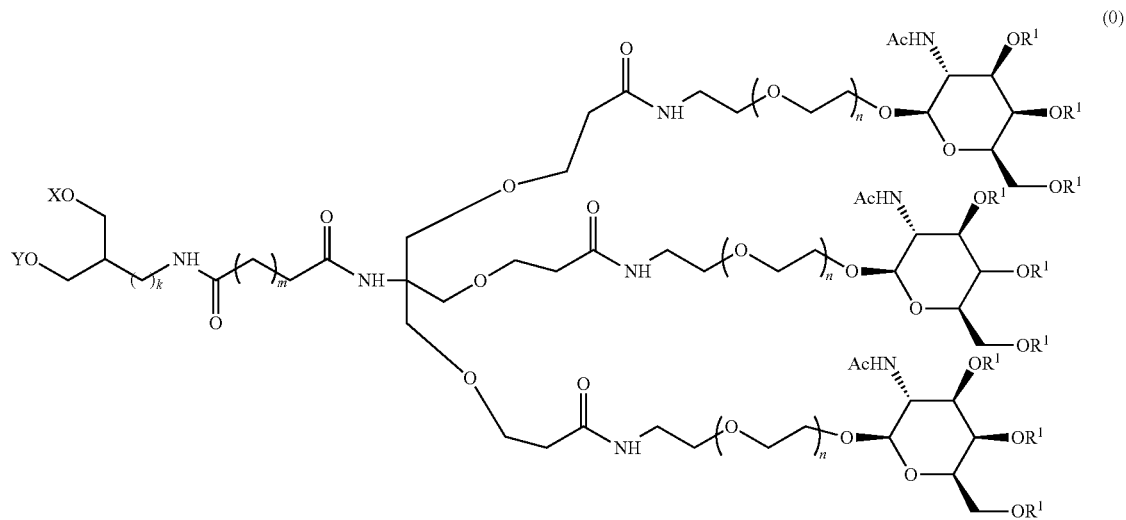

wherein
- k is an integer from 1 to 5,
- m is an integer from 0 to 11,
- n is an integer from 0 to 5,
- X is a hydroxy-protecting group or an H atom,
- Y is a hydroxy-protecting group, an H atom, a payload or a solid support, wherein the payload or the solid support are optionally connected via a spacer, and
- $R^1$ is independently selected from hydroxy-protecting groups and H atom, comprising the step of reacting the compound having the structure of formula (III) with a compound having the structure of formula (V) e.g., by amide coupling:

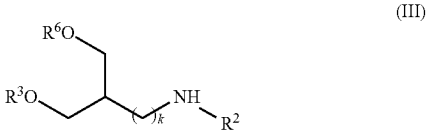

wherein
- k is an integer from 1 to 5,
- $R^2$ represents an amino-protecting group or an H atom, and
- $R^3$ represents a solid support, optionally connected via a spacer, a hydroxy-protecting group, or an H atom, and
- $R^6$ represents a hydroxy-protecting group, preferably DMT or MMT, more preferably MMT, wherein the compound having the structure of formula (V) is:

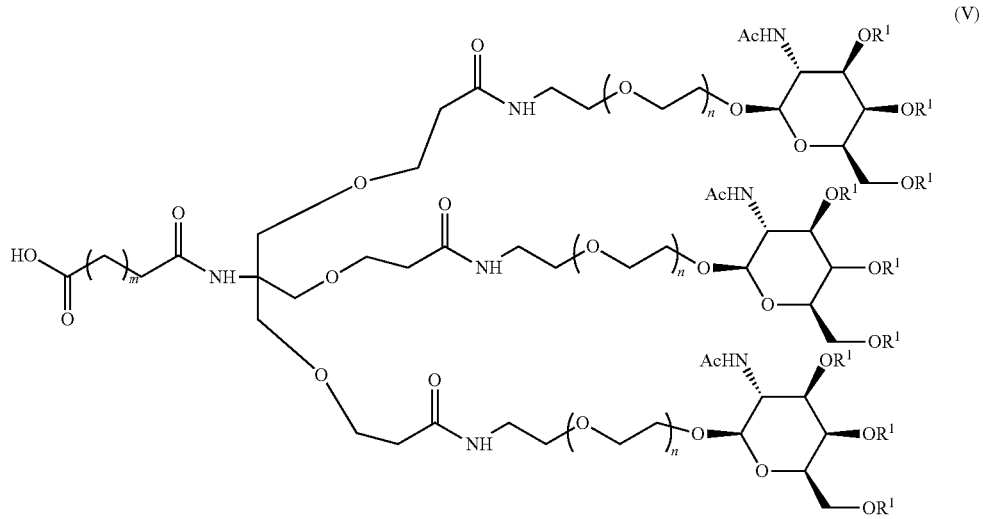

Embodiment 36 of the invention comprises a method according to embodiment 35, wherein the compound of formula (0) has the structure of formula (I):

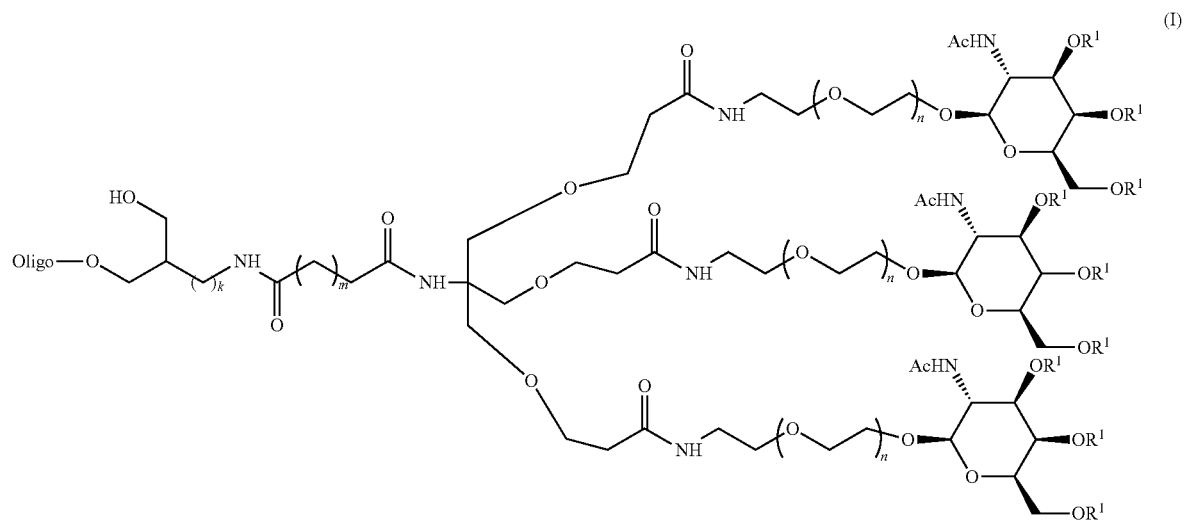

wherein
k is an integer from 1 to 5,
m is an integer from 0 to 11,
n is an integer from 0 to 5, and
Oligo represents a modified and/or unmodified oligonucleotide.

Embodiment 37 of the invention comprises a method according to embodiment 35, wherein the compound of formula (0) has the structure of formula (II):

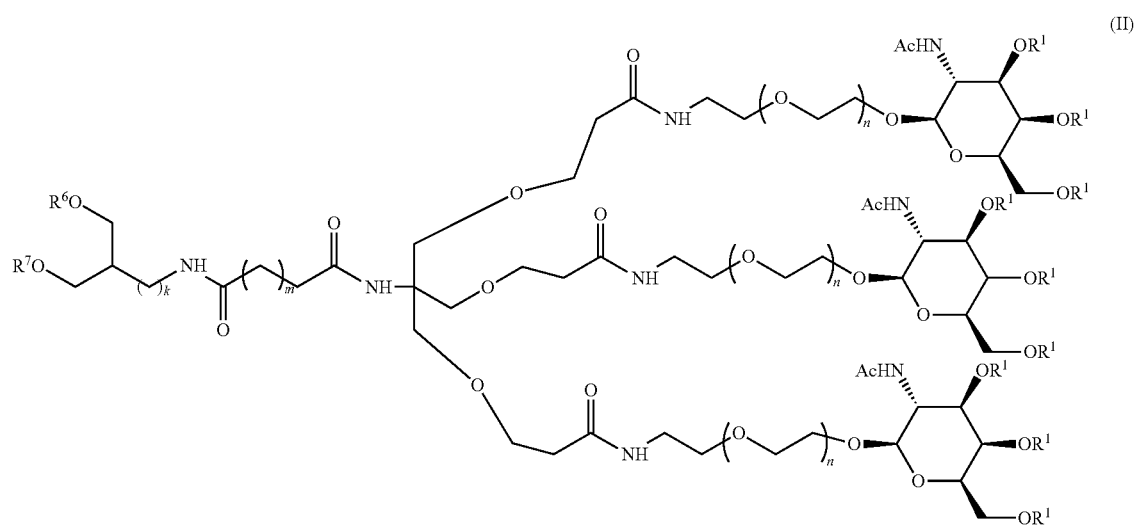

wherein k is an integer from 1 to 5, m is an integer from 0 to 11, n is an integer from 0 to 5, and $R^1$ is independently selected from hydroxy-protecting groups and H atom, preferably is an acetyl group, $R^6$ represents a hydroxy-protecting group, preferably MMT, and $R^7$ represents a moiety of formula (VI):

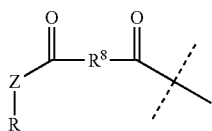

(VI)

wherein

R represents a solid support, optionally connected via a spacer, an amino-protecting group, a hydroxy-protecting group, or an H atom, Z represents NH or O, and $R^8$ represents a linear or branched alkylene having from 1 to 8 carbon atoms, optionally wherein one or more carbon atoms are substituted by an O, S, NH and/or N—($C_1$-$C_3$ alkyl); and/or a cycloalkylene having from 5 to 8 carbon atoms, preferably being ethylene, 1,1 dimethyl ethylene, propylene, n-butylene or 1,2 cyclohexylene.

Embodiment 38 of the invention comprises a method according to any one of embodiments 35 to 37, comprising the step of reacting the compound having the structure of formula (IV):

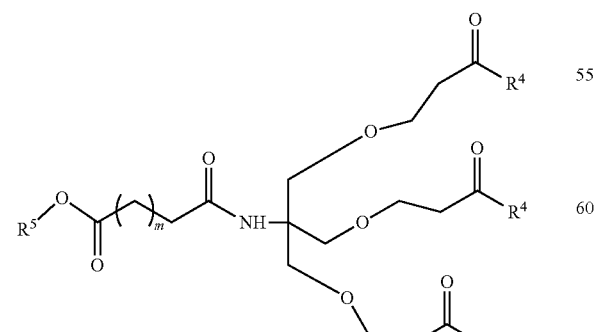

(IV)

wherein m is an integer from 0 to 11, preferably 7, $R^4$ represents

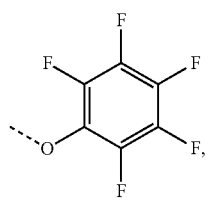

and $R^5$ represents a hydroxy-protecting group, preferably a benzyl group.

Embodiment 39 of the invention comprises a method according to any one of embodiments 35 to 38, comprising the steps of:

a) providing a compound having the structure of formula (III):

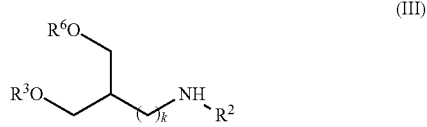

(III)

wherein k is an integer from 1 to 5, preferably 3, $R^2$ represents an H atom, $R^3$ represents a solid support, optionally connected via a spacer, a hydroxyl-protecting group, or an H atom, and $R^6$ represents a hydroxy-protecting group, preferably DMT or MMT, more preferably MMT;

b) providing a compound having the structure of formula (V):

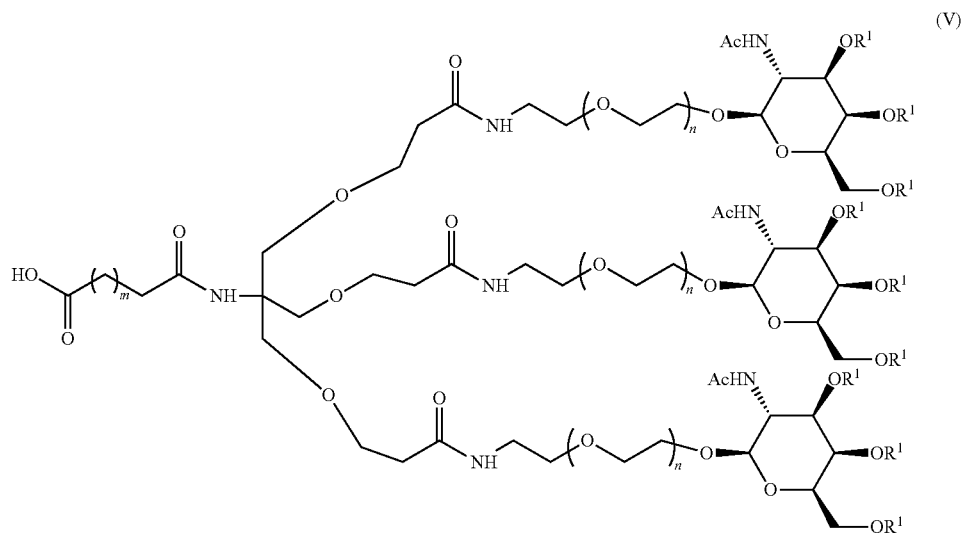

(V)

wherein
- m is an integer from 0 to 11, preferably 7,
- n is an integer from 0 to 5, preferably 3,
- $R^1$ is independently selected from hydroxy-protecting groups, preferably being acetyl groups; and
- c) reacting the compound of formula (III) provided in step a) and the compound of formula (V) provided in step b) to obtain the compound of formula (0), wherein Y is an H atom, a hydroxy-protecting group, or a solid support, optionally connected via a spacer, and X is a hydroxy-protecting group, preferably DMT or MMT, more preferably MMT, or to obtain the compound of formula (II).

Embodiment 40 of the invention comprises a method according to embodiment 39, further comprising the step:
- d) reacting the compound obtained in step c) to obtain the compound of formula (0), wherein Y is a payload optionally connected via a spacer, and X and $R^1$ each are an H atom, or to obtain the compound of formula (I).

Embodiment 41 of the invention comprises a method according to any one of embodiments 35 to 40, wherein in step d) of the process, the compound of formula (II) is reacted with at least two modified and/or unmodified nucleotides and/or nucleosides to obtain a compound of formula (I).

Embodiment 42 of the invention comprises a method according to any one of embodiments 35 to 40, wherein in step d) of the process, the compound of formula (0), wherein Y is a hydroxy-protecting group, an H atom, or a solid support, optionally connected via a spacer, is further reacted with a payload or a payload-precursor to obtain the compound of formula (0), wherein Y is a payload optionally connected via a spacer.

Embodiment 43 of the invention comprises a method according to embodiment 42, wherein the payload comprises an oligomeric compound such as an oligonucleotide, a peptide, an antibody, an antibody fragment, or a chemical compound having pharmaceutical activity.

Embodiment 44 of the invention comprises a method according to any one of embodiments 35 to 43, wherein step b) of the process comprises the step of reacting the compound having the structure of formula (IV):

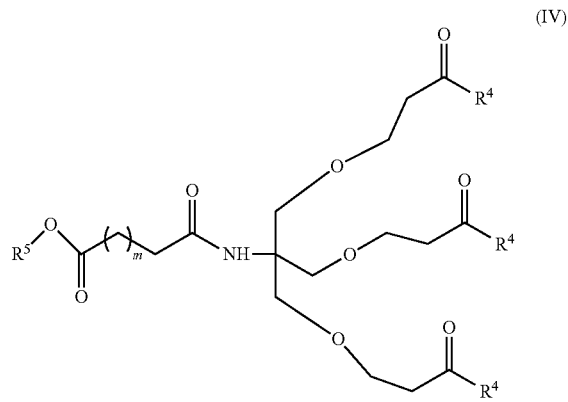

(IV)

wherein
- m is an integer from 0 to 11, preferably 7,
- $R^4$ represents

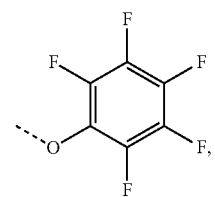

and
- $R^5$ represents a hydroxy-protecting group, preferably a benzyl group.

Embodiment 45 of the invention comprises a compound having the structure of formula (0):

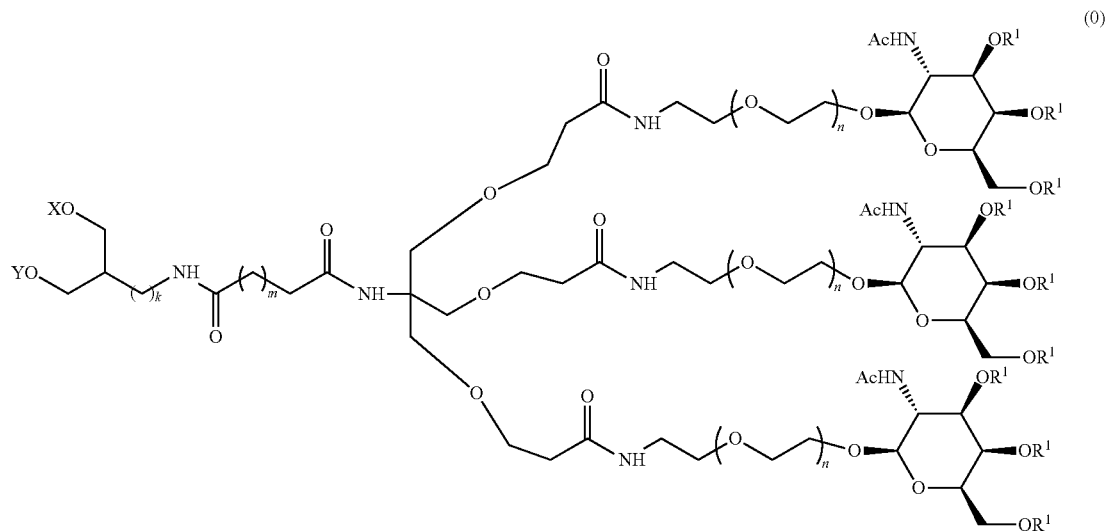

wherein
  k is an integer from 1 to 5, preferably 3,
  m is an integer from 0 to 11, preferably 7,
  n is an integer from 0 to 5, preferably 3,
  X is an H atom,
  Y is a payload optionally connected via a spacer, and
  $R^1$ is an H atom,
for use in a method of treating a subject or diagnosing a subject with a disease or disorder, the subject comprising cells expressing asialoglycoprotein receptor (ASGPR).

Embodiment 46 of the invention comprises a compound for use according to embodiment 45, wherein the payload comprises an oligomeric compound such as an oligonucleotide, a peptide, an antibody, an antibody fragment, or a chemical compound having pharmaceutical activity.

Embodiment 47 of the invention comprises a compound for use according to embodiment 45 or 46 wherein the compound has the structure of formula (I):

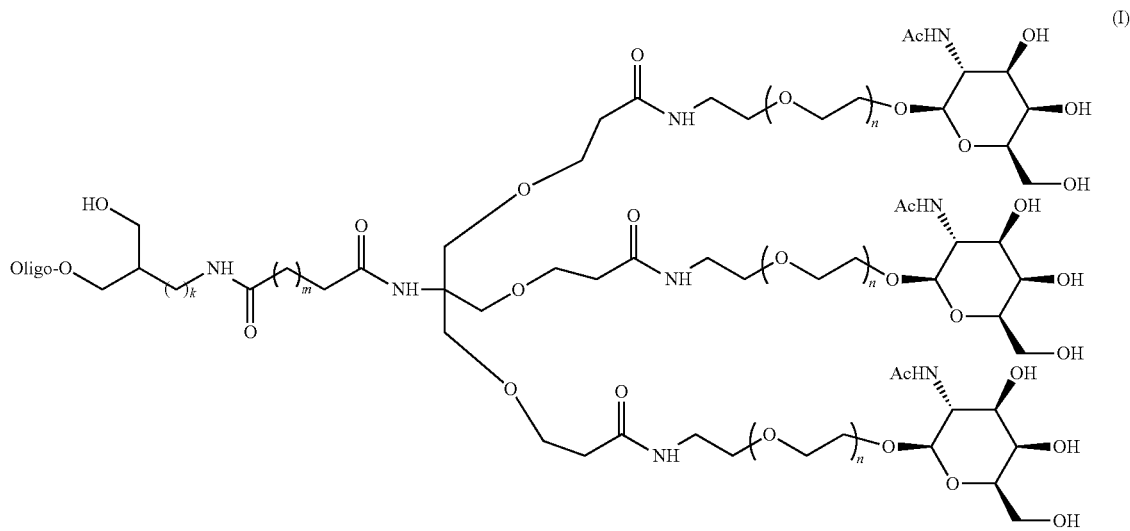

wherein
k is an integer from 1 to 5,
m is an integer from 0 to 11,
n is an integer from 0 to 5, and
Oligo represents a modified and/or unmodified oligonucleotide.

Embodiment 48 of the invention comprises a compound for use according to embodiment 47, wherein the modified and/or unmodified oligonucleotide is a single-stranded or double-stranded modified and/or unmodified oligonucleotide.

Embodiment 49 of the invention comprises a compound for use according to embodiment 47, wherein the modified and/or unmodified oligonucleotide is a single stranded oligonucleotide, microRNA (miRNA), or a single stranded RNA (ssRNA).

Embodiment 50 of the invention comprises a compound for use according to embodiment 47, wherein the modified and/or unmodified oligonucleotide is a double-stranded oligonucleotide and is a short hairpin RNA (shRNA) or small interfering RNA (siRNA).

Embodiment 51 of the invention comprises a compound for use according to any one of embodiments 47 to 50, wherein the modified and/or unmodified oligonucleotide is attached via the 3' end of the sense strand.

Embodiment 52 of the invention comprises a compound for use according to any one of embodiments 47 to 51, wherein the modified and/or unmodified oligonucleotide binds to a target nucleotide sequence and modifies expression of a gene encoded by the target nucleotide sequence.

Embodiment 53 of the invention comprises a compound for use according to embodiment 52, wherein the modified and/or unmodified oligonucleotide inhibits expression of the gene encoded by the target nucleotide sequence, preferably by inhibiting transcription or translation of the target nucleotide sequence.

Embodiment 54 of the invention comprises a compound for use according to embodiment 53, wherein the modified and/or unmodified oligonucleotide inhibits expression of the gene by at least about 70%, 75%, 80%, 85%, 90/o, 95%, 98% or 99%.

Embodiment 55 of the invention comprises a compound for use according to any one of embodiments 47 to 54, wherein the target nucleotide sequence of the modified and/or unmodified oligonucleotide is a messenger RNA (mRNA).

Embodiment 56 of the invention comprises a compound for use according to any one of embodiments 47 to 55, wherein the target nucleotide sequence of the modified and/or unmodified oligonucleotide encodes a gene associated with a disease which is expressed in the liver, or a gene associated with a liver disorder, preferably a metabolic liver disorder.

Embodiment 57 of the invention comprises a compound for use according to any one of embodiments 47 to 56, wherein the oligonucleotide is a modified oligonucleotide that is modified to resist degradation, reduce toxicity and/or enhance activity.

Embodiment 58 of the invention comprises a compound for use according to any one of embodiments 47 to 57, wherein
k is 2 or 3,
m is 7, 8 or 9, and
n is 2 or 3.

Embodiment 59 of the invention comprises a compound for use according to any one of embodiments 47 to 58, wherein the sum of k and m is an integer from 8 to 12, and preferably is 10.

Embodiment 60 of the invention comprises a compound for use according to any one of embodiments 47 to 59, wherein the compound has the structure of formula (Ia):

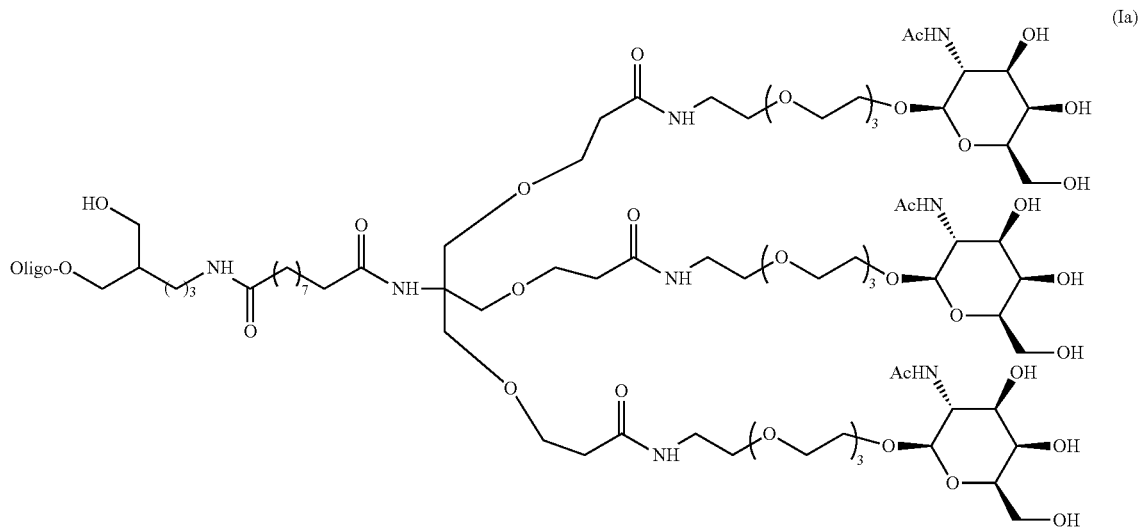

Embodiment 61 of the invention comprises a method for transporting a payload into a cell expressing asialoglycoprotein receptor (ASGPR) comprising the step of administering a compound having the structure of formula (0):

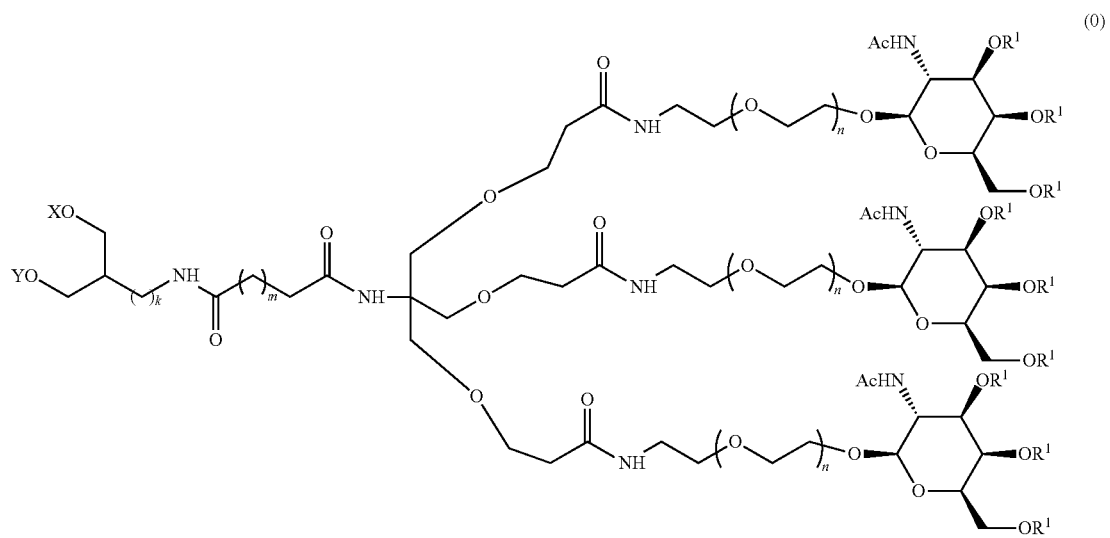

wherein
k is an integer from 1 to 5,
m is an integer from 0 to 1,
n is an integer from 0 to 5,
X is an H atom,
Y is a payload optionally connected via a spacer, and
$R^1$ is an H atom,
wherein the payload is transported into the cell expressing asialoglycoprotein receptor (ASGPR) in the subject in an amount sufficient to treat the subject with the payload.

Embodiment 62 of the invention comprises a method according to embodiment 61, wherein the payload comprises an oligomeric compound such as an oligonucleotide, a peptide, an antibody, an antibody fragment, or a chemical compound having pharmaceutical activity.

Embodiment 63 of the invention comprises a method according to embodiment 61 or 62, wherein the compound has the structure of formula (I):

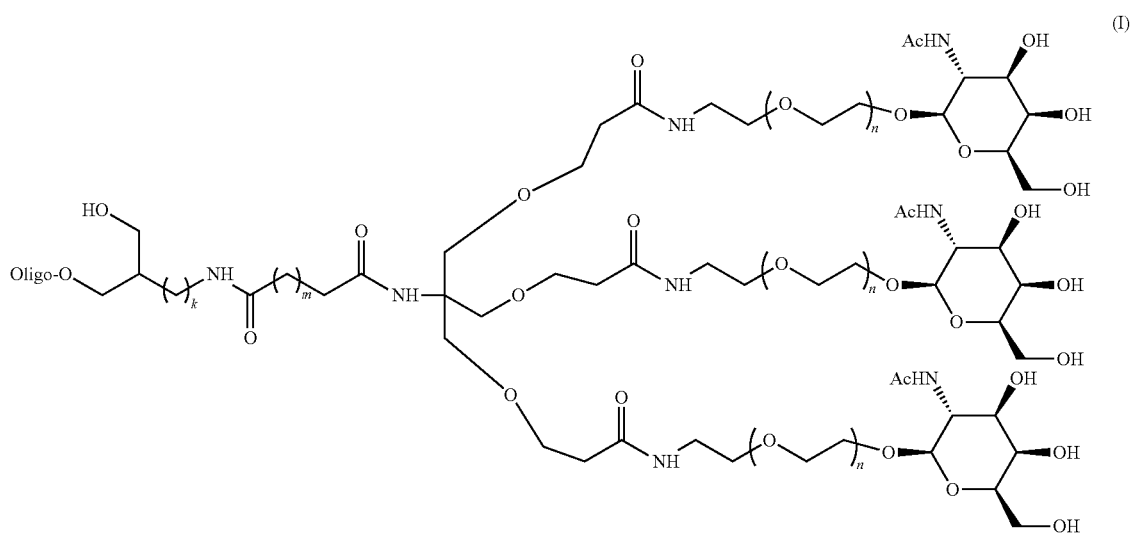

wherein
k is an integer from 1 to 5,
m is an integer from 0 to 11,
n is an integer from 0 to 5, and
Oligo represents a modified and/or unmodified oligonucleotide.

Embodiment 64 of the invention comprises a method according to embodiment 63, wherein the modified and/or unmodified oligonucleotide is a single-stranded or double-stranded modified and/or unmodified oligonucleotide.

Embodiment 65 of the invention comprises a method according to embodiment 63, wherein the modified and/or unmodified oligonucleotide is a single stranded oligonucleotide, microRNA (miRNA), or a single stranded RNA (ssRNA).

Embodiment 66 of the invention comprises a method according to embodiment 63, wherein the modified and/or unmodified oligonucleotide is a double-stranded oligonucleotide and is a short hairpin RNA (shRNA) or small interfering RNA (siRNA).

Embodiment 67 of the invention comprises a method according to any one of embodiments 63 to 66, wherein the modified and/or unmodified oligonucleotide is attached via the 3' end of the sense strand.

Embodiment 68 of the invention comprises a method according to any one of embodiments 63 to 67, wherein the modified and/or unmodified oligonucleotide binds to a target nucleotide sequence and modifies expression of a gene encoded by the target nucleotide sequence.

Embodiment 69 of the invention comprises a method according to embodiment 68, wherein the modified and/or unmodified oligonucleotide inhibits expression of the gene encoded by the target nucleotide sequence, preferably by inhibiting transcription or translation of the target nucleotide sequence.

Embodiment 70 of the invention comprises a method according to embodiment 69, wherein the modified and/or unmodified oligonucleotide inhibits expression of the gene by at least about 70%, 75%, 80%, 85%, 90%, 95%, 98% or 99%.

Embodiment 71 of the invention comprises a method according to any one of embodiments 63 to 70, wherein the target nucleotide sequence of the modified and/or unmodified oligonucleotide is a messenger RNA (mRNA).

Embodiment 72 of the invention comprises a method according to any one of embodiments 63 to 71, wherein the target nucleotide sequence of the modified and/or unmodified oligonucleotide encodes a gene associated with a disease which is expressed in the liver, or a gene associated with a liver disorder, preferably a metabolic liver disorder.

Embodiment 73 of the invention comprises a method according to any one of embodiments 63 to 72, wherein the oligonucleotide is a modified oligonucleotide that is modified to resist degradation, reduce toxicity and/or enhance activity.

Embodiment 74 of the invention comprises a method according to any one of embodiments 63 to 73, wherein
k is 2 or 3,
m is 7, 8 or 9, and
n is 2 or 3.

Embodiment 75 of the invention comprises a method according to any one of embodiments 63 to 74, wherein the sum of k and m is an integer from 8 to 12, and preferably is 10.

Embodiment 76 of the invention comprises a method according to any one of embodiments 63 to 75, wherein the compound has the structure of formula (Ia):

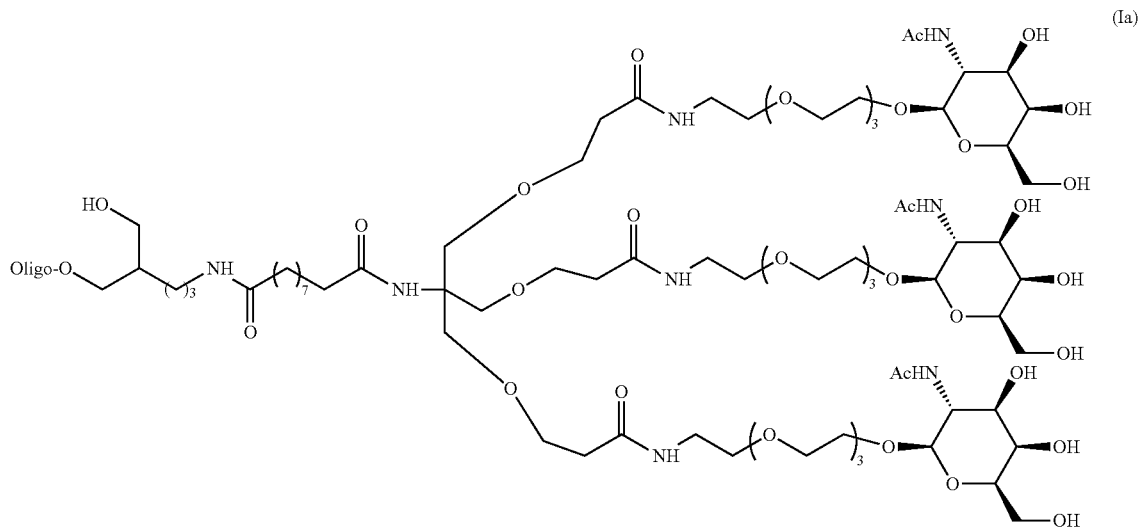

(Ia)

Embodiment 77 of the invention comprises a compound for use according to any one of embodiments 45 to 60 or the method according to any one of embodiments 61 to 76, wherein the compound is administered subcutaneously or intravenously to the subject.

Embodiment 78 of the invention comprises a pharmaceutical composition comprising a compound having the structure of formula (0):

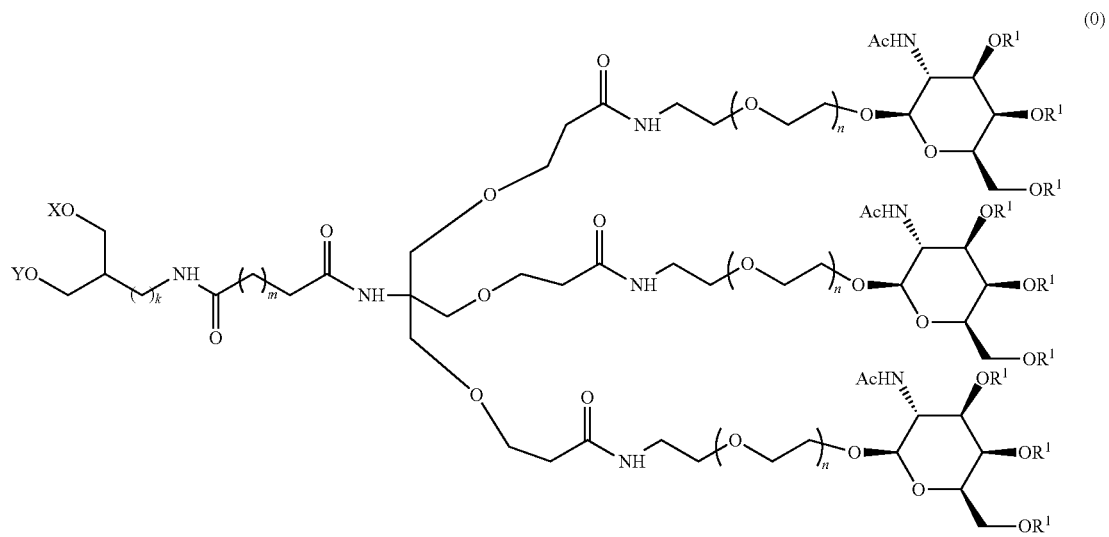

(0)

wherein
k is an integer from 1 to 5, preferably 3,
m is an integer from 0 to 11, preferably 7,
n is an integer from 0 to 5, preferably 3,
X is an H atom,
Y is a payload optionally connected via a spacer, and
R¹ is an H atom,
and a pharmaceutically acceptable carrier, excipient, and/or diluent.

Embodiment 79 of the invention comprises a pharmaceutical composition according to embodiment 78, wherein the payload comprises an oligomeric compound such as an oligonucleotide, a peptide, an antibody, an antibody fragment, or a chemical compound having pharmaceutical activity.

Embodiment 80 of the invention comprises a pharmaceutical composition according to embodiment 78 or 79, wherein the compound has the structure of formula (I):

wherein
k is an integer from 1 to 5,
m is an integer from 0 to 11,
n is an integer from 0 to 5, and
Oligo represents a modified and/or unmodified oligonucleotide.

Embodiment 81 of the invention comprises a pharmaceutical composition according to embodiment 80, wherein the modified and/or unmodified oligonucleotide is a single-stranded or double-stranded modified and/or unmodified oligonucleotide.

Embodiment 82 of the invention comprises a pharmaceutical composition according to embodiment 80, wherein the modified and/or unmodified oligonucleotide is a single stranded oligonucleotide, microRNA (miRNA), or a single stranded RNA (ssRNA).

Embodiment 83 of the invention comprises a pharmaceutical composition according to embodiment 80, wherein the modified and/or unmodified oligonucleotide is a double-

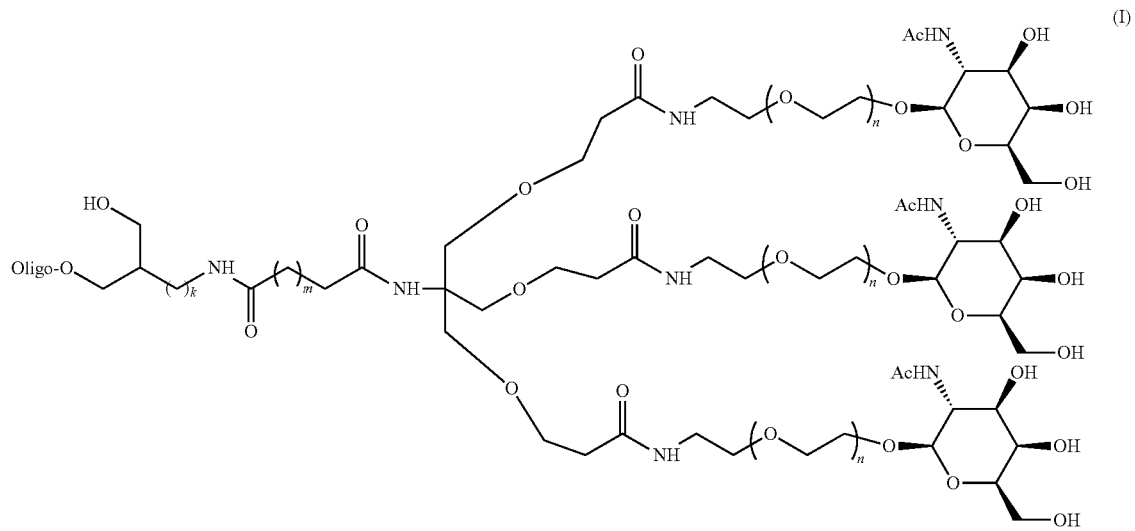

(I)

stranded oligonucleotide and is a short hairpin RNA (shRNA) or small interfering RNA (siRNA).

Embodiment 84 of the invention comprises a pharmaceutical composition according to any one of embodiments 80 to 83, wherein the modified and/or unmodified oligonucleotide is attached via the 3' end of the sense strand.

Embodiment 85 of the invention comprises a pharmaceutical composition according to any one of embodiments 80 to 84, wherein the modified and/or unmodified oligonucleotide binds to a target nucleotide sequence and modifies expression of a gene encoded by the target nucleotide sequence.

Embodiment 91 of the invention comprises a pharmaceutical composition according to any one of embodiments 80 to 90, wherein
k is 2 or 3,
m is 7, 8 or 9, and
n is 2 or 3.

Embodiment 92 of the invention comprises a pharmaceutical composition according to any one of embodiments 80 to 91, wherein the sum of k and m is an integer from 8 to 12, and preferably is 10.

Embodiment 93 of the invention comprises a pharmaceutical composition according to any one of embodiments 80 to 92, wherein the compound has the structure of formula (Ia):

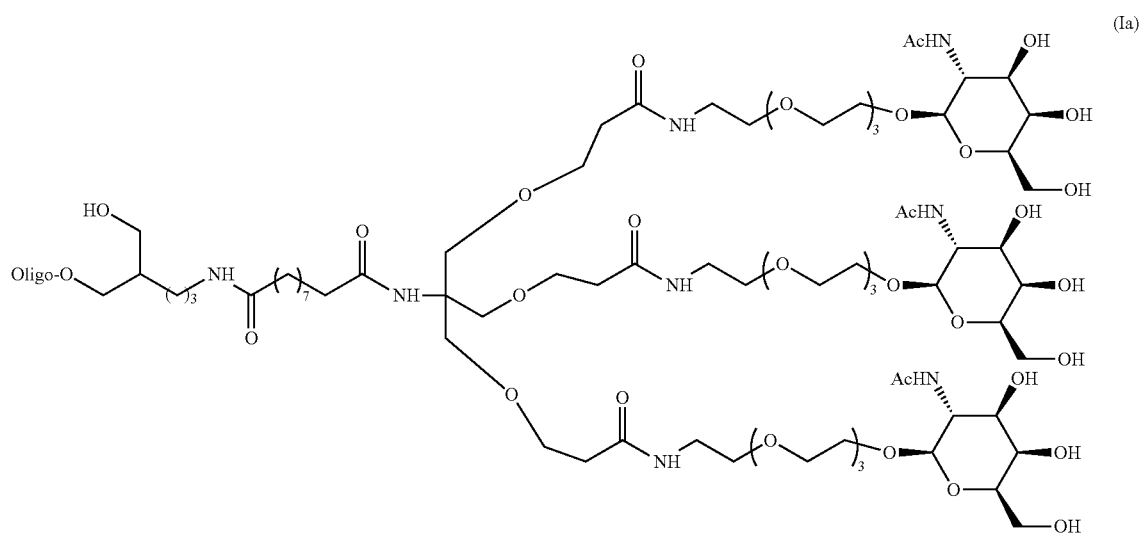

Embodiment 86 of the invention comprises a pharmaceutical composition according to embodiment 85, wherein the modified and/or unmodified oligonucleotide inhibits expression of the gene encoded by the target nucleotide sequence, preferably by inhibiting transcription or translation of the target nucleotide sequence.

Embodiment 87 of the invention comprises a pharmaceutical composition according to embodiment 86, wherein the modified and/or unmodified oligonucleotide inhibits expression of the gene by at least about 70%, 75%, 80%, 85%, 90%, 95%, 98% or 99%.

Embodiment 88 of the invention comprises a pharmaceutical composition according to any one of embodiments 80 to 87, wherein the target nucleotide sequence of the modified and/or unmodified oligonucleotide is a messenger RNA (mRNA).

Embodiment 89 of the invention comprises a pharmaceutical composition according to any one of embodiments 80 to 88, wherein the target nucleotide sequence of the modified and/or unmodified oligonucleotide encodes a gene associated with a disease which is expressed in the liver, or a gene associated with a liver disorder, preferably a metabolic liver disorder.

Embodiment 90 of the invention comprises a pharmaceutical composition according to any one of embodiments 80 to 89, wherein the oligonucleotide is a modified oligonucleotide that is modified to resist degradation, reduce toxicity and/or enhance activity.

Embodiment 94 of the invention comprises a pharmaceutical composition according to any one of embodiments 80 to 93, wherein the pharmaceutical composition is suitable for subcutaneous or intravenous administration to the subject.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is herein incorporated-by-reference in its entirety.

Example 1: Preparation of the GalNAc Compound with Solid Support

ARNATAR GalNAc-Linker-Solid Support Synthesis Procedure

Two synthesis procedures for the manufacturing of trivalent GalNAc solid support are shown infra: Reaction Scheme 1 and Reaction Scheme 2.

Reaction Scheme 1
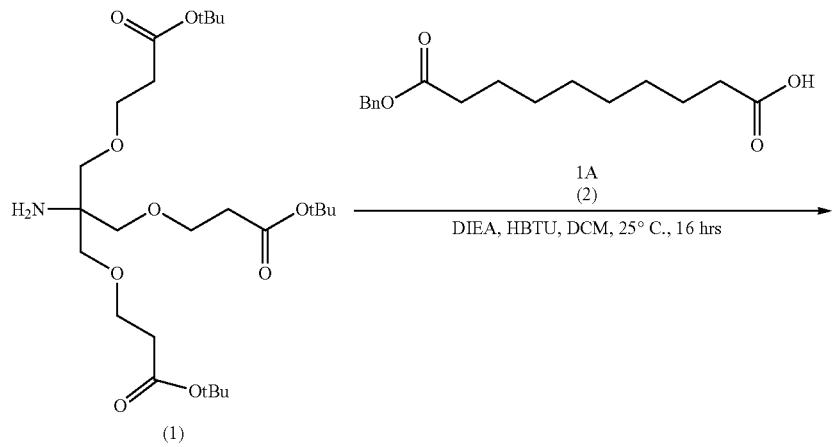
(1)
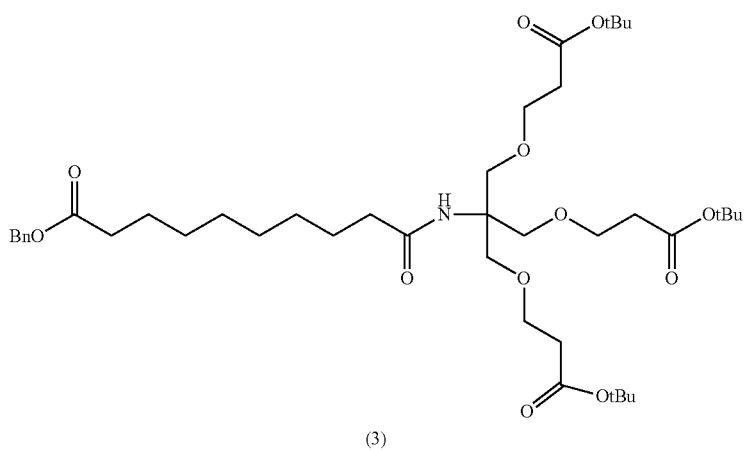
(3)
10-(Benzyloxy)-10-oxodecanoic acid (CAS no.: 67852-88-4, compound (2)) (4.80 g/16.00 mmol) was reacted with tris[[2-(tert-butoxycarbonyl)ethoxy]methyl]methylamine (CAS No.: 175724-30-8, compound (1)) (8.00 g/16.00 mmol) in the presence of DIEA (Diisopropyl Ethylamine), HBTU (Hexafluorophosphate Benzotriazole Tetramethyl Uronium) in DCM (Dichloromethane), 16 Hours, RT. Compound (3) was obtained in 70.4% yield.
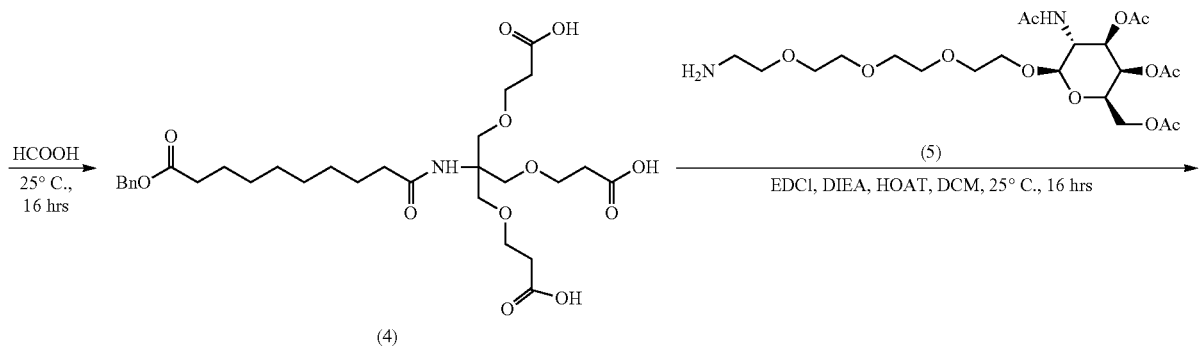
(4)

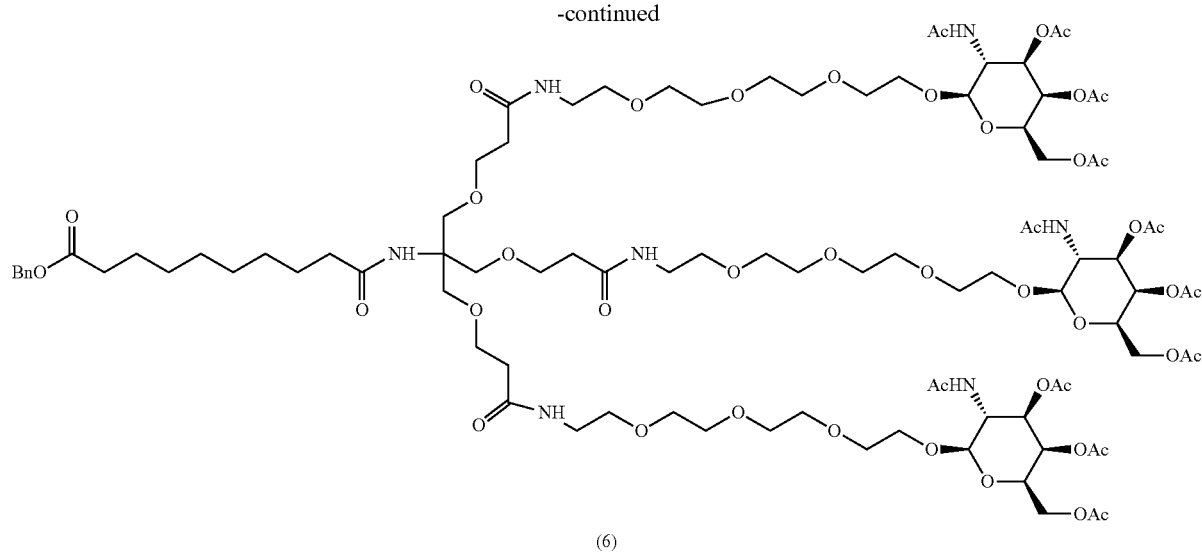

(6)

Compound (3)(9.20 g/11.80 mmol) was treated in formic acid to remove the tert.-butyl protecting groups at 25° C. for 24 hours, resulting in 86.1% yield of compound (4). The tri carboxylate compound (4) (6.90 g/11.30 mmol) was dissolved in dichloromethane with EDCI (1-Ethyl-3-(3-dimethylaminopropyl)carbodiimid), DIEA, and HOAT (1-Hydroxy-7-Azabenzotriazol). (20.00 g/38.30 mmol) [5-Acetamido-3,4-diacetyloxy-6-[2-[2-[2-(2-aminoethoxy)ethoxy]ethoxy]ethoxy]oxan-2-yl]methyl acetate (5) (preparation of compound (5) is shown below—compound (9) in Reaction Scheme 2) was added to the DCM mixture and stirred for 16 hours at 25° C. Compound (6) was afforded in 70% yield/ 97.2% purity by LCMS.

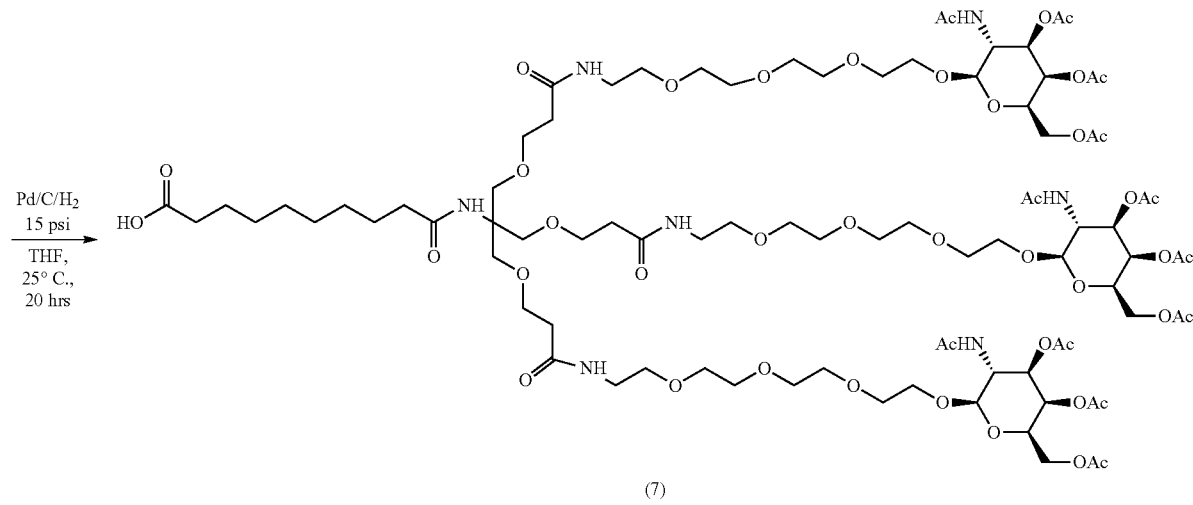 [SMILES: "Pd/C/H215 psi" ; CC(=O)N[C@H]1[C@H](OCCOCCOCCOCCNC(=O)CCOCC(COCCC(=O)NCCOCCOCCOCCO[C@@H]2O[C@H](COC(C)=O)[C@H](OC(C)=O)[C@H](OC(C)=O)[C@H]2NC(C)=O)(COCCC(=O)NCCOCCOCCOCCO[C@@H]2O[C@H](COC(C)=O)[C@H](OC(C)=O)[C@H](OC(C)=O)[C@H]2NC(C)=O)NC(=O)CCCCCCCCC(=O)O)O[C@H](COC(C)=O)[C@H](OC(C)=O)[C@@H]1OC(C)=O]

(7)

Compound (6) was dissolved in THF in the presence of Pd/C catalyst under hydrogen gas (15 psi) for 20 hours to remove the benzyl protecting group, and the crude material (7) was purified by prep HPLC to obtain compound (7).

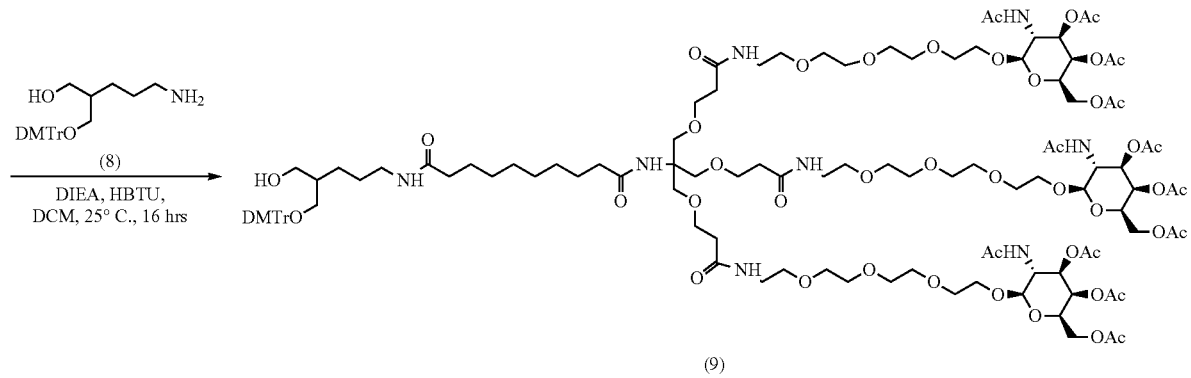

(9)

Compound (7) (0.5 g/0.25 mmol) was dissolved in DCM with DIEA and HBTU. To the mixture, compound (8)(150.0 mg/0.30 mmol)(Wuxi AppTec, Shanghai, China) was added (Dunetz et al., Org. Process Res. Dev. 2016, 20, 2, 140-177). The reaction mixture was stirred for 16 hours at 25° C. After prep HPLC purification, compound (9) was obtained at 96.3 percent purity and 41% yield.

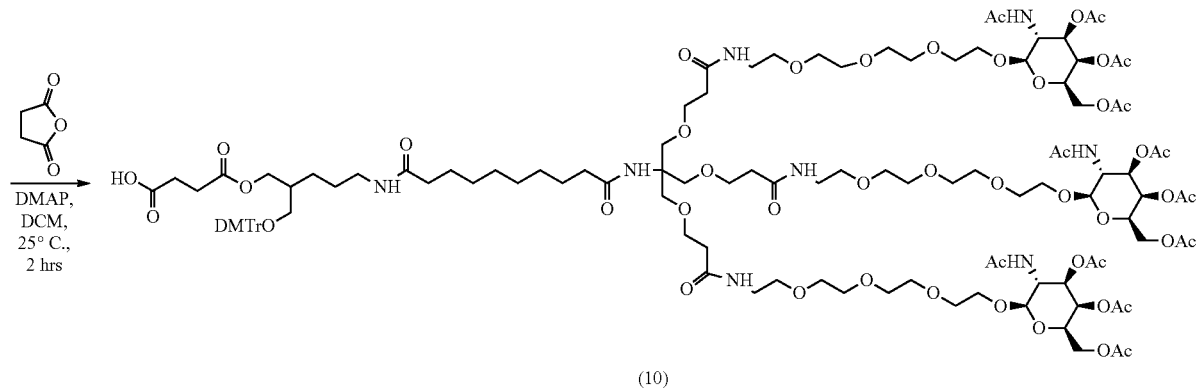

(10)

Compound (10) was made by dissolving compound (9) (380 mg/0.26 mmol) in DCM with the addition of DMAP and excess succinic anhydride affording a complete reaction.

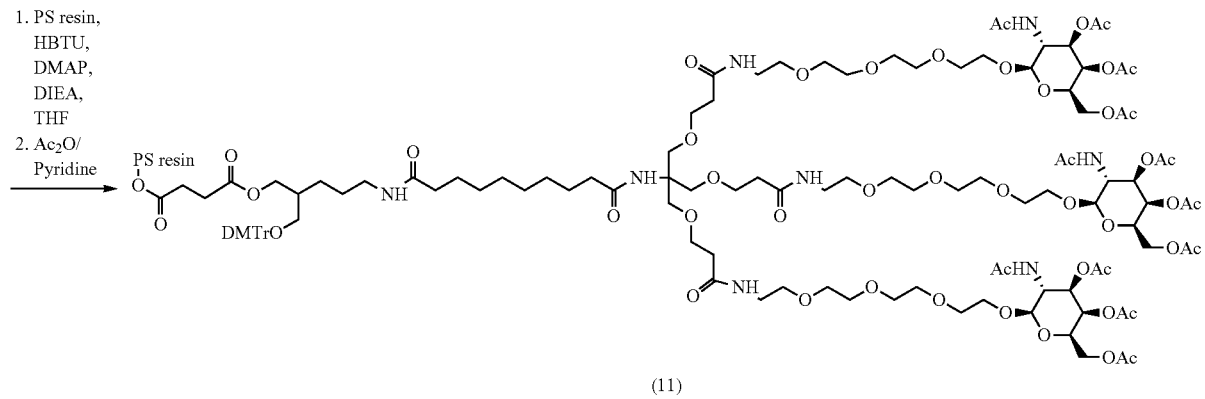

(11)

Compound (10) was coupled with both amino modified polystyrene beads using HBTU, DMAP, and DIEA in THF. The second step of the reaction used acetic anhydride with pyridine to cap any unreacted positions. The resulting loading was ~150 μmol/g. In an alternative step, compound (10) was attached to a CPG as the solid support.

Alternatives in Reaction Scheme 1:

The above described reactions may be used with minor amendments and lead to similar results.

In particular, for example, compound (8) may contain MMT(r) instead of DMT(r) as the hydroxy-protecting group. Very efficient coupling of nucleotides with MMT as the hydroxy-protecting group can be reached.

Moreover, other dicarboxylic acids anhydrides may be employed for the preparation of the spacer for the connection of the solid support. Examples of very useful dicarboxylic acids anhydrides, such as succinic anhydride, 2,2 dimethyl succinic anhydride, glutaric anhydride, adipic anhydride, 1,2 cyclohexane dicarboxylic acid anhydride, acetic anhydride ether, acetic anhydride thioether and methylimino diacetic anhydride, and their reactions with MMT-containing compound (9) are depicted below. The obtained variants of compounds 10 (compounds 10a to 10h) are further reacted to modified compound 11 (not shown) in the similar way as depicted above.

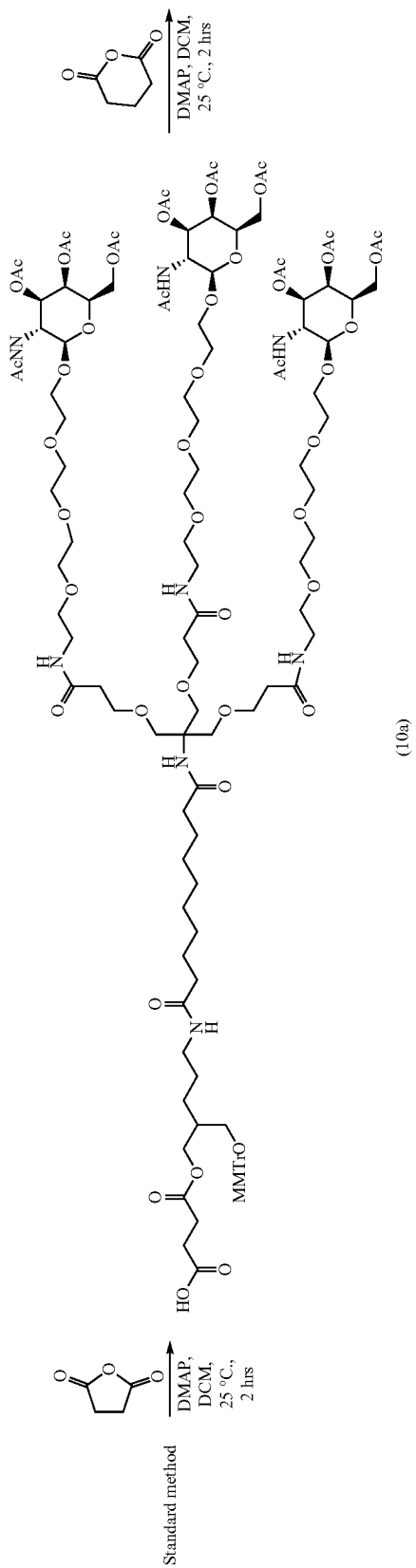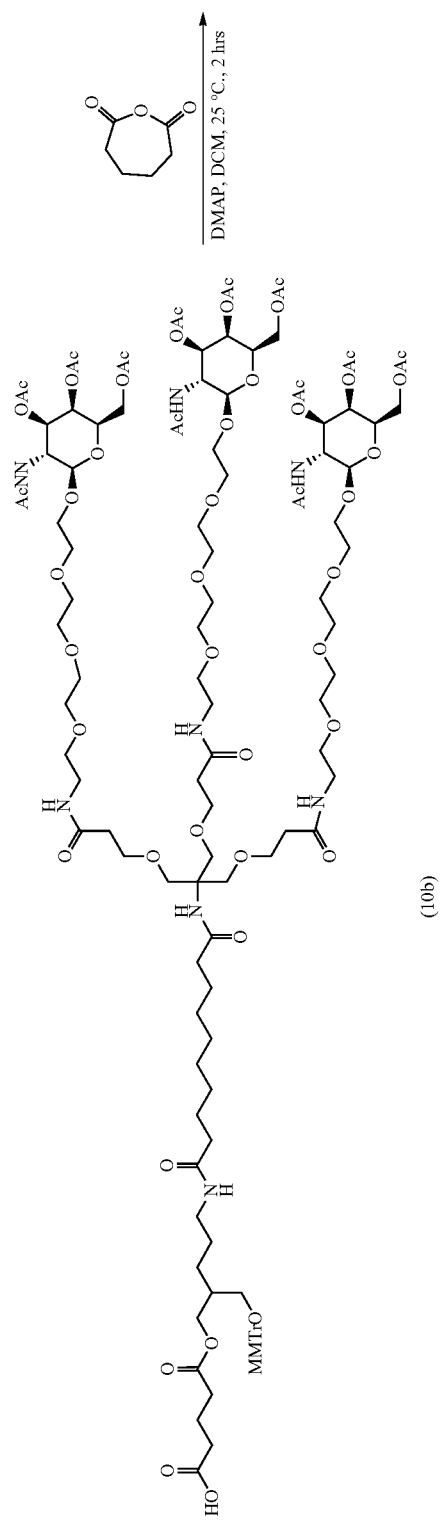

-continued
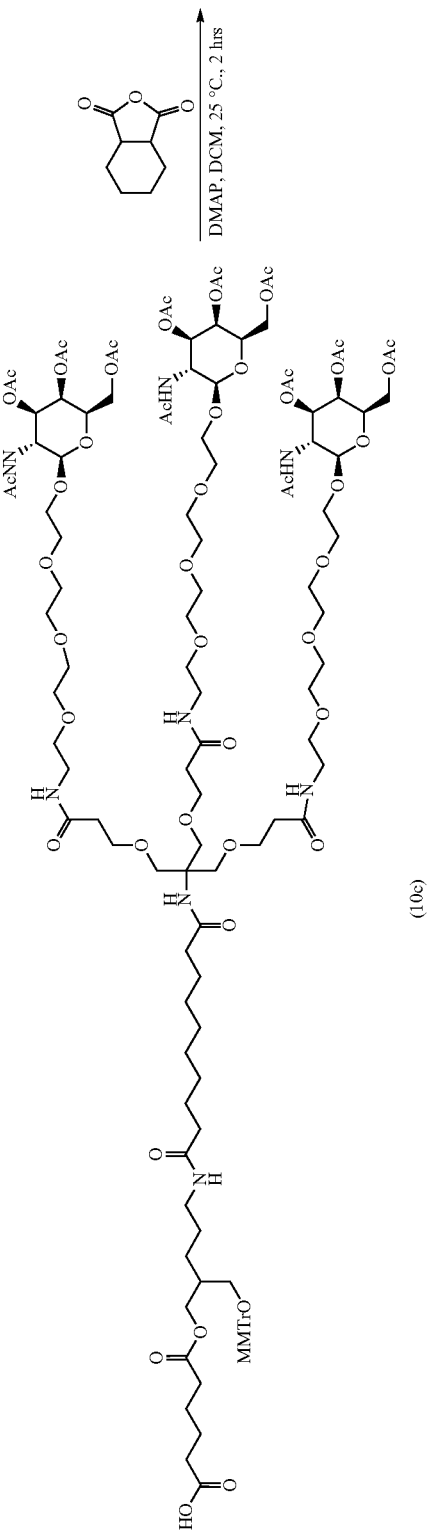
(10c)
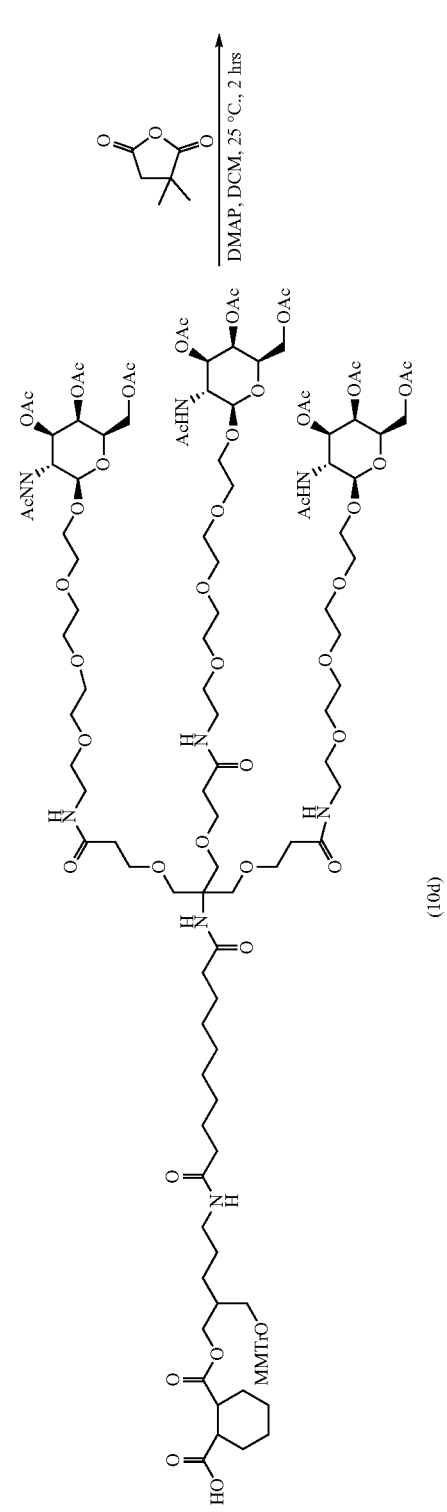
(10d)

-continued
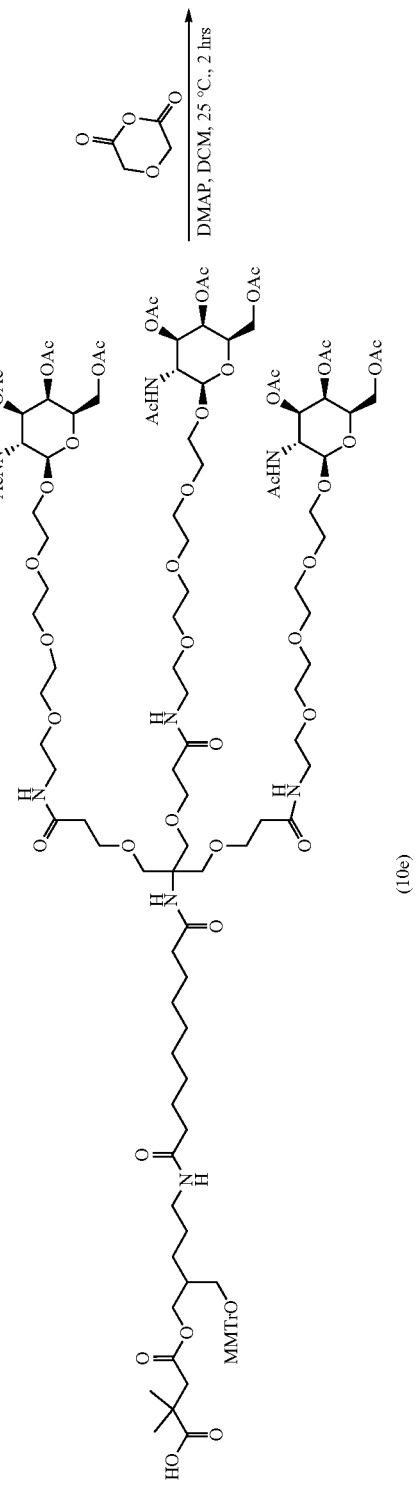
(10e)
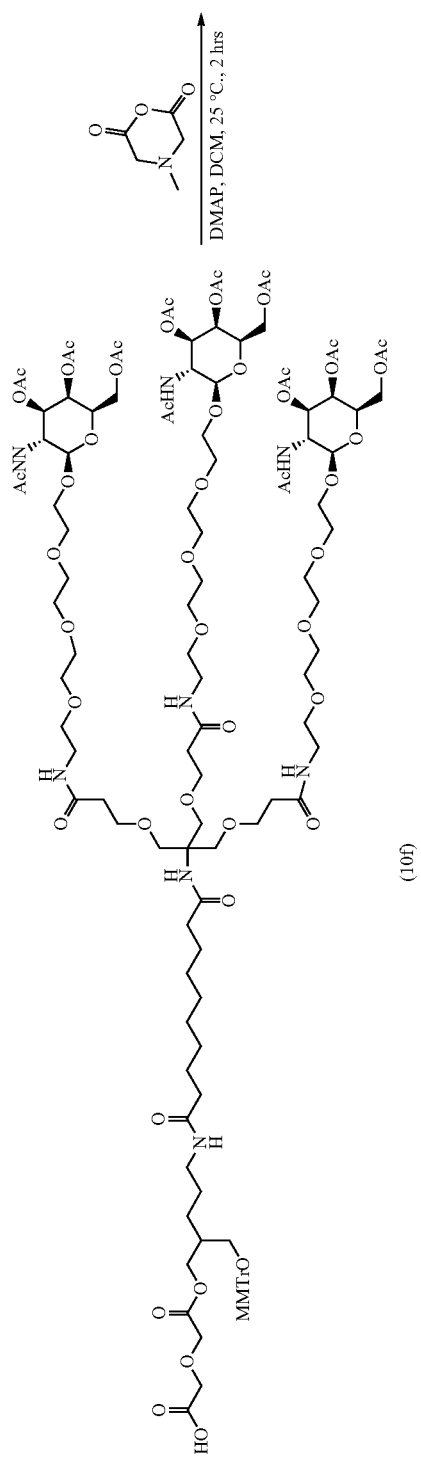
(10f)

-continued
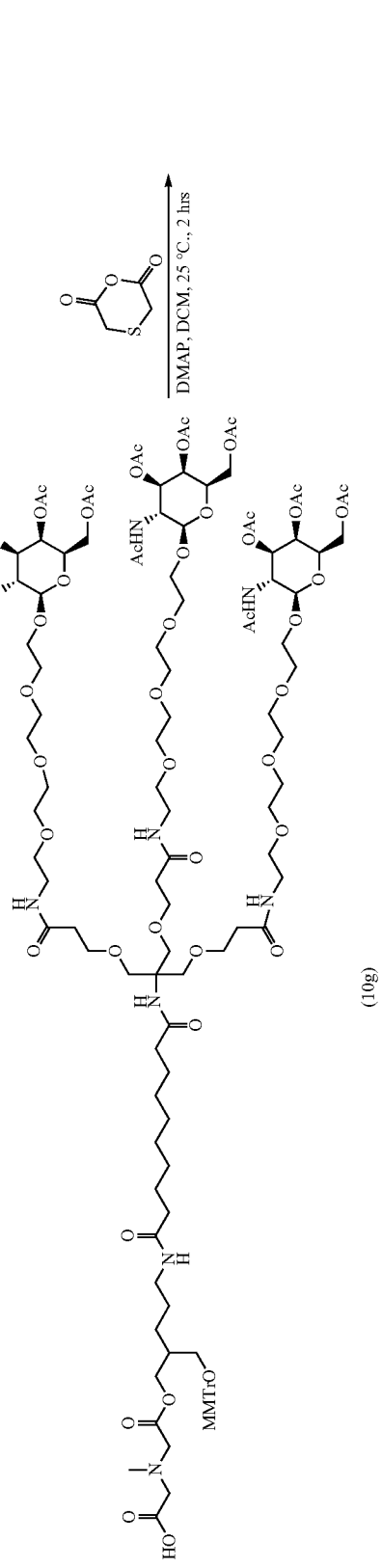
(10g)
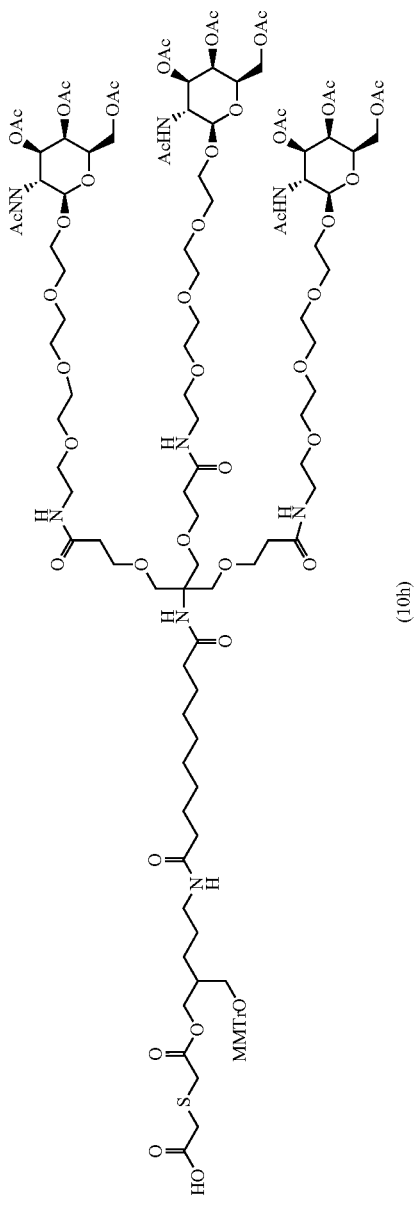
(10h)

Reaction Scheme 2
Step 1: Synthesis of an Active Trivalent Ester (5):

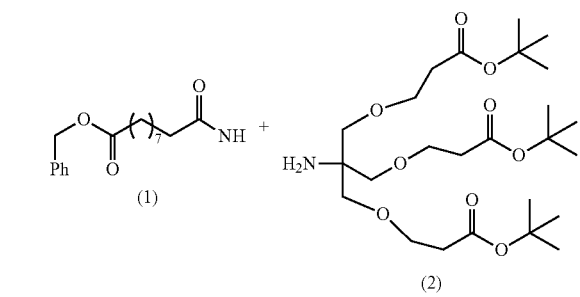

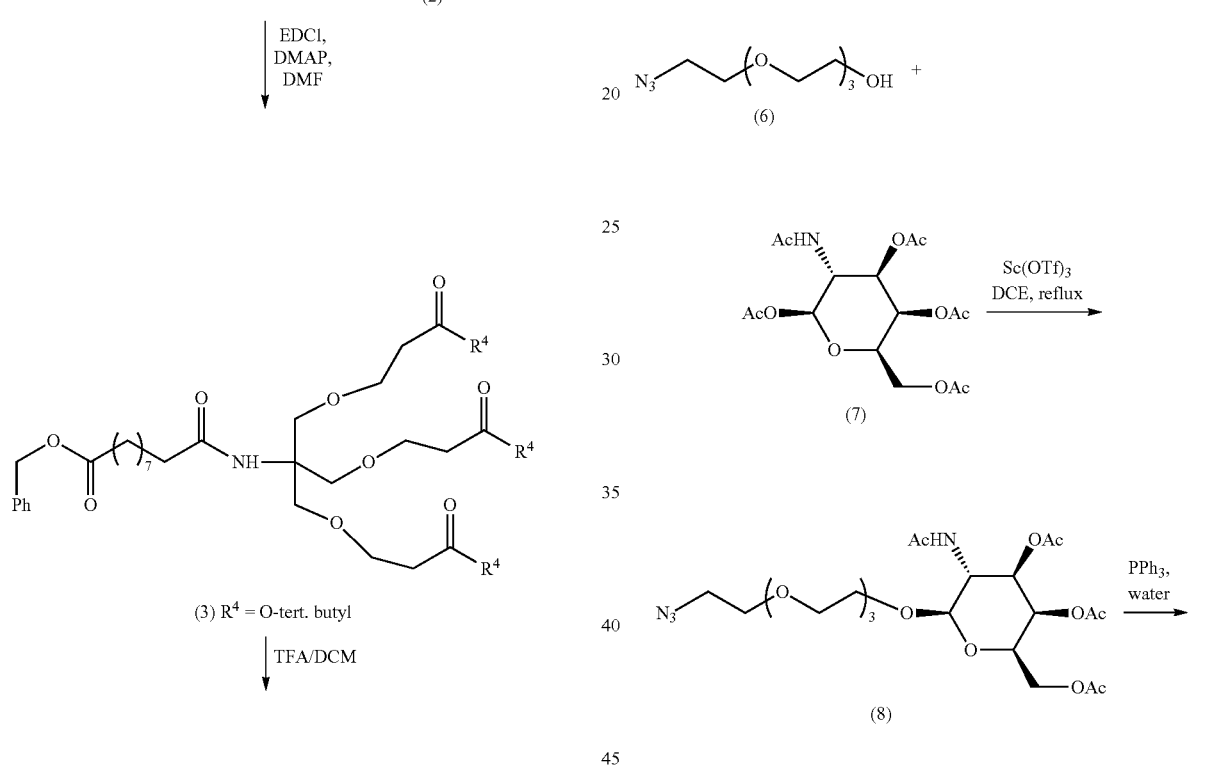

10-(Benzyloxy)-10-oxodecanoic acid (CAS no.: 67852-88-4, compound (1)) is reacted with tris[[2-(tert-butoxycarbonyl)ethoxy]methyl]methylamine (CAS No.: 175724-30-8, compound (2)) to obtain compound (3). Compound (3) is reacted to obtain compound (4) and subsequently the active trivalent ester (5) by reacting of compound (4) with pentafluorophenyl-trifluoracetate CAS No.: 14533-84-7).

Step 2: Synthesis of the Amine GalNAc Arm (9):

1-Azido-3,6,9-trioxaundecane-11-ol (CAS no.: 86770-67-4, compound (6)) is reacted with (2S,3R,4R,5R,6R)-3-acetamido-6-(acetoxymethyl)tetrahydro-2H-pyran-2,4,5-triyl triacetate (CAS No.: 3006-60-8, compound (7)) to obtain compound (8) and subsequently compound (9).

Step 3: Coupling of (5) and (9) and Subsequent Reduction of the Benzyl Group to Make the Tri-GalNAc Carboxylic Acid Moiety:
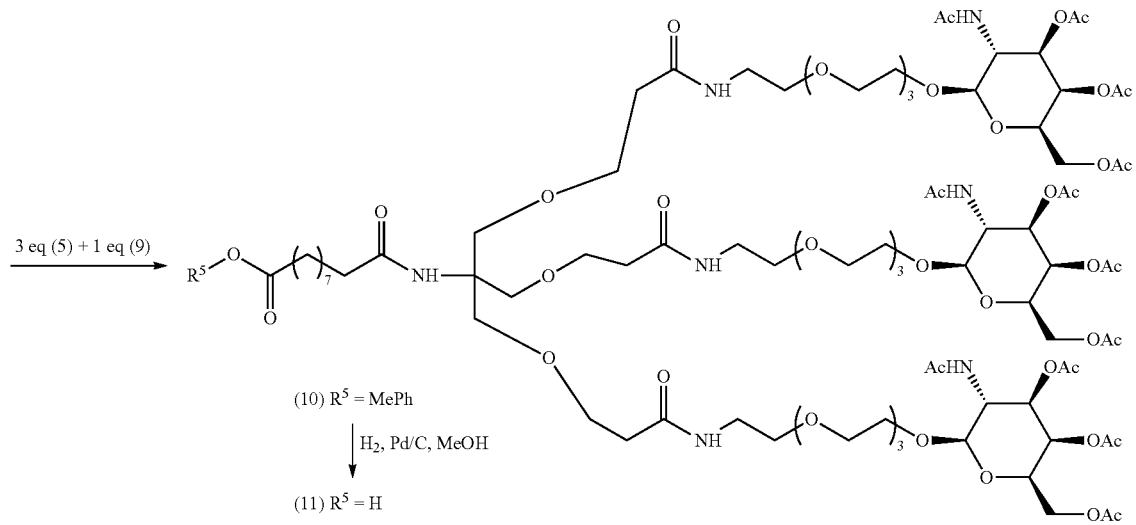
The compounds obtained in steps 1 and 2 are reacted in a 3:1 ratio of compound (5):compound (9) to obtain compound (10), which is subsequently treated as described above to give compound (11).
Step 4: Synthesis of Linker Support for Conjugation to (11):
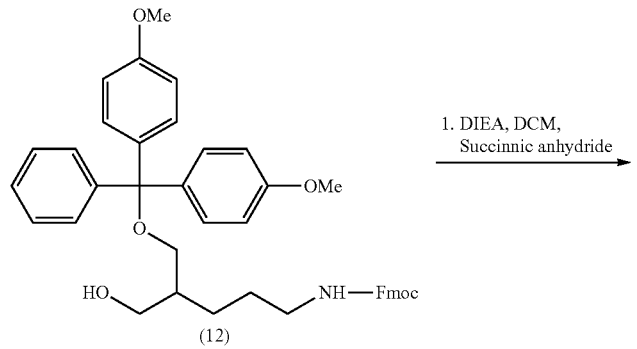
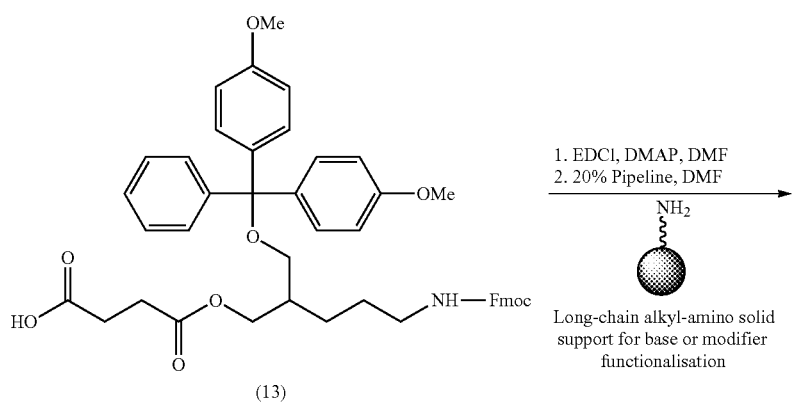

-continued

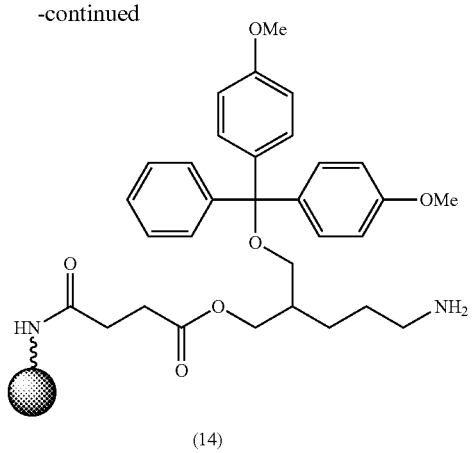

(14)

Compound (12) (Wuxi AppTec, Shanghai, China) is reacted with succinic anhydride to obtain compound (13) comprising the succinic acid spacer. Compound (13) is subsequently attached to a solid support that may be any solid support known in the art for coupling reactions, such as CPG (optionally including an LCAA spacer) and a polystyrene solid support.

Step 5: Coupling Reaction of Trivalent GalNAc (11) with Linker Modified Support (14)

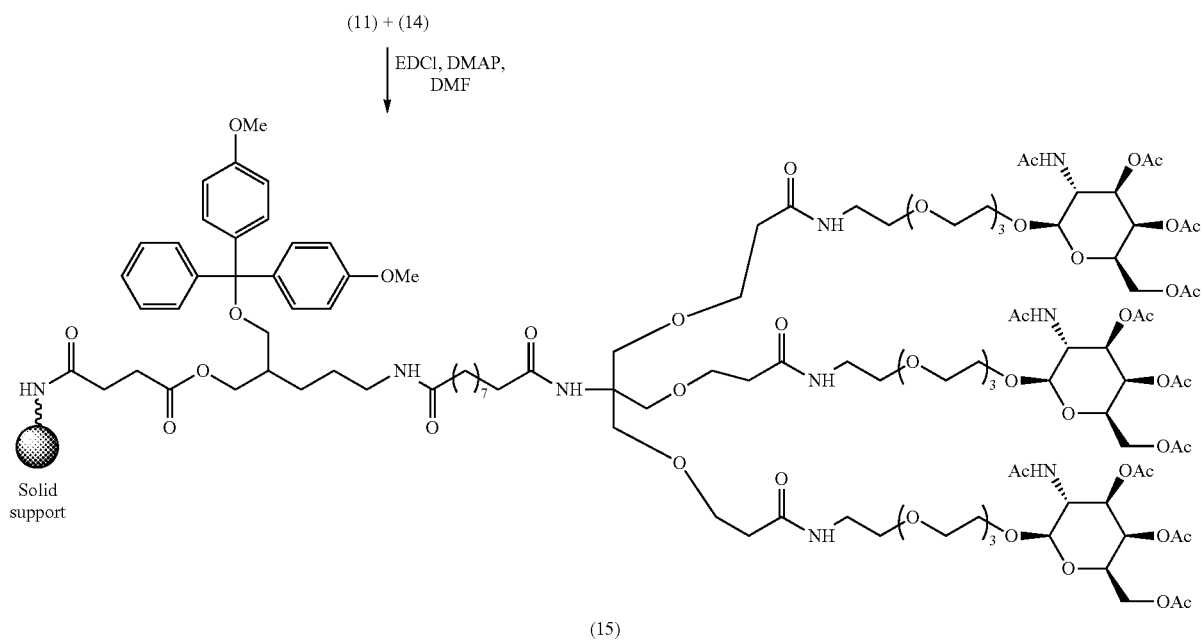

(15)

The compounds obtained in steps 3 and 4 are reacted in a 1:1 ratio of compound (11):compound (14) to obtain compound (15).

Alternatives in Reaction Scheme 2:

The above described reactions may be used with minor amendments and lead to similar results.

In particular, for example, compound (12) may contain MMT(r) instead of DMT(r) as the hydroxy-protecting group. Very efficient coupling of nucleotides with MMT as the hydroxy-protecting group can be reached.

Moreover, other dicarboxylic acids anhydrides may be employed for the preparation of the spacer for the connection of the solid support. Examples of very useful dicarboxylic acids anhydrides, such as succinic anhydride, 2,2 dimethyl succinic anhydride, glutaric anhydride, adipic anhydride, 1,2 cyclohexane dicarboxylic acid anhydride, acetic anhydride ether, acetic anhydride thioether and methylimino diacetic anhydride, and their reactions with MMT-containing compound (12) will lead to respectively modified compound (15) comprising spacer derived from these acids.

Example 2: Preparation of the GalNAc Compound Conjugate

Synthesis of Oligomeric Compound on ARNATAR GalNAc Support Oligonucleotides were attached to the ARNATAR GalNAc compound obtained as described in the Reaction Scheme 1 and having the Structure (11)—with a CPG (500 Å)-LCAA solid support.

As comparative examples, a GalNAc compound described by Sharma et al. (2018, Bioconjugate Chem, 29:2478-2488, compound 8 in Scheme 1; obtained from Gene Link, Elmsford, NY, USA or Primetech, ALC., Minsk, Belarus, as "GalNAc TEG CPG" (1000 Å) was conjugated to the same oligonucleotides.

Solid phase syntheses of oligonucleotides were done on a MerMade™ 48x synthesizer (BioAutomation, LGC, Biosearch Technologies, Hoddesdon, UK), which can make up to 48 1 µMole or 5 µMole scale oligonucleotides per run using standard phosphoramidite chemistry. Solid support is controlled pore glass (500 Å, Wuxi App Tec, Shanghai, China) loaded with 3'-GalNAc conjugates; or universal solid support (AM Chemicals, Vista, CA, USA). Ancillary synthesis reagents and standard 2'-cyanoethyl phosphoramidite monomers (2'-fluoro, 2'-O-methyl, RNA, DNA) were obtained from various sources (Hongene Biotech, Shanghai, China; Sigma-Aldrich, St. Louis, MO, USA; Glen Research, Sterling, VA, USA; ThermoFisher Scientific, Waltham, MA, USA; LGC Biosearch Technologies, Hoddesdon, UK).

Phosphoramidite mixtures were prepared in anhydrous acetonitrile or 30% DMF:acetonitrile and were coupled using 0.25M 4,5-dicyanoimidazole (DCI) (Sigma-Aldrich, St. Louis, MO, USA) with coupling times ranging from 120-360 seconds. Standard phosphodiester linkages were achieved using 0.02M iodine mixture in Tetrahydrofuran (THF), pyridine and water.

Phosphorothiate linkages were generated using 0.05M sulfurizing Reagent II (3-((Dimethylamino-methylidene) amino)-3H-1,2,4-dithiazole-3-thione, DDTT) (40:60, Pyridine/Acetonitrile) (LGC Biosearch Technologies, Hoddesdon, UK) with an oxidation time of 6 minutes. All sequences were synthesized with Dimethoxy Trityl (DMT) protecting group removed.

Upon completion of solid phase synthesis, the oligonucleotides were cleaved from the solid support and deprotection of base labile groups was performed by incubation in ammonium hydroxide at 55° C. for 6 hours. Ammonium hydroxide was removed using a centrifugal vacuum concentrator to dryness at room temperature. For sequences containing natural ribonucleotides (2'-OH) protected with tert-butyl dimethyl silyl (TBDMS), a second deprotection was performed using triethylamine; trihydrofluoride (TEA: 3HF). To each TBDMS protected oligonucleotide 100 µL DMSO and 125 µL TEA:3HF was added and incubated at 65° C. for 2.5 hours. After incubation 25 µL of 3M sodium acetate was added to the solution which was subsequently precipitated in butanol at −20'C for 30 minutes. The cloudy solution was centrifuged to a cake at which time the supernatant was carefully decanted with a pipette. The standard precipitation process was then completed with 75% ethanol:water then 100% ethanol as supernatant solutions. The oligonucleotide cake was dried for 30 minutes in a centrifugal vacuum concentrator.

Desalting without HPLC purification was performed after precipitation with 3M sodium acetate with a follow on G25 Sephadex® column (Sigma-Aldrich, St. Louis, MO, USA) elution. Purification of oligonucleotides was afforded by anion exchange chromatography on a Gilson GX271 prep HPLC system (Middleton, WI, USA) using BioWorks Q40 resin (Uppsala, Sweden). Final desalt was performed by Sephadex® G25 column. All oligonucleotides were analyzed by ion pairing reverse phase HPLC for purity using an Agilent 1200 analytical HPLC (Santa Clara, CA, USA), negative ion mass spectrometry for intact mass on an Agilent 6130 single quad mass spectrometer (Santa Clara, CA, USA), and A260 quantification by UV/V is on a Tecan Infinite® M Plex plate reader (Zurich, Switzerland).

A GalNAc conjugated oligonucleotide can be used alone as a single stranded compound (e.g., antisense oligonucleotide (ASO), ssRNA, or miRNA; e.g., Example 3) or in a duplex to form a double stranded compound (e.g., siRNA and/or shRNA). In some examples (e.g., Examples 4 and 5, the GalNAc was conjugated to the sense strand of a double stranded compound.

Double Stranded Oligomeric Compound Duplex Formation

In general, for a double stranded oligomeric compound such as a siRNA compound, a sense and antisense oligonucleotide is annealed together to form a duplex. Duplex formation of 50-300 mM can be achieved by heating samples at 94° C. for 4 mins in 1× phosphate-buffered saline in a block heater, followed by removal of the heating block containing the samples from the block heater and allowing it to gradually cool down to room temperature over a time course of 1 hour.

Example 3: Stability of ARNATAR GalNAc Conjugate

The ARNATAR GalNAc compound and Sharma GalNAc compound conjugates were prepared as described in Example 2 and comprised the oligonucleotides depicted in Table 1. They were assessed for stability and durability.

Four oligonucleotides were synthesized in total at 1 µmol scale. Two 24-mer poly-T oligonucleotides were synthesized with standard phosphodiester using Sharma GalNAc or ARNATAR GalNAc supports. Two 24-mer poly-T oligonucleotides were synthesized with phosphorothioate (PS) internucleoside chemistry (denoted by * between the nucleosides) using Sharma GalNAc or ARNATAR GalNAc supports. All four oligonucleotides were purified using standard synthesis methods and ion exchange purification. Analytical HPLC showed that all four oligonucleotides had greater than 90% purity after purification and desalting.

TABLE 1

GalNAc Conjugated Oligonucleotide Constructs

| Name | Compound | SEQ ID NO: |
|---|---|---|
| Construct 1 | TTTTTTT TTTTTT-(Sharma GalNAc) | 1 |
| Construct 2 | TTTTTT TTTTTTT-(ARNATAR GalNAc) | 1 |
| Construct 3 | T*T*T*T*T*T*T*T*T*T*T*T*T*T*T*T*T*T*T*T*T*T*T*T-(Sharma GalNAc) | 2 |
| Construct 4 | T*T*T*T*T*T*T*T*T*T*T*T*T*T*T*T*T*T*T*T*T*T*T*T-(ARNATAR GalNAc) | 2 |

Samples of each GalNAc conjugated oligonucleotide constructs in water (~500 uM) where combined with either AMA (Ammonium Hydroxide/40% aqueous Methylamine 1:1 v/v) or 300 mM NaAc (Sodium acetate) buffer pH 4.5. Table 2 displays the comparative stability of the two GalNAc oligonucleotide conjugates. Herein, rows 2 and 3 depict the results obtained for stability measurements of the linkage between the respective GalNAc compound and the oligonucleotide, while rows 4 and 5 depict the results obtained for stability measurements within the oligonucleotides.

TABLE 2

GalNAc Stability

| Construct | moiety tested | 30% Ammonium hydroxide 25° C. (24 h) | 40% AMA 55° C. (24 h) | 40% AMA 55 C. (72 h) | pH 4.5/0.3M NaAc 25° C. (24 h) | pH 4.5/0.3M NaAc 55° C. (24 h) |
|---|---|---|---|---|---|---|
| 2, 4 | ARNATAR GalNAc | Stable | Stable | Stable | Stable | Stable |
| 1, 3 | Sharma GalNAc | Stable | Stable | Stable | Stable | Stable |
| 3, 4 | T24 PS Oligo | Stable | Mild degradation (−320, −640 Mw) | degradation | Stable | Mild degradation |
| 1, 2 | T24 Oligo | Stable | Mild degradation (−320, −640 Mw) | degradation | Stable | Mild degradation |

The reactions were analyzed by mass spectrometry to determine if cleavage products were present. In all cases in which degradation was observed, cleavage of phosphodiester and phosphorothioate linkage were the primary truncation products. Analysis with a result of mild degradation showed some N-1 and N-2 products. Analysis with a result of degradation showed a majority of full-length product was reduced to monomers. Under both acidic and basic conditions, the oligonucleotides phosphate linkages began to degrade before any GalNAc degradation products could be observed. ARNATAR GalNAc was found to be stable under stressful conditions.

Example 4: ARNATAR GalNAc Assessment in Human Primary Hepatocytes

The ARNATAR GalNAc compound and Sharma GalNAc compound conjugates were prepared as described in Example 2, wherein the GalNAc compounds were conjugated to the same siRNA compound (ATsi103) targeting Laminin (LMNA) on the sense strand of the duplex as shown in Table 3.

The GalNAc conjugated LMNA siRNAs were incubated with human primary hepatocytes to allow free uptake (i.e., cell entry without transfection) of the GalNAc-siRNA compound into the cells. Knockdown of LMNA expression was used as a marker to assess the ability of each GalNAc type to transport the siRNA targeting LMNA into the hepatocytes.

Varying doses of each LMNA siRNA (0 µM, 0.008 µM, 0.04 µM, 0.2 µM, 1 µM or 5 µM final concentrations) were added to human primary hepatocytes (HPH) (Xenotech, Kansas City, KS, USA) and incubated at 37° C. and 5% CO2 for 16 hours, 31 hours or 51 hours. siRNA activity was determined by measuring the levels of target mRNA through qRT-PCR using the LMNA primer probe set listed in Table 4. qRT-PCR was performed using AgPath-ID™ One-Step RT-PCR Reagents in QS3 real-time PCR system (ThermoFisher Scientific, Waltham, MA, USA). The target RNA levels detected in qRT-PCR assay were normalized to either total RNA levels measured with Ribogreen™ (ThermoFisher Scientific, Waltham, MA, USA) or GAPDH mRNA levels detected in the aliquots of RNA samples using qRT-PCR.

TABLE 3

LMNA siRNAs

| siRNA Name | GalNAc | Sense or Antisense | Sequence + Chemistry (5' to 3') | Sequence | SEQ ID NO: |
|---|---|---|---|---|---|
| ATsi103-AN | Arnatar GalNAc | Sense | mG*fC*mGmUfCmAfCmC fAfAmAmAfAmGfCmGmC fAmA*T*T-GalNAc-AN | GCGUCACCAAA AAGCGCAATT | 6 |
| | none | Antisense | (5p)mU*T*mGfCmGfCT* mUfUmUmUfGmGfUmGf AmCmGC*mU*mU | UTGCGCTUUUU GGUGACGCUU | 7 |
| ATsi103-GL | Sharma GalNAc | Sense | mG*fC*mGmUfCmAfCmC fAfAmAmAfAmGfCmGmC fAmA*T*T-GalNAc GL | GCGUCACCAAA AAGCGCAATT | 6 |
| | none | Antisense | (5p)mU*T*mGfCmGfCT* mUfUmUmUfGmGfUmGf AmCmGC*mU*mU | UTGCGCTUUUU GGUGACGCUU | 7 |

(5p) = 5'-phosphate
d (or no notation made before a nucleotide) = deoxyribonucleotide which has been substituted for a ribonucleotide
f = 2'-F
m = 2'-OMe
* = phosphorothioate (PS) linkage
GalNAc-AN = ARNATAR GalNAc
GalNAc-GL = Sharma GalNAc The percent LMNA mRNA at 51 hrs after free uptake of GalNAc conjugated siRNAs by HPH is shown in FIG. 1. The time course of changes in LMNA mRNA level is shown in FIG. 2. A mock PBS treatment was used as a control.

TABLE 4

Human LMNA Primer-Probe Set

| Primer Name | Primer Sequence (5' to 3') | SEQ ID NO: |
|---|---|---|
| hsLMNA-S | CGGGTGGATGCTGAGAAC | 3 |
| hsLMNA-A | TGCTTCCCATTGTCAATCTCC | 4 |
| hsLMNA-P | AGTGAGGAGCTGCGTGAGACCAA | 5 |

TABLE 5

GalNAc Conjugated siRNA Activity Targeting LMNA in Human Primary Hepatocytes

| siRNA Name | % LMNA mRNA Remaining After Addition of 5 μM GalNAc Conjugated siRNA to HPH | | |
|---|---|---|---|
| | 16 hr | 31 hr | 51 hr |
| Control | 100.00 | 100.00 | 100.00 |
| ATsi103-AN | 66.04 | 40.69 | 29.45 |
| ATsi103-GL | 95.55 | 67.29 | 75.53 |

The ARNATAR GalNAc compound is a novel GalNAc compound that provides enhanced activity over the GalNAc compound previously disclosed by Sharma. As shown by this study, ARNATAR GalNAc conjugate performed better than the Sharma GalNAc in human primary hepatocytes for all doses and times assessed. It is unexpected that the ARNATAR GalNAc conjugate performed so much better than the Sharma GalNAc conjugate given the minor difference in structure.

Example 5: ARNATAR GalNAc Conjugate Assessment in Mouse Hepatocytes

The GalNAc conjugated LMNA siRNAs disclosed in Example 4 target both human and mouse LMNA mRNAs, so, a study was performed to confirm the ability of ARNATAR GalNAc in delivering siRNA into mouse hepatocytes.

In this study, the GalNAc conjugated LMNA siRNAs were incubated with mouse hepatocytes to allow free uptake (i.e., cell entry without transfection) of the GalNAc-siRNA compound into the cells. As in Example 4, knockdown of LMNA expression was used as a marker to assess the ability of each GalNAc to transport the siRNA targeting LMNA into the hepatocytes.

Varying doses of each LMNA siRNA (0 μM, 0.008 μM, 0.04 μM, 0.2 μM, 1 μM or 5 μM final concentrations) were added to mouse hepatocytes (mHP) (Xenotech, Kansas City, KS, USA) and incubated at 37° C. and 5% CO2 for 60 hours. siRNA activity was determined by measuring the levels of target mRNA through qRT-PCR using the LMNA primer probe set listed in Table 6. qRT-PCR was performed using AgPath-ID™ One-Step RT-PCR Reagents in QS3 real-time PCR system (ThermoFisher Scientific, Waltham, MA, USA). The target RNA levels detected in qRT-PCR assay were normalized to either total RNA levels measured with Ribogreen™ (ThermoFisher Scientific, Waltham, MA, USA) or GAPDH mRNA levels detected in the aliquots of RNA samples using qRT-PCR.

The percent LMNA mRNA at 60 hrs after free uptake of GalNAc conjugated siRNAs by HPH is shown in FIG. 3.

TABLE 6

Mouse LMNA Primer-Probe Set

| Primer Name | Primer or Probe Sequence (5' to 3') | SEQ ID NO: |
|---|---|---|
| msLMNA-Forward | GGA CCA GGT GGAACA GTA TAA G | 8 |
| msLMNA-Reverse | TCA ATG CGG ATT CGA GAC TG | 9 |
| msLMNA-Probe | 56-FAM/CAG CTT GGC/ZEN/GGA GTA TGT CTT TTC TAG C/3IABKFQ* | 10 |

*56-FAM, ZEN, and /3IABKFQ are dyes used in the oligo

Example 6: ARNATAR GalNAc Assessment In Vitro

The ARNATAR GalNAc compound and Sharma GalNAc compound conjugates were prepared as described in Example 2, wherein the GalNAc compounds were conjugated to the same siRNA compound targeting proprotein convertase subtilisin/kexin type 9 (PCSK9) on the sense strand of the duplex as shown in Table 7.

TABLE 7

PCSK9 siRNAs

| siRNA Name | GalNAc | Sense or Antisense | Sequence + Chemistry (5' to 3') | Sequence | SEQ ID NO: |
|---|---|---|---|---|---|
| PCSK9-si10 (ATXL055AN + ATXL054) | none | Antisense | (5p)mU*fG*mAmCmUfUmU fGfCmAmUmUmCfCmAfG mAmCmC*T*T | UGACUUUGCA UUCCAGACCTT | 11 |
|  | ARNATAR GalNAc | Sense | mG*mG*mUmCmUmGfGm AfAfUfGmCmAmAmAmGm UmCmA*T*T-GalNAc-AN | GGUCUGGAAU GCAAAGUCAT T | 12 |
| PCSK9-si11 (ATXL055GL + ATXL054) | none | Antisense | (5p)mU*fG*mAmCmUfUmU fGfCmAmUmUmCfCmAfG mA mCmC*T*T | UGACUUUGCA UUCCAGACCTT | 11 |
|  | Sharma GalNAc | Sense | mG*mG*mUmCmUmGfGm AfAfUfGmCmAmAmAmGm UmCmA*T*T-GalNAc-GL | GGUCUGGAAU GCAAAGUCAT T | 12 |

(5p) = 5'-phosphate
d (or no notation made before a nucleotide) = deoxyribonucleotide which has been substituted for a ribonucleotide
f = 2'F
m = 2'-OMe
* = phosphorothioate (PS) linkage
GalNAc-AN = ARNATAR GalNAc
GalNAc-GL = Sharma GalNAc

TABLE 8

Human PCSK9 Primer-Probe Set

| Primer Name | Primer Sequence (5' to 3') | SEQ ID NO: |
|---|---|---|
| PCSK9 Forward Primer | TCACCAAGATCCTGCATGTC | 13 |
| PCSK9 Reverse Primer | GTTCCACGGGATGCTCTG | 14 |
| PCSK9 Probe | 56-FAM/CAGGTCGCC/ZEN/ACTCATCTTCACCA/3IABKFQ* | 15 |

*56-FAM, ZEN, and /3IABKFQ are dyes used in the oligo

In Vitro Assessment in Human Primary Hepatocytes

The GalNAc conjugated PCSK9 siRNAs were incubated with human primary hepatocytes to allow free uptake (i.e., cell entry without transfection) of the GalNAc-siRNA conjugate into the cells. Knockdown of PCSK9 expression was used as a marker to assess the ability of each GalNAc type to transport the siRNA targeting PCSK9 into the hepatocytes.

Varying doses of each PCSK9 siRNA (0 μM, 0.001 μM, 0.01 μM, 0.1 μM, 1 μM or 10 μM final concentrations) were added to human primary hepatocytes (HPH) (Xenotech, Kansas City, KS, USA) and incubated at 37° C. and 5% $CO_2$ for 4 days. siRNA activity was determined by measuring the levels of target mRNA through qRT-PCR using the PCSK9 primer probe set listed in Table 8. qRT-PCR was performed using AgPath-ID™ One-Step RT-PCR Reagents in QS3 real-time PCR system (ThermoFisher Scientific, Waltham, MA, USA). The target RNA levels detected in qRT-PCR assay were normalized to either total RNA levels measured with Ribogreen™ (ThermoFisher Scientific, Waltham, MA, USA) or GAPDH mRNA levels detected in the aliquots of RNA samples using qRT-PCR.

The percent PCSK9 mRNA at 4 days after free uptake of GalNAc conjugated siRNAs by HPH is shown in FIG. 4. A mock PBS treatment was used as a control.

CONCLUSION

The ARNATAR GalNAc compound is a novel GalNAc compound that provides enhanced activity over the GalNAc compound previously disclosed by Sharma et al., As shown by this study, ARNATAR GalNAc conjugate performed better than the Sharma GalNAc conjugate in human primary hepatocytes for all doses and times assessed. It is unexpected that the ARNATAR GalNAc conjugate performed so much better than the Sharma GalNAc conjugate given the minor difference in structure.

TABLE 9

Sequence Listing

| Sequence Name | Sequence (5' to 3') | SEQ ID NO |
|---|---|---|
| Construct 1 and 2 | TTTTTTTTTTTTTTTTTTTTTTTT-GalNAc | 1 |
| Construct 3 and 4 | T*T*T*T*T*T*T*T*T*T*T*T*T*T*T*T*T*T*T*T*T*T*T*T-GalNAc | 2 |
| hsLMNA-S | CGGGTGGATGCTGAGAAC | 3 |
| hsLMNA-A | TGCTTCCCATTGTCAATCTCC | 4 |
| hsLMNA-P | AGTGAGGAGCTGCGTGAGACCAA | 5 |
| ATsi103-AN or ATsi103GL sense strand | mG*fC*mGmUfCmAfCmCfAfAmAfAmGfCmGmCfAmA*T*T-GalNAc | 6 |
| ATsi103-AN or ATsi103GL antisense strand | (5p)mU*T*mGfCmGfCT*mUfUmUfGmGfUmGfAmCmGC*mU*mU | 7 |
| msLMNA-Forward | GGACCAGGTGGAACAGTATAA G | 8 |
| msLMNA-Reverse | TCAATGCGGATTCGAGACTG | 9 |
| msLMNA-Probe | 56-FAM/CAG CTT GGC/ZEN/GGA GTA TGT CTT TTC TAG C/3IABKFQ* | 10 |
| ATXL054 | (5p)mU*G*mAmCmUfUmUfGfCmAmUmUmCfCmAfGmAmCmC*T*T | 11 |
| ATXL055AN or ATXL055GL | mG*mG*mUmCmUmGfGmAfAfUfCmCmAmAmAmGmUmCmA*T*T-GalNAc | 12 |
| PCSK9 Forward Primer | TCACCAAGATCCTGCATGTC | 13 |
| PCSK9 Reverse Primer | GTTCCACGGGATGCTCTG | 14 |
| PCSK9 Probe | 56-FAM/CAGGTCGCC/ZEN/ACTCATCTTCACCA/3IABKFQ* | 15 |
| ATsi103 sense strand | GCGUCACCAAAAAGCGCAAUU | 16 |
| ATsi103 antisense strand | UTGCGCUUUUUGGUGACGCUU | 17 |
| ATXL054 | UGACUUUGCAUUCCAGACCTT | 18 |
| ATXL055 | GGUCUGGAAUGCAAAGUCATT | 19 |

---

What is claimed:
1. A compound having the structure of formula (0a), (Ia) or (IIa):
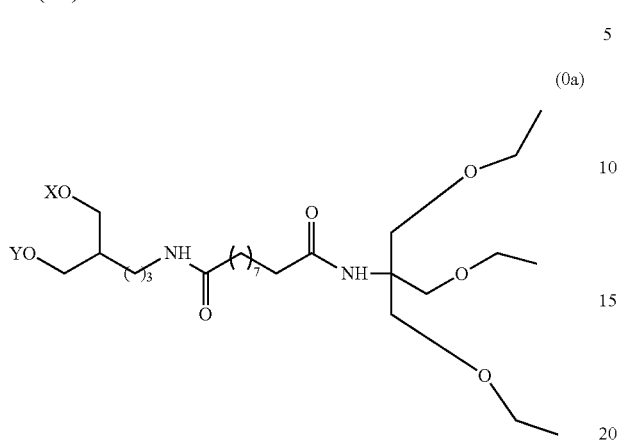
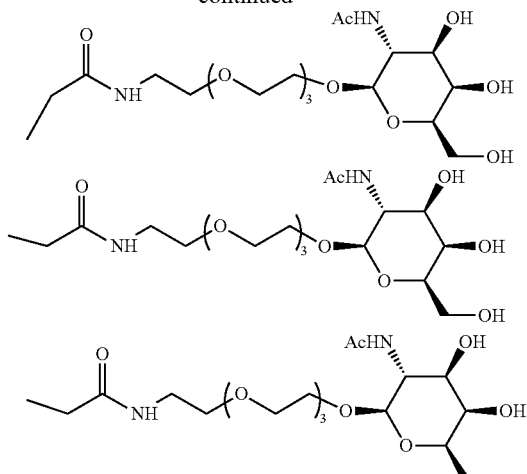
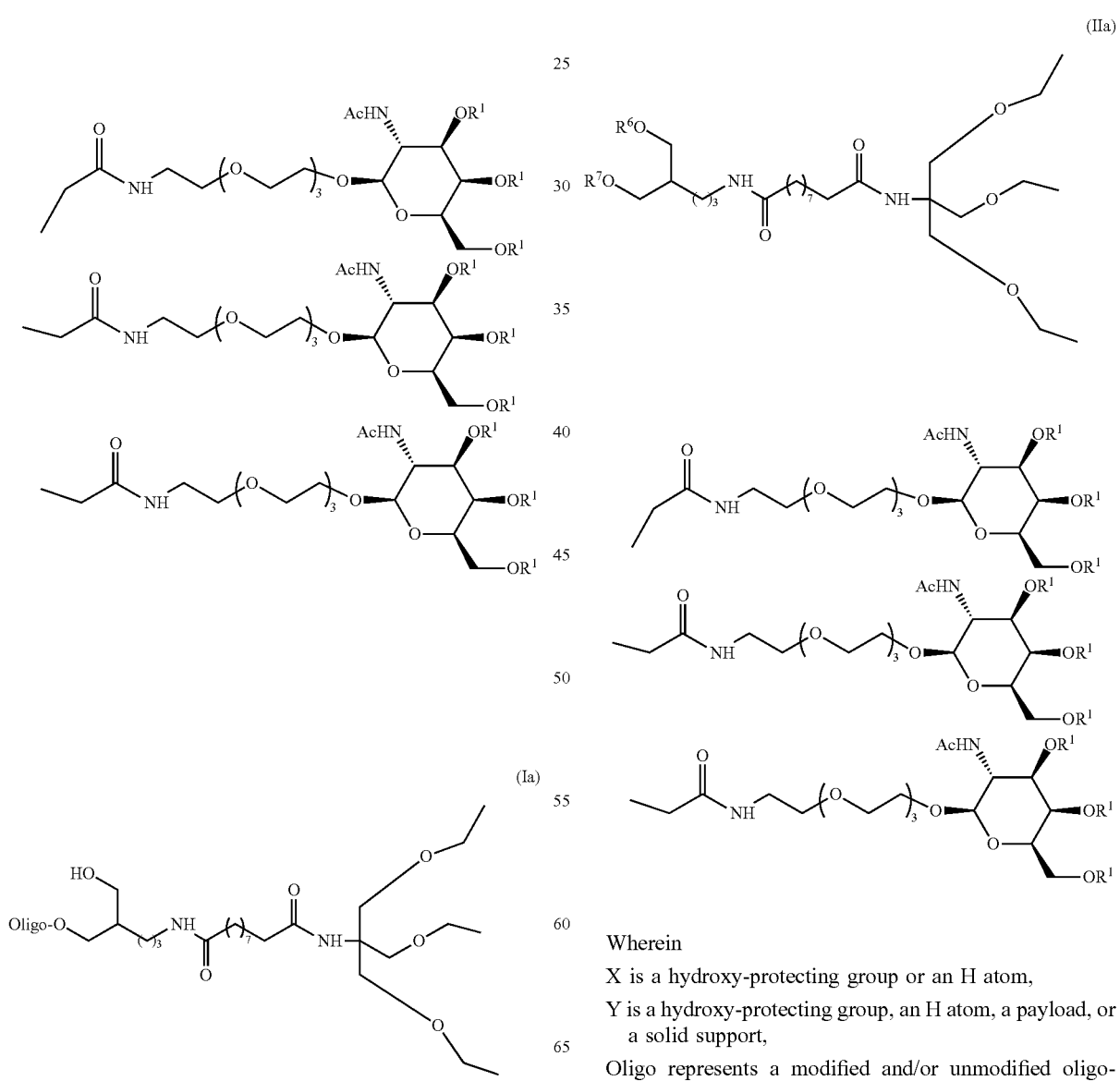
Wherein
X is a hydroxy-protecting group or an H atom,
Y is a hydroxy-protecting group, an H atom, a payload, or a solid support,
Oligo represents a modified and/or unmodified oligonucleotide

$R^1$ is selected from any of hydroxy-protecting groups and H atom,
$R^6$ represents a hydroxy-protecting group, and
$R^7$ represents a moiety of formula (VI):

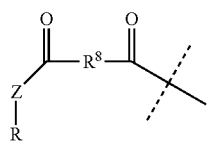

(VI)

wherein in R7
R represents a solid support, an amino-protecting group, a hydroxy-protecting group, or an H atom,
Z represents NH or O, and
$R^8$ represents a linear or branched alkylene having from 1 to 8 carbon atoms and/or a cycloalkylene having from 5 to 8 carbon atoms.

2. The compound of claim 1, wherein when Y is a payload or a solid support it is connected to the compound via a spacer.

3. The compound of claim 1, wherein in $R^6$, the hydroxy-protecting group is a DMT or MMT.

4. The compound of claim 3, wherein the hydroxy-protecting group of $R^6$ is MMT.

5. The compound of claim 1, wherein when R represents a solid support, it is connected to the compound via a spacer.

6. The compound of claim 1, wherein in $R^8$ one or more carbon atoms are substituted by an O, S, NH and/or N—($C_1$-$C_3$ alkyl) and/or a cycloalkylene having from 5 to 8 carbon atoms.

7. The compound of claim 6, wherein the cycloalkylene having from 5 to 8 carbon atoms is any of ethylene, 1,1-dimethyl ethylene, propylene, n-butylene or 1,2-cyclohexylene.

8. A pharmaceutical composition comprising the compound of claim 1 and a pharmaceutically acceptable carrier, excipient, and/or diluent.

* * * * *

SEQUENCE LISTING

Sequence total quantity: 19
SEQ ID NO: 1     moltype = DNA  length = 24
FEATURE          Location/Qualifiers
source            1..24
                  mol_type = other DNA
                  organism = synthetic construct

```
misc_feature            24
                        note = 3'-O attached to a GalNAc-comprising compound via a
                         linker
SEQUENCE: 1
tttttttttt tttttttttt tttt                                              24

SEQ ID NO: 2            moltype = DNA  length = 24
FEATURE                 Location/Qualifiers
source                  1..24
                        mol_type = other DNA
                        organism = synthetic construct
misc_feature            24
                        note = 3'-O attached to a GalNAc-comprising compound via a
                         linker
modified_base           2..24
                        mod_base = OTHER
                        note = 5'-thiophosphate
SEQUENCE: 2
tttttttttt tttttttttt tttt                                              24

SEQ ID NO: 3            moltype = DNA  length = 18
FEATURE                 Location/Qualifiers
source                  1..18
                        mol_type = other DNA
                        organism = synthetic construct
SEQUENCE: 3
cgggtggatg ctgagaac                                                     18

SEQ ID NO: 4            moltype = DNA  length = 21
FEATURE                 Location/Qualifiers
source                  1..21
                        mol_type = other DNA
                        organism = synthetic construct
SEQUENCE: 4
tgcttcccat tgtcaatctc c                                                 21

SEQ ID NO: 5            moltype = DNA  length = 23
FEATURE                 Location/Qualifiers
source                  1..23
                        mol_type = other DNA
                        organism = synthetic construct
SEQUENCE: 5
agtgaggagc tgcgtgagac caa                                               23

SEQ ID NO: 6            moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methyl guanosine
modified_base           2
                        mod_base = OTHER
                        note = 2'-fluoro cytidine 5'-thiophosphate
modified_base           3
                        mod_base = OTHER
                        note = 2'-O-methyl guanosine 5'-thiophosphate
modified_base           4
                        mod_base = OTHER
                        note = 2'-O-methyl uridine
modified_base           5
                        mod_base = OTHER
                        note = 2'-fluoro cytidine
modified_base           6
                        mod_base = OTHER
                        note = 2'-O-methyl adenosine
modified_base           7
                        mod_base = OTHER
                        note = 2'-fluoro cytidine
modified_base           8
                        mod_base = OTHER
                        note = 2'-O-methyl cytidine
modified_base           9
                        mod_base = OTHER
                        note = 2'-fluoro adenosine
modified_base           10
                        mod_base = OTHER
                        note = 2'-fluoro adenosine
```

```
modified_base       11
                    mod_base = OTHER
                    note = 2'-O-methyl adenosine
modified_base       12
                    mod_base = OTHER
                    note = 2'-O-methyl adenosine
modified_base       13
                    mod_base = OTHER
                    note = 2'-fluoro adenosine
modified_base       14
                    mod_base = OTHER
                    note = 2'-O-methyl guanosine
modified_base       15
                    mod_base = OTHER
                    note = 2'-fluoro cytidine
modified_base       16
                    mod_base = OTHER
                    note = 2'-O-methyl guanosine
modified_base       17
                    mod_base = OTHER
                    note = 2'-O-methyl cytidine
modified_base       18
                    mod_base = OTHER
                    note = 2'-fluoro adenosine
modified_base       19
                    mod_base = OTHER
                    note = 2'-O-methyl adenosine
modified_base       20
                    mod_base = OTHER
                    note = 2'-deoxy thymidine 5'-thiophosphate
modified_base       21
                    mod_base = OTHER
                    note = 2'-deoxy thymidine 5'-thiophosphate
misc_feature        21
                    note = 3'-O attached to a GalNAc-comprising compound via a
                    linker
SEQUENCE: 6
gcgtcaccaa aaagcgcaat t                                              21

SEQ ID NO: 7         moltype = RNA   length = 21
FEATURE              Location/Qualifiers
source               1..21
                     mol_type = other RNA
                     organism = synthetic construct
modified_base        1
                     mod_base = OTHER
                     note = 2'-O-methyl uridine
modified_base        2
                     mod_base = OTHER
                     note = 2'-deoxy thymidine 5'-thiophosphate
modified_base        3
                     mod_base = OTHER
                     note = 2'-O-methyl guanosine 5'-thiophosphate
modified_base        4
                     mod_base = OTHER
                     note = 2'-fluoro cytidine
modified_base        5
                     mod_base = OTHER
                     note = 2'-O-methyl guanosine
modified_base        6
                     mod_base = OTHER
                     note = 2'-fluoro cytidine
modified_base        7
                     mod_base = OTHER
                     note = 2'-deoxy thymidine
modified_base        8
                     mod_base = OTHER
                     note = 2'-O-methyl uridine 5'-thiophosphate
modified_base        9
                     mod_base = OTHER
                     note = 2'-fluoro uridine
modified_base        10
                     mod_base = OTHER
                     note = 2'-O-methyl uridine
modified_base        11
                     mod_base = OTHER
                     note = 2'-O-methyl uridine
modified_base        12
                     mod_base = OTHER
```

```
                            note = 2'-fluoro guanosine
modified_base               13
                            mod_base = OTHER
                            note = 2'-O-methyl guanosine
modified_base               14
                            mod_base = OTHER
                            note = 2'-fluoro uridine
modified_base               15
                            mod_base = OTHER
                            note = 2'-O-methyl guanosine
modified_base               16
                            mod_base = OTHER
                            note = 2'-fluoro adenosine
modified_base               17
                            mod_base = OTHER
                            note = 2'-O-methyl cytidine
modified_base               18
                            mod_base = OTHER
                            note = 2'-O-methyl guanosine
modified_base               20
                            mod_base = OTHER
                            note = 2'-O-methyl uridine 5'-thiophosphate
modified_base               21
                            mod_base = OTHER
                            note = 2'-O-methyl uridine 5'-thiophosphate
modified_base               19
                            mod_base = OTHER
                            note = 2'-deoxy cytidine
SEQUENCE: 7
ttgcgctttt tggtgacgct t                                              21

SEQ ID NO: 8                moltype = DNA  length = 22
FEATURE                     Location/Qualifiers
source                      1..22
                            mol_type = other DNA
                            organism = synthetic construct
SEQUENCE: 8
ggaccaggtg gaacagtata ag                                             22

SEQ ID NO: 9                moltype = DNA  length = 20
FEATURE                     Location/Qualifiers
source                      1..20
                            mol_type = other DNA
                            organism = synthetic construct
SEQUENCE: 9
tcaatgcgga ttcgagactg                                                20

SEQ ID NO: 10               moltype = DNA  length = 28
FEATURE                     Location/Qualifiers
source                      1..28
                            mol_type = other DNA
                            organism = synthetic construct
misc_feature                1
                            note = 5'-fluorophore
misc_feature                10
                            note = ZEN TM quencher
misc_feature                28
                            note = 3'-Iowa BlackTM FQ (IBFQ) quencher
SEQUENCE: 10
cagcttggcg gagtatgtct tttctagc                                       28

SEQ ID NO: 11               moltype = RNA  length = 21
FEATURE                     Location/Qualifiers
source                      1..21
                            mol_type = other RNA
                            organism = synthetic construct
modified_base               1
                            mod_base = OTHER
                            note = 2'-O-methyl uridine
modified_base               2
                            mod_base = OTHER
                            note = 2'-fluoro guanosine 5'-thiophosphate
modified_base               3
                            mod_base = OTHER
                            note = 2'-O-methyl adenosine 5'-thiophosphate
modified_base               4
                            mod_base = OTHER
                            note = 2'-O-methyl cytidine
modified_base               5
```

|   |   |
|---|---|
|   | mod_base = OTHER |
|   | note = 2'-O-methyl uridine |
| modified_base | 6 |
|   | mod_base = OTHER |
|   | note = 2'-fluoro uridine |
| modified_base | 7 |
|   | mod_base = OTHER |
|   | note = 2'-O-methyl uridine |
| modified_base | 8 |
|   | mod_base = OTHER |
|   | note = 2'-fluoro guanosine |
| modified_base | 9 |
|   | mod_base = OTHER |
|   | note = 2'-fluoro cytidine |
| modified_base | 10 |
|   | mod_base = OTHER |
|   | note = 2'-O-methyl adenosine |
| modified_base | 11 |
|   | mod_base = OTHER |
|   | note = 2'-O-methyl uridine |
| modified_base | 12 |
|   | mod_base = OTHER |
|   | note = 2'-O-methyl uridine |
| modified_base | 13 |
|   | mod_base = OTHER |
|   | note = 2'-O-methyl cytidine |
| modified_base | 14 |
|   | mod_base = OTHER |
|   | note = 2'-fluoro cytidine |
| modified_base | 15 |
|   | mod_base = OTHER |
|   | note = 2'-O-methyl adenosine |
| modified_base | 16 |
|   | mod_base = OTHER |
|   | note = 2'-fluoro guanosine |
| modified_base | 17 |
|   | mod_base = OTHER |
|   | note = 2'-O-methyl adenosine |
| modified_base | 18 |
|   | mod_base = OTHER |
|   | note = 2'-O-methyl cytidine |
| modified_base | 19 |
|   | mod_base = OTHER |
|   | note = 2'-O-methyl cytidine |
| modified_base | 20 |
|   | mod_base = OTHER |
|   | note = 2'-deoxy thymidine 5'-thiophosphate |
| modified_base | 21 |
|   | mod_base = OTHER |
|   | note = 2'-deoxy thymidine 5'-thiophosphate |
| SEQUENCE: 11 |   |
| tgactttgca ttccagacct t | 21 |
| SEQ ID NO: 12 | moltype = RNA  length = 21 |
| FEATURE | Location/Qualifiers |
| source | 1..21 |
|   | mol_type = other RNA |
|   | organism = synthetic construct |
| modified_base | 1 |
|   | mod_base = OTHER |
|   | note = 2'-O-methyl guanosine |
| modified_base | 2 |
|   | mod_base = OTHER |
|   | note = 2'-O-methyl guanosine 5'-thiophosphate |
| modified_base | 3 |
|   | mod_base = OTHER |
|   | note = 2'-O-methyl uridine 5'-thiophosphate |
| modified_base | 4 |
|   | mod_base = OTHER |
|   | note = 2'-O-methyl cytidine |
| modified_base | 5 |
|   | mod_base = OTHER |
|   | note = 2'-O-methyl uridine |
| modified_base | 6 |
|   | mod_base = OTHER |
|   | note = 2'-O-methyl guanosine |
| modified_base | 7 |
|   | mod_base = OTHER |
|   | note = 2'-fluoro guanosine |

```
modified_base          8
                       mod_base = OTHER
                       note = 2'-O-methyl adenosine
modified_base          9
                       mod_base = OTHER
                       note = 2'-fluoro adenosine
modified_base          10
                       mod_base = OTHER
                       note = 2'-fluoro uridine
modified_base          11
                       mod_base = OTHER
                       note = 2'-fluoro guanosine
modified_base          12
                       mod_base = OTHER
                       note = 2'-O-methyl cytidine
modified_base          13
                       mod_base = OTHER
                       note = 2'-O-methyl adenosine
modified_base          14
                       mod_base = OTHER
                       note = 2'-O-methyl adenosine
modified_base          15
                       mod_base = OTHER
                       note = 2'-O-methyl adenosine
modified_base          16
                       mod_base = OTHER
                       note = 2'-O-methyl guanosine
modified_base          17
                       mod_base = OTHER
                       note = 2'-O-methyl uridine
modified_base          18
                       mod_base = OTHER
                       note = 2'-O-methyl cytidine
modified_base          19
                       mod_base = OTHER
                       note = 2'-O-methyl adenosine
modified_base          20
                       mod_base = OTHER
                       note = 2'-deoxy thymidine 5'-thiophosphate
modified_base          21
                       mod_base = OTHER
                       note = 2'-deoxy thymidine 5'-thiophosphate
misc_feature           21
                       note = 3'-O attached to a GalNAc-comprising compound via a
                        linker
SEQUENCE: 12
ggtctggaat gcaaagtcat t                                                   21

SEQ ID NO: 13          moltype = DNA  length = 20
FEATURE                Location/Qualifiers
source                 1..20
                       mol_type = other DNA
                       organism = synthetic construct
SEQUENCE: 13
tcaccaagat cctgcatgtc                                                     20

SEQ ID NO: 14          moltype = DNA  length = 18
FEATURE                Location/Qualifiers
source                 1..18
                       mol_type = other DNA
                       organism = synthetic construct
SEQUENCE: 14
gttccacggg atgctctg                                                       18

SEQ ID NO: 15          moltype = DNA  length = 23
FEATURE                Location/Qualifiers
source                 1..23
                       mol_type = other DNA
                       organism = synthetic construct
misc_feature           1
                       note = 5'-fluorophore
misc_feature           10
                       note = ZEN TM quencher
misc_feature           23
                       note = 3'-Iowa BlackTM FQ (IBFQ) quencher
SEQUENCE: 15
caggtcgcca ctcatcttca cca                                                 23

SEQ ID NO: 16          moltype = RNA  length = 21
```

```
FEATURE            Location/Qualifiers
source             1..21
                   mol_type = other RNA
                   organism = synthetic construct
modified_base      20
                   mod_base = OTHER
                   note = 2'-deoxy thymidine
modified_base      21
                   mod_base = OTHER
                   note = 2'-deoxy thymidine
SEQUENCE: 16
gcgtcaccaa aaagcgcaat t                                              21

SEQ ID NO: 17      moltype = RNA   length = 21
FEATURE            Location/Qualifiers
source             1..21
                   mol_type = other RNA
                   organism = synthetic construct
modified_base      2
                   mod_base = OTHER
                   note = 2'-deoxy thymidine
modified_base      7
                   mod_base = OTHER
                   note = 2'-deoxy thymidine
SEQUENCE: 17
ttgcgctttt tggtgacgct t                                              21

SEQ ID NO: 18      moltype = RNA   length = 21
FEATURE            Location/Qualifiers
source             1..21
                   mol_type = other RNA
                   organism = synthetic construct
modified_base      20
                   mod_base = OTHER
                   note = 2'-deoxy thymidine
modified_base      21
                   mod_base = OTHER
                   note = 2'-deoxy thymidine
SEQUENCE: 18
tgactttgca ttccagacct t                                              21

SEQ ID NO: 19      moltype = RNA   length = 21
FEATURE            Location/Qualifiers
source             1..21
                   mol_type = other RNA
                   organism = synthetic construct
modified_base      20
                   mod_base = OTHER
                   note = 2'-deoxy thymidine
modified_base      21
                   mod_base = OTHER
                   note = 2'-deoxy thymidine
SEQUENCE: 19
ggtctggaat gcaaagtcat t                                              21
```